US005952486A

United States Patent [19]
Bloksberg et al.

[11] Patent Number: 5,952,486
[45] Date of Patent: Sep. 14, 1999

[54] MATERIALS AND METHODS FOR THE MODIFICATION OF PLANT LIGNIN CONTENT

[75] Inventors: Leonard N. Bloksberg; Ilkka Havukkala, both of Auckland, New Zealand; Alastair W. Grierson, Fife, United Kingdom

[73] Assignees: Genesis Research & Development Corporation Limited; Fletcher Challenge Forests Limited, both of New Zealand

[21] Appl. No.: 08/975,316

[22] Filed: Nov. 21, 1997

Related U.S. Application Data

[63] Continuation-in-part of application No. 08/713,000, Sep. 11, 1996, Pat. No. 5,850,020.

[51] Int. Cl.$^6$ .............................. C12N 15/29; C12N 5/04; A01H 4/00; A01H 5/10
[52] U.S. Cl. ...................... 536/23.6; 536/23.1; 536/23.2; 800/278; 800/298; 800/319
[58] Field of Search .................................. 536/23.1, 23.6, 536/23.2; 800/278, 298, 319

[56] References Cited

FOREIGN PATENT DOCUMENTS

| | | | |
|---|---|---|---|
| 0513884 | 11/1992 | European Pat. Off. | C12N 15/11 |
| 0516958 | 12/1992 | European Pat. Off. | C12N 15/54 |
| 0632128 | 1/1995 | European Pat. Off. | C12N 15/53 |
| 0716147 | 6/1996 | European Pat. Off. | C12N 15/82 |
| 9008828 | 8/1990 | WIPO | C12N 15/82 |
| 9305159 | 3/1993 | WIPO | C12N 15/53 |
| 9305160 | 3/1993 | WIPO | C12N 15/54 |
| 9315599 | 8/1993 | WIPO | C12N 15/00 |
| 9324638 | 12/1993 | WIPO | C12N 15/82 |
| 9408036 | 4/1994 | WIPO | C12N 21/04 |
| 9421794 | 9/1994 | WIPO | C12N 15/29 |
| 9423044 | 10/1994 | WIPO | C12N 15/82 |
| 9507993 | 3/1995 | WIPO | C12N 15/82 |
| 9527790 | 10/1995 | WIPO | C12N 15/53 |
| 9620595 | 7/1996 | WIPO | A01N 35/02 |
| 9723599 | 7/1997 | WIPO . | |

OTHER PUBLICATIONS

Napoli et al. The Plant Cell. 1989. vol. 2:278–289.

Carvalho et al. The EMBO J. 1992. vol. 11:29995–2602.

Atanassova, R. et al. Altered lignin composition in transgenic tobacco expressing O–methyltransferase sequence in sense and antisense orientation, *Plant Jnl.* 8:465–477, 1995.

Chabbert et al., Manipulation of lignin quality in transgenic poplar, *Biotechnol. Pulp. Pap. Ind. Proc. Int. Conf.* 6$^{th,}$ pp. 319–322, 1995.

Baucher, M. et al., Higher extractability of lignin in poplar by reducing cinnamyl alcohol dehydrogenase activity, *Somatic Cell Genetics and Molecular Genetics of Trees*, ISBN 0–7923–4179–1, pp. 153–158, 1996.

Boudet A. M. et al., La lignification domestiquee *Bio Futur* 158:27–31, 1996.

Boudet A. M. Genes involved in monolignol biosynthesis and their manipulation for tailoring new lignins *Am. Chem Soc. Abstracts of Paper at National Meeting*, No. 1, 1996.

Elkind Y. et al., Abnormal plant development and down–regulation of phenylpropanoid biosynthesis in transgenic tobacco containing a heterologous phenylalanine ammonia–lyase gene *Proc. Natl Acad. Sci. USA* 87:9057–9061, 1990.

Lagrimini, L M., Wound–induced deposition of polyphenols in transgenic plants overexpressing peroxidase *Plant Physiol.* 96:577–583, 1991.

Liu, T.Y. et al. Lignin contect and composition in tobacco plants with over and under expressed peroxidase, *Supplement to Plant Physiol.* 102:103, 1993.

McIntyre, C.L. et al. Strategies for the suppression of peroxidase gene expression in tobacco. II. In vivo suppression of peroxidase activity in transgenic tobacco using ribozyme and antisense constructs *Transgenic Research* 5:263–270, 1996.

Poeydomenge O. et al. A cDNA encoding S–adenosyl–L–methionine:caffeic acid 3–O–methyltransferase from eucalyptus, *Plant Physiol.* 105:749–750, 1994.

Raynal et al. A. thaliana transcribed sequence; clone PAP790; 5' end similar to cinnamyl alcohol dehydrogenase; Stylosanthes hmilis, EMBL Accession No. Z46703, Nov. 18, 1994.

Goffner D. et al., E. gunnii mRNA for cinnamyl alcohol dehydrogenase, EMBL Accession No. X88797, Dec. 31, 1995.

Newman T., et al., 10030 Arabidopsis thaliana cDNA clone 143C13T7, EMBL Accession No. T46767, Feb. 11, 1995.

Zhang, X.H. et al., Pinus taedae phenylalanine ammonia–lyase (lpPAL) gene complete cds, EMBL Accession No. U39792, Jan. 1, 1996.

Voo, K.S. et al. Pinus taeda PT4CL2 4–coumarate–CoA ligase enzyme, mRNA complete cds, EMBL Accession No. U12013, Jul. 27, 1994.

Zhang X.H. et al., Pinus taeda xylem 4–coumarate:CoA ligase (lp4CL–1) gene, complete cds, EMBL Accession No. U39405, Jan. 1, 1996.

Davies, K.M. et al. Malus sp. mRNA for anthocyanin hydroxylase, EMBL Accession No. X71360, Apr. 27, 1993.

Hrmova M. et al., Hordeum vulgare beta–d–glucan exohydrolase, isoenzyme exoII, mRNA, complete cds, EMBL Accession No. U46003, Feb. 29, 1996.

(List continued on next page.)

*Primary Examiner*—Lynette R. F. Smith
*Assistant Examiner*—Ousama M-Foiz Zaghmout
*Attorney, Agent, or Firm*—Ann W. Speckman; Janet Sleath

[57] ABSTRACT

Novel isolated DNA sequences associated with the lignin biosynthetic pathway are provided, together with DNA constructs including such sequences. Methods for the modulation of lignin content in plants are also disclosed, the methods comprising incorporating one or more of the inventive DNA sequences or a sequence complementary to an inventive DNA sequence into the genome of a plant.

23 Claims, 1 Drawing Sheet

OTHER PUBLICATIONS

Willekens, H.D. N. plumbaginifolia mRNA for catalase (cat3 gene), EMBL Accession No. Z36977, Sep. 7, 1994.

Ritter D. et al., Gossypium hirsutum peroxidase mRNA, complete cds, EMBL Accession No. L08199, Dec. 24, 1992.

Meyer K. et al., Arabidopsis thaliana ferulate–5–hydroxylase (FAH1) mRNA, completed cds, EMBL Accession No. U38416, Aug. 13, 1996.

Meyer K. et al., Ferulate–5–hydroxylase from Arabidopsis thaliana defines a new family of cytochrome P450–dependent monooxygenases *Proc. Natl. Acad. Sci. USA* 93:6869–6874, 1996.

Sewalt, V.J.H., et al. Reduced lignin content and altered lignin composition in transgenic tobacco down–regulated in expression of L–phenylalanine ammonia–lyase or cinnamate 4–hydroxylase *Plant Physiol.* 115:41–50, 1997.

Rech. P. et al., E. gunii mRNA for caffeoyl–CoA O–methyltransferase, EMBL Accession No. Y12228, Apr. 8, 1997.

Bachem, C.W.B., et al. Antisense expression of polyphenol oxidase genes inhibits enzymatic browning in potato tubers, *Biotechnology* 12:1101–1105, 1994.

Udagama–Randeniya, P.V. et al., Coniferyl alcohol oxidase: A catechol oxidase? *Trees* 10:102–108, 1995.

Dharmawardhana, D.P. et al., A beta–glycosidase from lodgepole pine xylem specific for the lignin precursor coniferin *Plant Physiol* 107:331–339, 1995.

Database Dissabs, AN97:45741 Dissabs Order No. AARNN14739, Dharmawardhana, D.P. et al. A biochemical and molecular study of lignin biosynthesis (Pinus contorta, glucosidase, conferin, xylem).

Bao W. et al. A laccase associated with lignification in loblolly pine xylem *Science* 260:672–674, 1993.

Shiokawa, T. et al., Expression analysis of a cinnamic acid 4–hydroxylase gene from a hybrid aspen, Populus kitakamiensis, *Chem. Abstracts*, vol. 125, No. 13, abstract No. 163462, Sep. 23, 1996.

Zhang, X–H. et al. Plant Physiol. (1997) 113:65–74.

Tsai, C–J et al. Plant Physiol. (1998) 117:101–112.

Dixon, R. A. et al., Metabolic engineering: prospects for crop improvement through genetic manipulation of phenylpropanoid biosynthesis and defense responses—a review, *Gene Papers* 179:61–71, 1996.

Hotze, M. et al., Cinnamate 4–hydroxylase from Catharanthus roseus, and a strategy for the functional expression of plant cytochrome $P_{450}$ proteins as translational fusions with $P_{450}$ reductase in *Escherichia coli, FEBS letters* 374:345–350, 1995.

Hotze, M., et al., C. roseus mRNA for cinnamate 4–hydroxylase (CYP73), *EMBL Sequence Database, Rel. 39*, Apr. 15, 1994, Accession No. Z32563, (XP–002054206).

Mizutani, M. et al., Molecular Cloning and Sequencing of a cDNA Encoding Mung Bean Cytochrome P450 Possessing Cinnamate 4–Hydroxylase Activity, *Biochemical and Biophysical Research Communications* 190:3, 875–880, 1993.

Kawai, S., et al., Populus kitakamiensis cyp73a gene for cinnamic acid 4–hydroxylase complete cds. *EMBL Sequence Database, Rel. 46*, Dec. 30, 1995, Accession No. D82812 (XP002054135), Sewalt et al., Reduced Lignin Content and Altered Lignin Composition in Transgenic Tobacco Down–Regulated in Expression of L–Phenylalanine Ammonia–Lyase or Cinnamate 4–Hydroxylase, *Plant Physiol.* 115:41–50, 1997.

Boudet, A.M., et al., Tansley Review No. 80 Biochemistry and molecular biology of lignification, *New Phytoolgist* 129:203–236, 1995.

Boudet, A.M. et al., Lignin genetic engineering, *Molecular Breeding* 2: 25–39, 1996.

Shiokawa, T., et al., Expression analysis of a cinnamic acid 4–hydroxylase gene from a hybrid aspen, Populus kitakamiensis, Chemical Abstracts 125:13, 1996.

Poeydomenge, O., et al., A cDNA Encoding S–Adenosyl–L- –Methionine:Caffeic Acid 3–0–Methyltransferase from *Eucalyptus, Plant Physiol* 105:749–750, 1994.

Mason, M.E., et al., Pinus elliottii PEC18 mRNA, partial sequence, *EMBL Sequence Database, Rel. 47* May 31, 1996, Accession No. U55006 (XP 002054138).

Wagner, A., et al., Pinus radiata cinnamyl alcohol dehydrogenase (CAD) mRNA, complete cds, *EMBL Sequence Database, Rel. 48* Jul. 28, 1996, Accession No. U62394 (XP002054137).

Van Doorsselaere, J., et al., A novel lignin in poplar trees with a reduced caffeic acid/5–hydroxyferulic acid 0–methyltransferase activity, *Plant Journal* 8:6, 855–864, 1995.

Ni, Weiting et al., Reduced lignin in transgenic plants containing a caffeic acid 0=methyltransferase antisense gene, *Transgenic Research* 3: 120–126, 1994.

Halpin, C. et al., Manipulation of lignin quality by down-regulation of cinnamyl alcohol dehydrogenase, *Plant Journal* 6:3, 339–350, 1994.

```
                       SEQUENCE LISTING (1) GENERAL INFORMATION:

(iii) NUMBER OF SEQUENCES: 88

(2) INFORMATION FOR SEQ ID NO:1:

(i) SEQUENCE CHARACTERISTICS:
        (A) LENGTH: 535 base pairs
        (B) TYPE: nucleic acid
        (C) STRANDEDNESS: single
        (D) TOPOLOGY: linear (xi) SEQUENCE DESCRIPTION: SEQ ID NO:1:

CTTCGCGCTA CCGCATACTC CACCACCGCG TGCAGAAGAT GAGCTCGGAG GGTGGGAAGG      60

AGGATTGCCT CGGTTGGGCT GCCCGGGACC CTTCTGGGTT CCTCTCCCCN TACAAATTCA     120

CCCGCAGGCC GTGGGAAGCG AAGACGTCTC GATTAAGATC ACGCACTGTG GAGTGTGCTA     180

CGCAGATGTG GCTTGGACTA GGAATGTGCA GGACACTCC AAGTATCCTC TGGTGCCGGG      240

GCACGAGATA GTTGGAATTG TGAAACAGGT TGGCTCCAGT GTCCAACGCT TCAAAGTTGG     300

CGATCATGTG GGGGTGGGAA CTTATGTCAA TTCATGCAGA GAGTGCGAGT ATTGCAATGA     360

CAGGCTAGAA GTCCAATGTG AAAAGTCGGT TATGACTTTT GATGGAATTG ATGCAGATGG     420

TACAGTGACA AAGGGAGGAT ATTCTAGTCA CATTGTCGTC CATGAAAGGT ATTGCGTCAG     480

GATTCCAGAA AACTACCCGA TGGATCTAGC AGCGCATTGC TCTGTGCTGG ATCAC         535

(2) INFORMATION FOR SEQ ID NO:2:

(i) SEQUENCE CHARACTERISTICS:
        (A) LENGTH: 671 base pairs
        (B) TYPE: nucleic acid
        (C) STRANDEDNESS: single
        (D) TOPOLOGY: linear (xi) SEQUENCE DESCRIPTION: SEQ ID NO:2:

GCGCCTGCAG GTCGACACTA GTGGATCCAA AGAATTCGGC ACGAGGTTGC AGGTCGGGGA      60

TGATTTGAAT CACAGAAACC TCAGCGATTT TGCCAAGAAA TATGGCAAAA TCTTTCTGCT     120

CAAGATGGGC CAGAGGAATC TTGTGGTAGT TTCATCTCCC GATCTCGCCA AGGAGGTCCT     180

GCACACCCAG GGCGTCGAGT TTGGGTCTCG AACCCGGAAC GTGGTGTTCG ATATCTTCAC     240

GGGCAAGGGG CAGGACATGG TGTTCACCGT CTATGGAGAT CACTGGAGAA AGATGCGCAG     300

GATCATGACT GTGCCTTTCT TTACGAATAA AGTTGTCCAG CACTACAGAT TCGCGTGGGA     360

AGACGAGATC AGCCGCGTGG TCGCGGATGT GAAATCCCGC GCCGAGTCTT CCACCTCGGG     420

CATTGTCATC CGTAGCGCCT CCAGCTCATG ATGTATAATA TTATGTATAG GATGATGTTC     480
```

```
GACAGGAGAT TCGAATCCGA GGACGACCCG CTTTTCCTCA AGCTCAAGGC CCTCAACGGA      540

GAGCGAAGTC GATTGGCCCA GAGCTTTGAG TACAATTATG GGGATTTCAT TCCCAGTCTT      600

AGGCCCTTCC TCAGAGGTTA TCACAGAATC TGCAATGAGA TTAAAGAGAA ACGGCTCTCT      660

CTTTTCAAGG A                                                          671

(2) INFORMATION FOR SEQ ID NO:3:

(i) SEQUENCE CHARACTERISTICS:
        (A) LENGTH: 940 base pairs
        (B) TYPE: nucleic acid
        (C) STRANDEDNESS: single
        (D) TOPOLOGY: linear (xi) SEQUENCE DESCRIPTION: SEQ ID NO:3:

CTTCAGGACA AGGGAGAGAT CAATGAGGAT AATGTTTTGT ACATCGTTGA GAACATCAAC       60

GTTGCAGCAA TTGAGACAAC GCTGTGGTCG ATGGAATGGG AATAGCGGA GCTGGTGAAC      120

CACCAGGACA TTCAGAGCAA GGTGCGCGCA GAGCTGGACG CTGTTCTTGG ACCAGGCGTG      180

CAGATAACGG AACCAGACAC GACAAGGTTG CCCTACCTTC AGGCGGTTGT GAAGGAAACC      240

CTTCGTCTCC GCATGGCGAT CCCGTTGCTC GTCCCCACA TGAATCTCCA CGACGCCAAG      300

CTCGGGGGCT ACGATATTCC GGCAGAGAGC AAGATCCTGG TGAACGCCTG GTGGTTGGCC      360

AACAACCCCG CCAACTGGAA GAACCCCGAG GAGTTCCGCC CCGAGCGGTT CTTCGAGGAG      420

GAGAAGCACA CCGAAGCCAA TGGCAACGAC TTCAAATTCC TGNCCTTCGG TGTGGGGAGG      480

AGGAGCTGCC CGGGAATCAT TCTGGCGCTG CTCTCCTCGC ACTCTCCATC GGAAGACTTG      540

TTCAGAACTT CCACCTTCTG CCGCCGCCCG GGCAGAGCAA AGTGGATGTC ACTGAGAAGG      600

GCGGGCAATT CAGCCTTCAC ATTCTCAACC ATTCTCTCAT CGTCGCCAAG CCCATAGCTT      660

CTGCTTAATC CCAACTTGTC AGTGACTGGT ATATAAATGC GCGCACCTGA ACAAAAAACA      720

CTCCATCTAT CATGACTGTG TGTGCGTGTC CACTGTCGAG TCTACTAAGA GCTCATAGCA      780

CTTCAAAAGT TTGCTAGGAT TTCAATAACA GACACCGTCA ATTATGTCAT GTTTCAATAA      840

AAGTTTGCAT AAATTAAATG ATATTTCAAT ATACTATTTT GACTCTCCAC CAATTGGGGA      900

ATTTTACTGC TAAAAAAAAA AAAAAAAAA AAAAAAAAA                             940

(2) INFORMATION FOR SEQ ID NO:4:

(i) SEQUENCE CHARACTERISTICS:
        (A) LENGTH: 949 base pairs
        (B) TYPE: nucleic acid
        (C) STRANDEDNESS: single
        (D) TOPOLOGY: linear (xi) SEQUENCE DESCRIPTION: SEQ ID NO:4:

NNGCTCNACC GACGGTGGAC GGTCCGCTAC TCAGTAACTG AGTGGGATCC CCCGGGCTGA       60

CAGGCAATTC GATTTAGCTC ACTCATTAGG CACCCCAGGC TTTACACTTT ATGCTTCCGG      120

CTCGTATGTT GTGTGGAATT GTGAGCGGAT AACAATTTCA CACAGGAAAC AGCTATGACC      180

ATGATTACGC CAAGCGCGCA ATTAACCCTC ACTAAAGGGA ACAAAAGCTG GAGCTCCACC      240

GCGGTGGCGG CCGCTCTAGA ACTAGTGGAT CCAAAGAATT CGGCACGAGA CCCAGTGACC      300

TTCAGGCCTG AGAGATTTCT TGAGGAAGAT GTTGATATTA AGGGCCATGA TTACAGGCTA      360

CTGCCATTGG TGCAGGGCGC AGGATCTGCC CTGGTGCACA ATTGGGTATT AATTTAGTTC      420

AGTCTATGTT GGGACACCTG CTTCATCATT TCGTATGGGC ACCTCCTGAG GGAATGAAGG      480

CAGAAGACAT AGATCTCACA GAGAATCCAG GGCTTGTTAC TTTCATGGCC AAGCCTGTGC      540
```

```
AGGCCATTGC TATTCCTCGA TTGCCTGATC ATCTCTACAA GCGACAGCCA CTCAATTGAT        600

CAATTGATCT GATAGTAAGT TTGAATTTTG TTTTGATACA AAACGAAATA ACGTGCAGTT        660

TCTCCTTTTC CATAGTCAAC ATGCAGCTTT CTTTCTCTGA AGCGCATGCA GCTTTCTTTC        720

TCTGAAGCCC AACTTCTAGC AAGCAATAAC TGTATATTTT AGAACAAATA CCTATTCCTC        780

AAATTGAGWA TTTCTCTGTA GGGGNNGNTA ATTGTGCAAT TTGCAAGNAA TAGTAAAGTT        840

TANTTTAGGG NATTTTAATA GTCCTANGTA ANANGNGGNA ATGNTAGNGG GCATTNAGAA        900

ANCCCTAATA GNTGTTGGNG GNNGNTAGGN TTTTTNACCA AAAAAAAAA                    949
```

(2) INFORMATION FOR SEQ ID NO:5:

(i) SEQUENCE CHARACTERISTICS:
        (A) LENGTH: 959 base pairs
        (B) TYPE: nucleic acid
        (C) STRANDEDNESS: single
        (D) TOPOLOGY: linear (xi) SEQUENCE DESCRIPTION: SEQ ID NO:5:

```
GAATTCGGCA CGAGAAAGCC CTAGAATTTT TTCAGCATGC TATCACAGCC CCAGCGACAA         60

CTTTAACTGC AATAACTGTG GAAGCGTACA AAAGTTTGT CCTAGTTTCT CTCATTCAGA         120

CTGGTCAGGT TCCAGCATTT CCAAAATACA CACCTGCTGT TGTCCAAAGA AATTTGAAAT        180

CTTGCACTCA GCCCTACATT GATTTAGCAA ACAACTACAG TAGTGGGAAA ATTTCTGTAT        240

TGGAAGCTTG TGTCAACACG AACACAGAGA AGTTCAAGAA TGATAGTAAT TTGGGGTTAG        300

TCAAGCAAGT TTTGTCATCT CTTTATAAAC GGAATATTCA GAGATTGACA CAGACATATC        360

TGACCCTCTC TCTTCAAGAC ATAGCAAGTA CGGTACAGTT GGAGACTGCT AAGCAGGCTG        420

AACTCCATGT TCTGCAGATG ATTCAAGATG GTGAGATTTT TGCAACCATA AATCAGAAAG        480

ATGGGATGGT GAGCTTCAAT GAGGATCCTG AACAGTACAA AACATGTCAG ATGACTGAAT        540

ATATAGATAC TGCAATTCGG AGAATCATGG CACTATCAAA GAAGCTCACC ACAGTAGATG        600

AGCAGATTTC GTGTGATCAT TCCTACCTGA GTAAGGTGGG GAGAGAGCGT TCAAGATTTG        660

ACATAGATGA TTTTGATACT GTTCCCCAGA AGTTCANAAA TATGTAACAA ATGATGTAAA        720

TCATCTTCAA GACTCGCTTA TATTCATTAC TTTCTATGTG AATTGATAGT CTGTTAACAA        780

TAGTACTGTG GCTGAGTCCA GAAAGGATCT CTCGGTATTA TCACTTGACA TGCCATCAAA        840

AAAATCTCAA ATTTCTCGAT GTCTAGTCTT GATTTTGATT ATGAATGCGA CTTTTAGTTG        900

TGACATTTGA GCACCTCGAG TGAACTACAA AGTTGCATGT TAAAAAAAAA AAAAAAAA         959
```

(2) INFORMATION FOR SEQ ID NO:6:

(i) SEQUENCE CHARACTERISTICS:
        (A) LENGTH: 1026 base pairs
        (B) TYPE: nucleic acid
        (C) STRANDEDNESS: single
        (D) TOPOLOGY: linear (xi) SEQUENCE DESCRIPTION: SEQ ID NO:6:

```
GAATTCGGCA CGAGCTTTGA GGCAACCTAC ATTCATTGAA TCCCAGGATT TCTTCTTGTC         60

CAAACAGGTT TAAGGAAATG GCAGGCACAA GTGTTGCTGC AGCAGAGGTG AAGGCTCAGA        120

CAACCCAAGC AGAGGAGCCG GTTAAGGTTG TCCGCCATCA AGAAGTGGGA CACAAAAGTC        180

TTTTGCAGAG CGATGCCCTC TATCAGTATA TATTGGAAAC GAGCGTGTAC CCTCGTGAGC        240

CCGAGCCAAT GAAGGAGCTC CGCGAAGTGA CTGCCAAGCA TCCCTGGAAC CTCATGACTA        300

CTTCTGCCGA TGAGGGTCAA TTTCTGGGCC TCCTGCTGAA GCTCATTAAC GCCAAGAACA        360
```

```
CCATGGAGAT TGGGGTGTAC ACTGGTTACT CGCTTCTCAG CACAGCCCTT GCATTGCCCG    420

ATGATGGAAA GATTCTAGCC ATGGACATCA ACAGAGAGAA CTATGATATC GGATTGCCTA    480

TTATTGAGAA AGCAGGAGTT GCCCACAAGA TTGACTTCAG AGAGGGCCCT GCTCTGCCAG    540

TTCTGGACGA ACTGCTTAAG AATGAGGACA TGCATGGATC GTTCGATTTT GTGTTCGTGG    600

ATGCGGACAA AGACAACTAT CTAAACTACC ACAAGCGTCT GATCGATCTG GTGAAGGTTG    660

GAGGTCTGAT TGCATATGAC AACACCCTGT GGAACGGATC TGTGGTGGCT CCACCCGATG    720

CTCCCCTGAG GAAATATGTG AGATATTACA GAGATTTCGT GATGGAGCTA ACAAGGCCC    780

TTGCTGTCGA TCCCCGCATT GAGATCAGCC AAATCCCAGT CGGTGACGGC GTCACCCTTT    840

GCAGGCGTGT CTATTGAAAA CAATCCTTGT TTCTGCTCGT CTATTGCAAG CATAAAGGCT    900

CTCTGATTAT AAGGAGAACG CTATAATATA TGGGGTTGAA GCCATTTGTT TTGTTTAGTG    960

TATTGATAAT AAAGTAGTAC AGCATATGCA AGTTTGTAT CAAAAAAAAA AAAAAAAAA    1020

AAAAAA                                                              1026

(2) INFORMATION FOR SEQ ID NO:7:

(i) SEQUENCE CHARACTERISTICS:
        (A) LENGTH: 1454 base pairs
        (B) TYPE: nucleic acid
        (C) STRANDEDNESS: single
        (D) TOPOLOGY: linear (xi) SEQUENCE DESCRIPTION: SEQ ID NO:7:

GAATTCGGCA CGAGGCCAAC TGCAAGCAAT ACAGTACAAG AGCCAGACGA TCGAATCCTG     60

TGAAGTGGTT CTGAAGTGAT GGGAAGCTTG GAATCTGAAA AAACTGTTAC AGGATATGCA    120

GCTCGGGACT CCAGTGGCCA CTTGTCCCCT TACACTTACA ATCTCAGAAA GAAAGGACCT    180

GAGGATGTAA TTGTAAAGGT CATTTACTGC GGAATCTGCC ACTCTGATTT AGTTCAAATG    240

CGTAATGAAA TGGACATGTC TCATTACCCA ATGGTCCCTG GCATGAAGT GGTGGGGATT    300

GTAACAGAGA TTGGCAGCGA GGTGAAGAAA TTCAAAGTGG GAGAGCATGT AGGGGTTGGT    360

TGCATTGTTG GGTCCTGTCG CAGTTGCGGT AATTGCAATC AGAGCATGGA ACAATACTGC    420

AGCAAGAGGA TTTGGACCTA CAATGATGTG AACCATGACG GCACACCTAC TCAGGGCGGA    480

TTTGCAAGCA GTATGGTGGT TGATCAGATG TWTGTGGTTC GAATCCCGGA GAATCTTCCT    540

CTGGAACAAG CGGCCCCTCT GTTATGTGCA GGGGTTACGA TTTTCAGCCC AATGAAGCAT    600

TTCGCCATGA CAGAGCCCGG GAAGAAATGT GGGATTTTGG GTTTAGGAGG CGTGGGGCAC    660

ATGGGTGTCA AGATTGCCAA AGCCTTTGGA CTCCACGTGA CGGTTATCAG TTCGTCTGAT    720

AAAAAGAAAG AAGAAGCCAT GGAAGTCCTC GGCGCCGATG CTTATCTTGT TAGCAAGGAT    780

ACTGAAAAGA TGATGGAAGC AGCAGAGAGC CTAGATTACA TAATGGACAC CATTCCAGTT    840

GCTCATCCTC TGGAACCATA TCTTGCCCTT CTGAAGACAA ATGGAAAGCT AGTGATGCTG    900

GGCGTTGTTC CAGAGTCGTT GCACTTCGTG ACTCCTCTCT TAATACTTGG GAGAAGGAGC    960

ATAGCTGGAA GTTTCATTGG CAGCATGGAG GAAACACAGG AAACTCTAGA TTTCTGTGCA   1020

GAGAAGAAGG TATCATCGAT GATTGAGGTT GTGGGCCTGG ACTACATCAA CACGGCCATG   1080

GAAAGGTTGG AGAAGAACGA TGTCCGTTAC AGATTTGTGG TGGATGTTGC TAGAAGCAAG   1140

TTGGATAATT AGTCTGCAAT CAATCAATCA GATCAATGCC TGCATGCAAG ATGAATAGAT   1200

CTGGACTAGT AGCTTAACAT GAAAGGGAAA TTAAATTTTT ATTTAGGAAC TCGATACTGG   1260

TTTTTGTTAC TTTAGTTTAG CTTTTGTGAG GTTGAAACAA TTCAGATGTT TTTTTAACTT   1320
```

```
GTATATGTAA AGATCAATTT CTCGTGACAG TAAATAATAA TCCAATGTCT TCTGCCAAAT    1380

TAATATATGT ATTCGTATTT TTATATGAAA AAAAAAAAAA AAAAAAAAAA AAAAAAAAAA    1440

AAAAAAAAAA AAAA                                                      1454

(2) INFORMATION FOR SEQ ID NO:8:

(i) SEQUENCE CHARACTERISTICS:
        (A) LENGTH: 740 base pairs
        (B) TYPE: nucleic acid
        (C) STRANDEDNESS: single
        (D) TOPOLOGY: linear (xi) SEQUENCE DESCRIPTION: SEQ ID NO:8:

GAATTCGGCA CGAGACCATT TCCAGCTAAT ATTGGCATAG CAATTGGTCA TTCTATCTTT      60

GTCAAAGGAG ATCAAACAAA TTTTGAAATT GGACCTAATG GTGTGGAGGC TAGTCAGCTA     120

TACCCAGATG TGAAATATAC CACTGTCGAT GAGTACCTCA GCAAATTTGT GTGAAGTATG     180

CGAGATTCTC TTCCACATGC TTCAGAGATA CATAACAGTT TCAATCAATG TTTGTCCTAG     240

GCATTTGCCA AATTGTGGGT TATAATCCTT CGTAGGTGTT TGGCAGAACA GAACCTCCTG     300

TTTAGTATAG TATGACGAGC TAGGCACTGC AGATCCTTCA CACTTTTCTC TTCCATAAGA     360

AACAAATACT CACCTGTGGT TTGTTTTCTT TCTTTCTGGA ACTTTGGTAT GGCAATAATG     420

TCTTTGGAAA CCGCTTAGTG TGGAATGCTA AGTACTAGTG TCCAGAGTTC TAAGGGAGTT     480

CCAAAATCAT GGCTGATGTG AACTGGTTGT TCCAGAGGGT GTTTACAACC AACAGTTGTT     540

CAGTGAATAA TTTTGTTAGA GTGTTTAGAT CCATCTTTAC AAGGCTATTG AGTAAGGTTG     600

GTGTTAGTGA ACGGAATGAT GTCAAATCTT GATGGGCTGA CTGACTCTCT TGTGATGTCA     660

AATCTTGATG GATTGTGTCT TTTTCAATGG TAAAAAAAAA AAAAAAAAAA AAAAAAAAAA     720

AAAAAAAAAA AAAAAAAAAA                                                740

(2) INFORMATION FOR SEQ ID NO:9:

(i) SEQUENCE CHARACTERISTICS:
        (A) LENGTH: 624 base pairs
        (B) TYPE: nucleic acid
        (C) STRANDEDNESS: single
        (D) TOPOLOGY: linear (xi) SEQUENCE DESCRIPTION: SEQ ID NO:9:

GAATTCCTGC AGCCCGGGGG ATCCACTAGT TCTAGAGCGG CCGCCACCGC GGTGGAGCTC      60

GCGCGCCTGC AGGTCGACAC TAGTGGATCC AAAGAATTCG GCACGAGGCC CGACGGCCAC     120

TTGTTGGACG CCATGGAAGC TCTCCGGAAA GCCGGGATTC TGGAACCGTT TAAACTGCAG     180

CCCAAGGAAG GACTGGCTCT CGTCAACGGC ACAGCGGTGG GATCCGCCGT GGCCGCGTCC     240

GTCTGTGTTG ACGCCAACGT GCTGGGCGTG CTGGCTGAGA TTCTGTCTGC GCTCTTCTGC     300

GAGGTGATGC AAGGGAAACC GGAGTTCGTA GATCCGTTAA CCCACCAGTT GAAGCACCAC     360

CCAGGGCAGA TCGAAGCCGC GGCCGTCATG GAGTTCCTCC TCGACGGTAG CGACTACGTG     420

AAAGAAGCAG CGCGGCTTCA CGAGAAAGAC CCGTTGAGCA AACCGAAACA AGACCGCTAC     480

GCTCTGCGAA CATCGCCACA GTGGTTGGGG CCTCCGATCG AAGTCATCCG CGCTGCYACT     540

CACTCCATCG AGCGGGAGAT CAATTCCGTC AACGACAATC CGTTAATCGA TGTCTCCAGG     600

GACATGGCTG TCCACGGCGG CAAC                                           624

(2) INFORMATION FOR SEQ ID NO:10:

(i) SEQUENCE CHARACTERISTICS:
```

```
        (A) LENGTH: 278 base pairs
        (B) TYPE: nucleic acid
        (C) STRANDEDNESS: single
        (D) TOPOLOGY: linear (xi) SEQUENCE DESCRIPTION: SEQ ID NO:10:

GAATTCCTGC AGCCCGGGGG ATCCACTAGT TCTAGAGCGG CCGCCACCGC GGTGGAGCTC      60

CAGTACCTGG CCAACCCCGT CACGACTCAC GTCCAGAGCG CCGAACAACA CAACCAGGAT     120

GTCAATTCCC TCGGCTTGAT CTCCGCCAGA AAGACTGCCG AGGCCGTTGA GATTTTAAAG     180

CTGATGTTCG CTACATATCT GGTGGCCTTA TGCCAGGCGA TCGATCTCCG GCACCTGGAA     240

GAAAACATGC GATCCGTTGT GAAGCACGTA GTCTTGCA                             278

(2) INFORMATION FOR SEQ ID NO:11:

(i) SEQUENCE CHARACTERISTICS:
        (A) LENGTH: 765 base pairs
        (B) TYPE: nucleic acid
        (C) STRANDEDNESS: single
        (D) TOPOLOGY: linear (xi) SEQUENCE DESCRIPTION: SEQ ID NO:11:

GAGCTCCTGC AAGTCATCGA TCATCAGCCC GTTTTCTCGT ACATCGACGA TCCCACAAAT      60

CCATCATACG CGCTTATGCT CCAACTCAGA GAAGTGCTCG TAGATGAGGC TCTCAAATCA     120

TCTTGCCCAG ACGGGAATGA CGAATCCGAT CACAATTTGC AGCCCGCTGA GAGCGCTGGA     180

GCTGCTGGAA TATTACCCAA TTGGGTGTTT AGCAGGATCC CCATATTTCA AGAGGAGTTG     240

AAGGCCCGTT TAGAGGAAGA GGTTCCGAAG GCGAGGGAAC GATTCGATAA TGGGGACTTC     300

CCAATTGCAA ACAGAATAAA CAAGTGCAGG ACATATCCCA TTTACAGATT CGTGAGATCA     360

GAGTTGGGAA CCGATTTGCT AACAGGGCCC AAGTGGAGAA GCCCCGGCGA AGATATAGAA     420

AAGGTATTTG AGGGCATTTG CCAAGGGAAA ATTGGAAACG TGATCCTCAA ATGTCTGGAC     480

GCTTGGGGTG GGTGCGCTGG ACCATTCACT CCACGTGCAT ATCCTGCGTC TCCTGCAGCG     540

TTCAATGCCT CATATTGGGC ATGGTTTGAT AGCACCAAAT CACCCTCTGC AACGAGCGGC     600

AGAGGTTTCT GGAGCGCCCA ACAACAACAA GTTCTTTGAT TTAACTGACT CTTAAGCATT     660

CCTAAACAGC TTGTTCTTCG CAATAACGAA TCTTTCATCT TCGTTACTTT GTAAAAGATG     720

GGGTTCCAAC AAAATAGAAG AAATATTTTC GATCCAAAAA AAAAA                     765

(2) INFORMATION FOR SEQ ID NO:12:

(i) SEQUENCE CHARACTERISTICS:
        (A) LENGTH: 453 base pairs
        (B) TYPE: nucleic acid
        (C) STRANDEDNESS: single
        (D) TOPOLOGY: linear (xi) SEQUENCE DESCRIPTION: SEQ ID NO:12:

TGATTATGCG GATCCTTGGG CAGGGATACG GCATGACAGA AGCAGGCCCG GTGCTGGCAA      60

TGAACCTAGC CTTCGCAAAG AATCCTTTCC CCGCCAAATC TGGCTCCTGC GGAACAGTCG     120

TCCGGAACGC TCAAATAAAG ATCCTCGATT ACAGGAACTG GCGAGTCTCT CCCGCACAAT     180

CAAGCCGGCG AAATCTGCAT CCGCGGACCC GAAATAATGA AAGGATATAT TAACGACCCG     240

GAATCCACGG CCGCTACAAT CGATGAAGAA GGCTGGCTCC ACACAGGCGA CGTCGGGTAC     300

ATTGACGATG ACGAAGAAAT CTTCATAGTC GACAGAGTAA AGGAGATTAT CAATATAAAG     360

GCTTCCAGGT GGATCCTGCT AATCGAATTC CTGCAGCCCG GGGGTCCACT AGTTCTAGAG     420

CGGCCGCCAC CGCGGTGGAG CTCCAGCTTT TGT                                  453
```

(2) INFORMATION FOR SEQ ID NO:13:

(i) SEQUENCE CHARACTERISTICS:
        (A) LENGTH: 278 base pairs
        (B) TYPE: nucleic acid
        (C) STRANDEDNESS: single
        (D) TOPOLOGY: linear (xi) SEQUENCE DESCRIPTION: SEQ ID NO:13:

```
TCTTCGAATT CTCTTTCACG ACTGCTTCGT TAATGGCTGC GATGGCTCGA TATTGTTAGA      60

TGATAACTCA ACGTTCACCG GAGAAAAGAC TGCAGGCCCA AATGTTAATT CTGCGAGAGG     120

ATTCGACGTA ATAGACACCA TCAAAACTCA AGTTGAGGCA GCCTGCAGTG GTGTCGTGTC     180

AGTTGCCGAC ATTCTCGCCA TTGCTGCACG CGATTCAGTC GTCCAACTGG GGGGCCCAAC     240

ATGGACGGTA CTTCTGGGAG AAAAGACGGA TCCGATCA                             278
```

(2) INFORMATION FOR SEQ ID NO:14:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:14:

```
CTTCGAATTC WYTTYCAYGA YTG                                             23
```

(2) INFORMATION FOR SEQ ID NO:15:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:15:

```
GATCGGATCC RTCYYKYCTY CC                                              22
```

(2) INFORMATION FOR SEQ ID NO:16:

(i) SEQUENCE CHARACTERISTICS:
        (A) LENGTH: 472 base pairs
        (B) TYPE: nucleic acid
        (C) STRANDEDNESS: single
        (D) TOPOLOGY: linear (xi) SEQUENCE DESCRIPTION: SEQ ID NO:16:

```
AATTCGGCAC GAGACGACCT CTTGTATCGG ACCCGGATCC GCTATCGTTA ACGTACACAC      60

GTTCTAGTGC TGAATGGAGA TGGAGAGCAC CACCGGCACC GGCAACGGCC TTCACAGCCT     120

CTGCGCCGCC GGGAGCCACC ATGCCGACCC ACTGAACTGG GGGGCGGCGG CAGCAGCCCT     180

CACAGGGAGC CACCTCGACG AGGTGAAGCG GATGGTCGAG GAGTACCGGA GGCCGGCGGT     240

GCGCCTCGGC GGGGAGTCCC TCACGATAGC CCAGGTGGCG GCGGTGGCGA GTCAGGAGGG     300

GGTAGGGGTC GAGCTCTCGG AGGCGGCCCG TCCCAGGGTC AAGGCCAGCA GCGACTGGGT     360

CATGGAGAGC ATGAACAAGG GAACTGCACA CTACGGGGTC ACCACCGGGT TCGGCGGCAA     420

CTTCTCAAAC CGGAGGCCGA AGCAAGGCGG TCCTTTTCAG AAGGAACTTA TA            472
```

(2) INFORMATION FOR SEQ ID NO:17:

(i) SEQUENCE CHARACTERISTICS:
        (A) LENGTH: 622 base pairs
        (B) TYPE: nucleic acid (C) STRANDEDNESS: single
        (D) TOPOLOGY: linear (xi) SEQUENCE DESCRIPTION: SEQ ID NO:17:

CCAAAGCTCC TAGTGCCTCA TGAGTCTGCT GAGGATTGCA CAATTGGCGG GTTCGACGTG      60

CCCCGAGGCA CCATGATCCT GGTTAATGCG TGGGCAATTC AAAGAGACCC AAAAGTGTGG     120

GACGATCCCA CAAATTTTAA ACCGGAGAGG TACGAGGGAT TGGAAGGTGA TCATGCCTAC     180

CGACTATTGC CGTTTGGGAT GGGGAGGAGA AGTTGTCCTG GTGCTGGCCT TGCCAATAGA     240

GTGGTGAGCT TGGTCCTGGC GGCGCTTATT CAGTGCTTCG AATGGGAACG AGTTGGCGAA     300

GAATTGGTGG ACTTGTCCGA GGGGACGGGA CTCACAATGC AAAGAGAGA GCCATTGGAG      360

GCCTTGTGCA AAGCGCGTGA ATGCATGATA GCTAATGTTC TTGCGCACCT TTAAGAAGGT     420

CGTTGTCTAA TGAATTTACA TTGGTGATGT ATCTCCAATG TTTTTGAATA ATCAAATAGA     480

CTGAAAATAG GCCAGTGCAG CTTTAGGAAT GATCGTGAGC ATCAATAGCA TCCTGAGGAG     540

GCCAATGCAG CTTTAGGCCT TTCTCTTAGG AGAAAAATGA TGGTTTATAT AGGTACTGGC     600

AACATTGTTC AAAAAAAAAA AA                                             622

(2) INFORMATION FOR SEQ ID NO:18:

(i) SEQUENCE CHARACTERISTICS:
        (A) LENGTH: 414 base pairs
        (B) TYPE: nucleic acid
        (C) STRANDEDNESS: single
        (D) TOPOLOGY: linear (xi) SEQUENCE DESCRIPTION: SEQ ID NO:18:

CACGCTCGAC GAATTCGGTA CCCCGGGTTC GAAATCGATA AGCTTGGATC CAAAGCAACA      60

CATTGAACTC TCTCTCTCTC TCTCTCTCTC TCTCTCTCTC TCCCCCACCC CCCCTTCCCA     120

ACCCCACCCA CATACAGACA AGTAGATACG CGCACACAGA AGAAGAAAAG ATGGGGGTTT     180

CAATGCAGTC AATCGCACTA GCGACGGTTC TGGCCGTCCT AACGACATGG GCGTGGAGGG     240

CGGTGAACTG GGTGTGGCTG AGGCCGAAGA GGCTCGAGAG GCTTCTGAGA CAGCAAGGTC     300

TCTCCGGCAA GTCCTACACC TTCCTGGTCG GCGACCTCAA GGAGAACCTG CGGATGCTCA     360

AGGAAGCCAA GTCCAAGCCC ATCGCCGTCT CCGATGACAT CAAGCCTCGT CTCT           414

(2) INFORMATION FOR SEQ ID NO:19:

(i) SEQUENCE CHARACTERISTICS:
        (A) LENGTH: 469 base pairs
        (B) TYPE: nucleic acid
        (C) STRANDEDNESS: single
        (D) TOPOLOGY: linear (xi) SEQUENCE DESCRIPTION: SEQ ID NO:19:

GAATTCGGCA CGAGTGTCTC TCTCTCTCTC TCTCTCTGTA AACCACCATG CTCTTCCTCA      60

CTCATCTCCT AGCAGTTCTA GGGGTTGTGT TGCTCCTGCT AATTCTATGG AGGGCAAGAT     120

CTTCTCCGAA CAAACCCAAA GGTACTGCCT TACCCCCGGA GCTGCCGGGC GCATGGCCGA     180

TCATAGGCCA CATCCACTTG CTGGGCGGCG AGACCCCGCT GGCCAGGACC CTGGCCGCCA     240

TGGCGGACAA GCAGGGCCCG ATGTTTCGGA TCCGTCTCGG AGTCCACCCG GCGACCATCA     300

TAAGCAGCCG TGAGGCGGTC CGGGAGTGCT TCACCACCCA CGACAAGGAC CTCGCTTCTC     360

GCCCCAAATC CAAGGCGGGA ATCCACTTGG GCTACGGGTA TGCCGGTTTT GGCTTCGTAG     420

AATACGGGGA CTTTTGGCGC GAGATGAGGA AGATCACCAT GCTCGAGCT                 469

(2) INFORMATION FOR SEQ ID NO:20:

(i) SEQUENCE CHARACTERISTICS:
        (A) LENGTH: 341 base pairs
        (B) TYPE: nucleic acid
        (C) STRANDEDNESS: single
        (D) TOPOLOGY: linear (xi) SEQUENCE DESCRIPTION: SEQ ID NO:20:

```
CGGGCTCGTG GCTCGGCTCC GGCGCAACGC CCTTCCCACC GGGCCCGAGG GGCCTCCCGG      60
TCATCGGGAA CATGCTCATG ATGGGCGAGC TCACCCACCG CGGCCTCGCG AGTCTGGCGA     120
AGAAGTATGG CGGGATCTTC CACCTCCGCA TGGGCTTCCT GCACATGGTT GCCGTGTCGT     180
CCCCCGACGT GGCCCGCCAG GTCCTCCAGG TCCACGACGG GATCTTCTCG AACCGGCCTG     240
CCACCATCGC GATCAGCTAC CTCACGTATG ACCGGGCCGA CATGGCCTTC GCGCACTACG     300
GCCCGTTCTG GCGGCAGATG CGGAAGCTGT GCGTGATGAA A                         341
```

(2) INFORMATION FOR SEQ ID NO:21:

(i) SEQUENCE CHARACTERISTICS:
        (A) LENGTH: 387 base pairs
        (B) TYPE: nucleic acid
        (C) STRANDEDNESS: single
        (D) TOPOLOGY: linear (xi) SEQUENCE DESCRIPTION: SEQ ID NO:21:

```
GAATTCGGCA CGAGCGGGCT CGTGGCTCGG CTCCGGCGCA ACGCCCTTCC CACCGGGCCC      60
GAGGGGCCTC CCGGTCATCG GGAACATGCT CATGATGGGC GAGCTCACCC ACCGCGGCCT     120
CGCGAGTCTG GCGAAGAAGT ATGGCGGGAT CTTCCACCTC CGCATGGGCT TCCTGCACAT     180
GGTTGCCGTG TCGTCCCCCG ACGTGGCCCG CCAGGTCCTC CAGGTCCACG ACGGGATCTT     240
CTCGAACCGG CCTGCCACCA TCGCGATCAG CTACCTCACG TATGACCGGG CCGACATGGC     300
CTTCGCGCAC TACGGCCCGT TCTGGCGGCA GATGCGGAAG CTGTGCGTGA TGAAAGCTCT     360
TCAGCGGAAG CGGGCTGAGT CGTGGGA                                         387
```

(2) INFORMATION FOR SEQ ID NO:22:

(i) SEQUENCE CHARACTERISTICS:
        (A) LENGTH: 443 base pairs
        (B) TYPE: nucleic acid
        (C) STRANDEDNESS: single
        (D) TOPOLOGY: linear (xi) SEQUENCE DESCRIPTION: SEQ ID NO:22:

```
CACGAGCTCG TGAGCCTTCC CGGAGACAAG GCCATCTTAC TTCGCAACAA ATTGCGTCCG      60
CACTCCTTTC TCAAGAAACC TAGTCATCCA AGAAGCAGAG CATTGCAACT GCAAACAGCC     120
AAAGCCCAAA CTCGTACAGA AGGAGAGAGA GAGAGAGAAT AGAAGCATGA GTGCATGCAC     180
GAACCAAGCA ATCACGACGG CCAGTGAAGA TGAAGAGTTC TTGTTCGCCA TGGAAATGAA     240
TGCTCTGATA GCACTCCCCT TGGTCTTGAA GGCCACCATC GAACTGGGGA TCCTCGAAAT     300
ACTGGCCGAG TGCGGGCCTA TGGCTCCACT TTCGCCTGCT CAGATTGCCT CCCGTCTCTC     360
CGCAAAGAAC CCGGAAGCCC CCGTAACCCT TGACCGGATC CTCCGGTTTC TCGCCAGCTA     420
CTCCATCCTC TCTTGCACTC TCG                                             443
```

(2) INFORMATION FOR SEQ ID NO:23:

(i) SEQUENCE CHARACTERISTICS:
        (A) LENGTH: 607 base pairs
        (B) TYPE: nucleic acid (C) STRANDEDNESS: single
(D) TOPOLOGY: linear (xi) SEQUENCE DESCRIPTION: SEQ ID NO:23:

| | | | | | |
|---|---|---|---|---|---|
| GAATTCGGCA | CGAGCCAACC | CTGGACCAGG | TACTTTTGGC | AGGCGGTCCA | TTGCCCTTCA | 60 |
| AACCGGTCCA | AACCGGACCA | TCACTGTCCT | TATATACGTT | GCATCATGCC | TGCTCATAGA | 120 |
| ACTTAGGTCA | ACTGCAACAT | TTCTTGATCA | CAACATATTA | CAATATTCCT | AAGCAGAGAG | 180 |
| AGAGAGAGAG | AGAGAGAGAG | AGAGAGAGAG | AGAGTTTGAA | TCAATGGCCA | CCGCCGGAGA | 240 |
| GGAGAGCCAG | ACCCAAGCCG | GGAGGCACCA | GGAGGTTGGC | CACAAGTCTC | TCCTTCAGAG | 300 |
| TGATGCTCTT | TACCAATATA | TTTTGGAGAC | CAGCGTGTAC | CCAAGAGAGC | CTGAGCCCAT | 360 |
| GAAGGAGCTC | AGGGAAATAA | CAGCAAAACA | TCCATGGAAC | ATAATGACAA | CATCAGCAGA | 420 |
| CGAAGGGCAG | TTCTTGAACA | TGCTTCTCAA | GCTCATCAAA | GCCAAGAACA | CCATGGAGAT | 480 |
| TGGTGTCTTC | ACTGGCTACT | CTCTCCTCGC | CACCGCTCTT | GCTCTTCCTG | ATGACGGAAA | 540 |
| GATTTTGGCT | ATGGACATTA | ACAGAGAGAG | CTATGAACTT | GGCCTGCCGG | CATCCAAAAA | 600 |
| GCCGGTG | | | | | | 607 |

(2) INFORMATION FOR SEQ ID NO:24:

(i) SEQUENCE CHARACTERISTICS:
       (A) LENGTH: 421 base pairs
       (B) TYPE: nucleic acid
       (C) STRANDEDNESS: single
       (D) TOPOLOGY: linear (xi) SEQUENCE DESCRIPTION: SEQ ID NO:24:

| | | | | | |
|---|---|---|---|---|---|
| GAATTCGGCA | CGAGCCGTTT | TATTTCCTCT | GATTTCCTTT | GCTCGAGTCT | CGCGGAAGAG | 60 |
| AGAGAAGAGA | GGAGAGGAGA | GAATGGGTTC | GACCGGATCC | GAGACCCAGA | TGACCCCGAC | 120 |
| CCAAGTCTCG | GACGAGGAGG | CGAACCTCTT | CGCCATGCAG | CTGGCGAGCG | CCTCCGTGCT | 180 |
| CCCCATGGTC | CTCAAGGCCG | CCATCGAGCT | CGACCTCCTC | GAGATCATGG | CCAAGGCCGG | 240 |
| GCCGGGCGCG | TTCCTCTCCC | CGGGGGAAGT | CGCGGCCCAG | CTCCCGACCC | AGAACCCCGA | 300 |
| GGCACCCGTA | ATGCTCGACC | GGATCTTCCG | GCTGCTGGCC | AGCTACTCCG | TGCTCACGTG | 360 |
| CACCCTCCGC | GACCTCCCCG | ATGGCAAGGT | CGAGCGGCTC | TACGGCTTAG | CGCCGGTGTG | 420 |
| C | | | | | | 421 |

(2) INFORMATION FOR SEQ ID NO:25:

(i) SEQUENCE CHARACTERISTICS:
       (A) LENGTH: 760 base pairs
       (B) TYPE: nucleic acid
       (C) STRANDEDNESS: single
       (D) TOPOLOGY: linear (xi) SEQUENCE DESCRIPTION: SEQ ID NO:25:

| | | | | | |
|---|---|---|---|---|---|
| GGAAGAAGCC | GAGCAAACGA | ATTGCAGACG | CCATTGAAAA | AAGACACGAA | AGAGATCAAG | 60 |
| AAGGAGCTTA | AGAAGCATCA | TCAATGGCAG | CCAACGCAGA | GCCTCAGCAG | ACCCAACCAG | 120 |
| CGAAGCATTC | GGAAGTCGGC | CACAAGAGCC | TCTTGCAGAG | CGATGCTCTC | TACCAGTATA | 180 |
| TATTGGAGAC | CAGCGTCTAC | CCAAGAGAGC | CAGAGCCCAT | GAAGGAGCTC | AGGGAAATAA | 240 |
| CAGCCAAACA | TCCATGGAAC | CTGATGACCA | CATCGGCGGA | TGAAGGGCAG | TTCCTGAACA | 300 |
| TGCTCCTCAA | GCTCATCAAC | GCCAAGAACA | CCATGGAGAT | CGGCGTCTAC | ACCGGCTACT | 360 |
| CTCTCCTCGC | AACCGCCCTT | GCTCTTCCCG | ATGACGGAAA | GATCTTGGCC | ATGGCCATCA | 420 |
| ATAGGGAGAA | CTTCGAGATC | GGGCTGCCCG | TCATCCAGAA | GGCCGGCCTT | GCCCACAAGA | 480 |

TCGATTTCAG AGAAGGCCCT GCCCTGCCGC TCCTTGATCA GCTCGTGCAA GATGAGAAGA    540

ACCATGGAAC GTACGACTTC TTCTCAATCC TTAATCGTTC ATTTGAATAC AAATACATGC    600

TCAATGGTTC AAAGACAACA TAAGACAGAA GATGGAAAAA ATAGAAAGGA AGGAAAGTAT    660

TAAGGGTAGT TTCTCATTTC ATCAATGCTT GATTTTGAGA TCTCCTTTCT GGTGCGATCA    720

GCTGACCCGG CGGCACAGGT GATGCCATCC CCGACGGGAA                          760

(2) INFORMATION FOR SEQ ID NO:26:

(i) SEQUENCE CHARACTERISTICS:
        (A) LENGTH: 508 base pairs
        (B) TYPE: nucleic acid
        (C) STRANDEDNESS: single
        (D) TOPOLOGY: linear (xi) SEQUENCE DESCRIPTION: SEQ ID NO:26:

GAATTCGGTA CCCGGGTTCG AAATCGATAA GCTTGGATCC AAAGAATTCG GCACGAGATC     60

ACTAACCATC TGCCTTTCTT CATCTTCTTT CTTCTGCTTC TCCTCCGTTT CCTCGTTTCG    120

ATATCGTGAA AGGAGTCCGT CGACGACAAT GGCCGAGAAG AGCAAGGTCC TGATCATCGG    180

AGGGACGGGC TACGTCGGCA AGTTCATCGT GGAAGCGAGT GCAAAAGCAG GCATCCCAC     240

GTTCGCGCTG GTTAGGCAGA GCACGGTCTC CGACCCCGTC AAGGGCCAGC TCGTCGAGAG    300

CTTCAAGAAC TTGGGCGTCA CTCTGCTCAT CGGTGATCTG TACGATCATG AGAGCTTGGT    360

GAAGGCAATC AAGCAAGCCG ACGTGGTGAT ATCGACAGTG GGGCACATGC AAATGGCGGA    420

TCAGACCAAA GAATCGTCGA CGCCATTAAA GGAAGCTGGC AACGTTAAGG TTTGTTGGTT    480

GGTTCATTTG ATCTGGTTTG GGGGGGTC                                       508

(2) INFORMATION FOR SEQ ID NO:27:

(i) SEQUENCE CHARACTERISTICS:
        (A) LENGTH: 495 base pairs
        (B) TYPE: nucleic acid
        (C) STRANDEDNESS: single
        (D) TOPOLOGY: linear (xi) SEQUENCE DESCRIPTION: SEQ ID NO:27:

GAATTCGGCA CGAGGTTAAT GGCAGTGCAG CCTCAACACC ACCCACCTTC CTCCATCTCT     60

CTCCTCCCTT CTTCTTTCTC TGACTTCAAT GGCAGCCGAC TCCATGCTTG CGTTCAGTAT    120

AAGAGGAAGG TGGGGCAGCC TAAAGGGGCA CTGCGGGTCA CTGCATCAAG CAATAAGAAG    180

ATCCTCATCA TGGGAGGCAC CCGTTTCATC GGTGTGTTTT TGTCGAGACT ACTTGTCAAA    240

GAAGGTCATC AGGTCACTTT GTTTACCAGA GGAAAAGCAC CCATCACTCA ACAATTGCCT    300

GGTGAGTCGG ACAAGGACTT CGCTGATTTT TCATCCAAGA TCCTGCATTT GAAAGGAGAC    360

AGAAAGGATT TGATTTTGT TAAATCTAGT CTTGCTGCAG AAGGCTTTGA CGTTGTTTAT    420

GACATTAACG GCGAGAGGCG GATGAAGTCG CACCAATTTT GGATGCCTGC CAAACCTTGA    480

ACCAGTCAAC TACTG                                                     495

(2) INFORMATION FOR SEQ ID NO:28:

(i) SEQUENCE CHARACTERISTICS:
        (A) LENGTH: 472 base pairs
        (B) TYPE: nucleic acid
        (C) STRANDEDNESS: single
        (D) TOPOLOGY: linear (xi) SEQUENCE DESCRIPTION: SEQ ID NO:28:

```
GAATTCGGCA CGAGCATAAG CTCTCCCGTA ATCCTCACAT CACATGGCGA AGAGCAAGGT      60

CCTCGTCGTT GGCGGCACTG GCTACCTCGG GCGGAGGTTC GTGAGGGCGA GCCTGGACCA     120

GGGCCACCCC ACGTACGTCC TCCAGCGTCC GGAGACCGGC CTCGACATTG AGAAGCTCCA     180

GACGCTACTG CGCTTCAAGA GGCGTGGCGC CCAACTCGTC GAGGCCTCGT TCTCAGACCT     240

GAGGAGCCTC GTCGACGCTG TGAGGCGGGT CGATGTCGTC GTCTGTGCCA TGTCGGGGGT     300

CCACTTCCGG AGCCACAACA TCCTGATGCA GCTCAAGCTC GTGGAGGCTA TCAAAGAAGC     360

TGGAAATGTC AAGCGGTTTT TGCCGTCAGA GTTCGGAATG GACCCGGCCC TCATGGGTCA     420

TGCAATTGAG CCGGGAAGGG TCACGTTCGA TGAGAAATGG AGGTGAGAAA AG            472
```

(2) INFORMATION FOR SEQ ID NO:29:

(i) SEQUENCE CHARACTERISTICS:
        (A) LENGTH: 396 base pairs
        (B) TYPE: nucleic acid
        (C) STRANDEDNESS: single
        (D) TOPOLOGY: linear (xi) SEQUENCE DESCRIPTION: SEQ ID NO:29:

```
GAATTCGGCA CGAGGAGGCA CCTCCTCGAA ACGAAGAAGA AGAAGGACGA AGGACGAAGG      60

AGACGAAGGC GAGAATGAGC GCGGCGGGCG GTGCCGGGAA GGTCGTGTGC GTGACCGGGG     120

CGTCCGGTTA CATCGCCTCG TGGCTCGTCA AGCTCCTCCT CCAGCGCGGC TACACCGTCA     180

AGGCCACCGT CCGCGATCCG AATGATCCAA AAAAGACTGA ACATTTGCTT GGACTTGATG     240

GAGCGAAAGA TAGACTTCAA CTGTTCAAAG CAAACCTGCT GGAAGAGGGT TCATTTGATC     300

CTATTGTTGA GGGTTGTGCA GGCGTTTTTC AAACTGCCTC TCCCTTTTAT CATGATGTCA     360

AGGATCCGCA GGCAGAATTA CTTGATCCGG CTGTAA                              396
```

(2) INFORMATION FOR SEQ ID NO:30:

(i) SEQUENCE CHARACTERISTICS:
        (A) LENGTH: 592 base pairs
        (B) TYPE: nucleic acid
        (C) STRANDEDNESS: single
        (D) TOPOLOGY: linear (xi) SEQUENCE DESCRIPTION: SEQ ID NO:30:

```
GAATTCGGCA CGAGGTTGAA CCTCCCGTCC TCGGCTCTGC TCGGCTCGTC ACCCTCTTCG      60

CGCTCCCGCA TACTCCACCA CCGCGTACAG AAGATGAGCT CGGAGGGTGG GAAGGAGGAT     120

TGCCTCGGTT GGGCTGCCCG GGACCCTTCT GGGTTCCTCT CCCCCTACAA ATTCACCCGC     180

AGGGCCGTGG GAAGCGAAGA CGTCTCGATT AAGATCACGC ACTGTGGAGT GTGCTACGCA     240

GATGTGGCTT GGACTAGGAA TGTGCAGGGA CACTCCAAGT ATCCTCTGGT GCCAGGGCAC     300

GAGATAGTTG GAATTGTGAA ACAGGTTGGC TCCAGTGTCC AACGCTTCAA AGTTGGCGAT     360

CATGTGGGGG TGGGAACTTA TGTCAATTCA TGCAGAGAGT GCGAGTATTG CAATGACAGG     420

CTAGAAGTCC AATGTGAAAA GTCGGTTATG ACTTTTGATG GAATTGATGC AGATGGTACA     480

GTGACAAAGG GAGGATATTC TAGTCACATT GTCGTCCATG AAAGGTATTG CGTCAGGATT     540

CCAGAAAACT ACCCGATGGA TCTAGCAGCG CATTTGCTCT GTGCTGGATC AC            592
```

(2) INFORMATION FOR SEQ ID NO:31:

(i) SEQUENCE CHARACTERISTICS:
        (A) LENGTH: 468 base pairs
        (B) TYPE: nucleic acid
        (C) STRANDEDNESS: single
        (D) TOPOLOGY: linear (xi) SEQUENCE DESCRIPTION: SEQ ID NO:31:

```
GAATTCGGCA CGAGAACTCA TCTTGAAATG TCATTGGAGT CATCATCCTC TAGTGAGAAG        60

AAACAAATGG GTTCCGCCGG ATTCGAATCG GCCACAAAGC CGCACGCCGT TTGCATTCCC       120

TACCCTGCAC AAAGCCACAT TGGCGCCATG CTCAAGCTAG CAAAGCTCCT CCATCACAAG       180

GGCTTCCACA TCTCCTTCGT CAACACCGAG TTCAACCACC GGCGGCTCGC CAGGGCTCGA       240

GGCCCCGAGT TCACAAATGG AATGCTGAGC GACTTTCAGT TCCTGACAAT CCCCGATGGT       300

CTTCCTCCTT CGGACTTGGA TGCGATCCAA GACATCAAGA TGCTCTGCGA ATCGTCCAGG       360

AACTATATGG TCAGCCCCAT CAACGATCTT GTATCGAGCC TGGGCTCGAA CCCGAGCGTC       420

CCTCCGGTGA CTTGCATCAA TCTCGGATGG TTTCATGACA CTCGTGAC                   468
```

(2) INFORMATION FOR SEQ ID NO:32:

(i) SEQUENCE CHARACTERISTICS:
        (A) LENGTH: 405 base pairs
        (B) TYPE: nucleic acid
        (C) STRANDEDNESS: single
        (D) TOPOLOGY: linear (xi) SEQUENCE DESCRIPTION: SEQ ID NO:32:

```
CTTTACTCCG CCAAGAAGAT CCAATCGCAG TTTTCGCAAT TGGCCCATTA CACAAATGCG        60

GTCCATCTTC ATCGGGAAGT CTCTTGGCAG AAGACCGGAG TTGCATTTCC TGGCTGGACA       120

AGCAAGCCCC TAACTCAGTG GTCTATGTGA GTCTTGGGCA CATCGCCTCT GTGAACGAGT       180

CGGAATTTTC CGAAATAGCT TTAGGTTTAG CCGATAGCCA GCAGCCATTC TTGTGGGTGG       240

TTCGACCCGG GTCAGTGAGC GGCTCGGAAC TCTTAGAGAA TTTGCCCGGT TGCTTTCTGG       300

AGGCATTACA GGAGAGGGGG AAGATTGTGA ATGGGCGCC TCAACATGAA GTGCTGGCTC       360

ATCGGGCTGT CGGAGCGTTT TGGACTCACA ATGGATGGAA CTCCA                      405
```

(2) INFORMATION FOR SEQ ID NO:33:

(i) SEQUENCE CHARACTERISTICS:
        (A) LENGTH: 380 base pairs
        (B) TYPE: nucleic acid
        (C) STRANDEDNESS: single
        (D) TOPOLOGY: linear (xi) SEQUENCE DESCRIPTION: SEQ ID NO:33:

```
GGCAAACACG CCCGTTTTCG TTTTACTAAG AGAAGATGGT GAGCGTTGTG GCTGGTAGAG        60

TCGAGAGCTT GTCGAGCAGT GGCATTCAGT CGATCCCGCA GGAGTATGTG AGGCCGAAGG       120

AGGAGCTCAC AAGCATTGGC GACATCTTCG AGGAGGAGAA GAAGCATGAG GGCCCTCAGG       180

TCCCGACCAT CGACCTCGAG GACATAGCGT CTAAAGACCC CGTGGTGAGG GAGAGGTGCC       240

ACGAGGAGCT CAGGAAGGCT GCCACCGACT GGGGCGTCAT GCACCTCGTC AACCATGGGA       300

TCCCCAACGA CCTGATTGAG CGTGTAAAGA AGGCTGGCGA GGTGTTCTTC AACCTCCCGA       360

TCGAGGAGAA GGACAAGCAT                                                   380
```

(2) INFORMATION FOR SEQ ID NO:34:

(i) SEQUENCE CHARACTERISTICS:
        (A) LENGTH: 305 base pairs
        (B) TYPE: nucleic acid
        (C) STRANDEDNESS: single
        (D) TOPOLOGY: linear (xi) SEQUENCE DESCRIPTION: SEQ ID NO:34:

```
TTGTACCCGA AGATCTCCGG GACCGTTCGA CGGCGACATC GCCGTCGGCC GGGAACCCGT      60

CGAGGCCGCC GCCGGAGGCC GGGGAGAAGC TGGAGTAGCC GCCGTAGCCG GAGAAGGCGC     120

CGTCGTGGTC GGCGGCGGCG GCGTGGTGGA CCTCATCGCC GTCCATGCTG AAGGCGTCGA     180

AGGAAGCGGA CATGGCTGGG GGATCGATCG ACCGATCCGA TCGGCCGGAG GATTTCGAGA     240

TCGGAGATGG AGAGATGGAA ATGAAAGAGA GAGAGAGAGA GAGATCCGGT GGACTGGTGG     300

TGTTT                                                                 305

(2) INFORMATION FOR SEQ ID NO:35:

(i) SEQUENCE CHARACTERISTICS:
        (A) LENGTH: 693 base pairs
        (B) TYPE: nucleic acid
        (C) STRANDEDNESS: single
        (D) TOPOLOGY: linear (xi) SEQUENCE DESCRIPTION: SEQ ID NO:35:

GAATTCGGCA CGAGCTAAGA GAGGAGAGGA GAGGAGCAAG ATGGCACTAG CAGGAGCTGC      60

ACTGTCAGGA ACCGTGGTGA GCTCCCCCTT TGTGAGGATG CAGCCTGTGA ACAGACTCAG     120

GGCATTCCCC AATGTGGGTC AGGCCCTGTT TGGTGTCAAC TCTGGCCGTG GCAGAGTGAC     180

TGCCATGGCC GCTTACAAGG TCACCCTGCT CACCCCTGAA GGCAAAGTCG AACTCGACGT     240

CCCCGACGAT GTTTACATCT TGGACTACGC CGAGGAGCAA GGCATCGACT TGCCCTACTC     300

CTGCCGTGCC GGCTCTTGCT CCTCCTGCGC GGGCAAGGTC GTGGCGGGGA GCGTCGACCA     360

GAGCGACGGC AGCTTCCTGG ATGATGATCA GATTGAGGAA GGTTGGGTCC TCACTTGTGT     420

CGCCTACCCT AAGTCTGAGG TCACCATTGA GACCCACAAG GAAGAGGAGC TCACTGCTTG     480

AAGCTCTCCT ATATTTGCTT TTGCATAAAT CAGTCTCACT CTACGCAACT TTCTCCACTC     540

TCTCCCCCCT TCACTACATG TTTGTTAGTT CCTTTAGTCT CTTCCTTTTT TACTGTACGA     600

GGGATGATTT GATGTTATTC TGAGTCTAAT GTAATGGCTT TCTTTTTCC TATTTCTGTA      660

TGAGGAAATA AAACTCATGC TCTAAAAAAA AAA                                  693

(2) INFORMATION FOR SEQ ID NO:36:

(i) SEQUENCE CHARACTERISTICS:
        (A) LENGTH: 418 base pairs
        (B) TYPE: nucleic acid
        (C) STRANDEDNESS: single
        (D) TOPOLOGY: linear (xi) SEQUENCE DESCRIPTION: SEQ ID NO:36:

AGGACTTTAT TATAAGCATT GTAAAAAGAG TCAAACTAAT ACATCGCAAG AATTGGGTTA      60

TCCAATAATC TACAAAAAGA AAAAGTTTG ATGCATTGAG ATGGTAACTG CTTAATTCAA      120

ATGCCTTAGT TTGAAAAATT AACCAACTAT TAAAATTAAT GATGATGAAT ATGGATTATG     180

TGTGAAAAAC TATATAGACT TAAAATTGAC TCAGAAGACA TTCTTTTCTT CTTATTTTAT     240

GATATGATGA ATTCGGTCTA AACAGGCAAA TGGTGTCAAA CGGGAAGTCG GCAAAACTCT     300

TCCTCGGCAG TGACTACCGG GCGGGCGATG ATGCGGATCC GGGGGCCGGG TCGCTGGAGA     360

ACATCCCGCA CGGACCGGTC CACGTTTGGT GCGGTGACAA CAGGCAGCCC AACCTGGA      418

(2) INFORMATION FOR SEQ ID NO:37:

(i) SEQUENCE CHARACTERISTICS:
        (A) LENGTH: 777 base pairs
        (B) TYPE: nucleic acid
        (C) STRANDEDNESS: single
        (D) TOPOLOGY: linear
```

(xi) SEQUENCE DESCRIPTION: SEQ ID NO:37:

```
GAATTCGGCA CGAGCATACA ACTACACTGC GACGCCGCCG CAGAACGCGA GCGTGCCGAC         60

CATGAACGGC ACCAAGGTCT ACCGGTTGCC GTATAACGCT ACGGTCCAGC TCGTTTTACA        120

GGACACCGGG ATAATCGCGC CGGAGACCCA CCCCATCCAT CTGCACGGAT TCAACTTCTT        180

CGGTGTGGGC AAAGGAGTGG GGAATTATGA CCCAAAGAAG GATCCCAAGA AGTTCAATCT        240

GGTTGACCCA GTGGAGAGGA ACACCATTGG AATCCCATCT GGTGGATGGA TAGCCATCAG        300

ATTCACAGCA GACAATCCAG GAGTTTGGTT CCTGCACTGC CATCTGGAAG TGCACACAAC        360

TTGGGGACTG AAGATGGCAT TCTTGGTGGA CAATGGGAAG GGGCCTAAAG AGACCCTGCT        420

TCCACCTCCA AGTGATCTTC CAAAATGTTG ATCATTTGAT CATGAGGACG ACAAGCGATT        480

ACTAATGACA CCAAGTTAGT GGAATCTTCT CTTTGAAAAA GAAGAAGAAG AGCAAGAAGA        540

ATAAGAAAGA TGAGGAGAGA AGCCATAGAA GATTTGACCA AGAAGAGAGA GGGCAATAAA        600

CCAAAGAGAC CCTTGAGATC ACGACATCCC GCAATTGTTT CTAGAGTAAT AGAAGGATTT        660

ACTCCGACAC TGCTACAATA AATTAAGGAA GACAAGGAAT TTGGTTTTTT TCATTGGAGG        720

AGTGTAATTT GTTTTTTGGC AAGCTCATCA CATGAATCAC ATGGAAAAAA AAAAAAA          777
```

(2) INFORMATION FOR SEQ ID NO:38:

(i) SEQUENCE CHARACTERISTICS:
        (A) LENGTH: 344 base pairs
        (B) TYPE: nucleic acid
        (C) STRANDEDNESS: single
        (D) TOPOLOGY: linear (xi) SEQUENCE DESCRIPTION: SEQ ID NO:38:

```
ATATGTTCAG AATTTCAAAT GTGGGAATGT CAACCTCCTT GAACTTCAGA ATTCAGGGCC         60

ATACGTTGAA GCTAGTCGAG GTTGAAGGAT CTCACACCGT CCAGAACATG TATGATTCAA        120

TCGATGTTCA CGTGGGCCAA TCCATGGCTG TCTTAGTGAC CTTAAATCAG CCTCCAAAGG        180

ACTACTACAT TGTCGCATCC ACCCGGTTCA CCAAGACGGT TCTCAATGCA ACTGCAGTGC        240

TACACTACAC CAACTCGCTT ACCCCAGTTT CCGGGCCACT ACCAGCTGGT CCAACTTACC        300

AAAAACATTG GTCCATGAAG CAAGCAAGAA CAATCAGGTG GAAC                        344
```

(2) INFORMATION FOR SEQ ID NO:39:

(i) SEQUENCE CHARACTERISTICS:
        (A) LENGTH: 341 base pairs
        (B) TYPE: nucleic acid
        (C) STRANDEDNESS: single
        (D) TOPOLOGY: linear (xi) SEQUENCE DESCRIPTION: SEQ ID NO:39:

```
GCCGCAACTG CAATTCTCTT CGTAAAACAT GACGGCTGTC GGCAAAACCT CTTTCCTCTT         60

GGGAGCTCTC CTCCTCTTCT CTGTGGCGGT GACATTGGCA GATGCAAAAG TTTACTACCA        120

TGATTTTGTC GTTCAAGCGA CCAAGGTGAA GAGGCTGTGC ACGACCCACA ACACCATCAC        180

GGTGAACGGG CAATTCCCGG GTCCGACTTT GGAAGTTAAC GACGGCGACA CCCTCGTTGT        240

CAATGTCGTC AACAAAGCTC GCTACAACGT CACCATTCAC TGGCACGGCG TCCGGCAGGT        300

GAGATCTGGT TGGGCTGATG GGGCGGAATT TGTGACTCAA T                           341
```

(2) INFORMATION FOR SEQ ID NO:40:

(i) SEQUENCE CHARACTERISTICS:
        (A) LENGTH: 358 base pairs (B) TYPE: nucleic acid
        (C) STRANDEDNESS: single
        (D) TOPOLOGY: linear (xi) SEQUENCE DESCRIPTION: SEQ ID NO:40:

```
GAATTCGGCA CGAGATATGT TCAGAATTTC AAATGTGGGA ATGTCAACCT CCTTGAACTT        60

CAGAATTCAG GGCCATACGT TGAAGCTAGT CGAGGTTGAA GGATCTCACA CCGTCCAGAA       120

CATGTATGAT TCAATCGATG TTCACGTGGG CCAATCCATG GCTGTCTTAG TGACCTTAAA       180

TCAGCCTCCA AAGGACTACT ACATTGTCGC ATCCACCCGG TTCACCAAGA CGGTTCTCAA       240

TGCAACTGCA GTGCTACACT ACACCAACTC GCTTACCCCA GTTTCCGGGC CACTACCAGC       300

TGGTCCAACT TACCAAAAAC ATTGGTCCAT GAAGCAAGCA AGAACAATCA GGTGGAAC         358
```

(2) INFORMATION FOR SEQ ID NO:41:

(i) SEQUENCE CHARACTERISTICS:
        (A) LENGTH: 409 base pairs
        (B) TYPE: nucleic acid
        (C) STRANDEDNESS: single
        (D) TOPOLOGY: linear (xi) SEQUENCE DESCRIPTION: SEQ ID NO:41:

```
ATCAAGAGTT TGAGTCTAAA CCTTGTCTAA TCCTCTCTCG CATAGTCATT TGGAGACGAA        60

TGCTGATCGG CCGCAGCTGC ATTCTCTTCG TAAAACATGA CGGCTGTCGG CAAAACCTCT       120

TTCCTCTTGG GAGCTCTCCT CCTCTTCTCT GTGGCGGTGA CATTGGCAGA TGCAAAAGTT       180

TACTACCATG ATTTTGTCGT TCAAGCGACC AAGGTGAAGA GGCTGTGCAC GACCCACAAC       240

ACCATCACGG TGAACGGGCA ATTCCCGGGT CCGACTTTGG AAGTTAACGA CGGCGACACC       300

CTCGTTGTCA ATGTCGTCAA CAAAGCTCGC TACAACGTCA CCATTCACTG GCACGGCGTC       360

CGGCAGGTGA GATCTGGTTG GGCTGATGGG GCGGAATTTG TGACTCAAT                   409
```

(2) INFORMATION FOR SEQ ID NO:42:

(i) SEQUENCE CHARACTERISTICS:
        (A) LENGTH: 515 base pairs
        (B) TYPE: nucleic acid
        (C) STRANDEDNESS: single
        (D) TOPOLOGY: linear (xi) SEQUENCE DESCRIPTION: SEQ ID NO:42:

```
CTCTCTCTCT CTCTCTCTCT GTGTGTTCAT TCTCGTTGAG CTCGTGGTCG CCTCCCGCCA        60

TGGATCCGCA CAAGTACCGT CCATCCAGTG CTTTCAACAC TTCTTTCTGG ACTACGAACT       120

CTGGTGCTCC TGTCTGGAAC AATAACTCTT CGTTGACTGT TGGAAGCAGA GGTCCAATTC       180

TTCTTGAGGA TTATCACCTC GTGGAGAAAC TTGCCAACTT TGATAGGGAG AGGATTCCAG       240

AGCGTGTGGT GCATGCCAGA GGAGCCAGTG CAAAGGGATT CTTTGAGGTC ACTCATGACA       300

TTTCCCAGCT TACCTGTGCT GATTTCCTTC GGGCACCAGG AGTTCAAACA CCCGTGATTG       360

TCCGTTTCTC CACTGTCATC CACGAAAGGG GCAGCCCTGA AACCCTGAGG GACCCTCGAG       420

GTTTTGCTGT GAAGTTCTAC ACAAGAGAGG GTAACTTTGA TCTGGTGGGA AACAATTTCC       480

CTGTCTTCTT TGTCCGTAAT GGGATAAATT CCCCG                                  515
```

(2) INFORMATION FOR SEQ ID NO:43:

(i) SEQUENCE CHARACTERISTICS:
        (A) LENGTH: 471 base pairs
        (B) TYPE: nucleic acid
        (C) STRANDEDNESS: single
        (D) TOPOLOGY: linear (xi) SEQUENCE DESCRIPTION: SEQ ID NO:43:

```
GAATTCGGCA CGAGGCTCCC TCTCGTACTG CCATACTCCT GGGACGGGAT TCGGATAGGG      60

ATTTGCGGCG ATCCATTTCT CGATTCAAGG GGAAGAATCA TGGGGAAGTC CTACCCGACC     120

GTAAGCCAGG AGTACAAGAA GGCTGTCGAG AAATGCAAGA AGAAGTTGAG AGGCCTCATC     180

GCTGAGAAGA GCTGCGCTCC GCTCATGCTC CGCATCGCGT GGCACTCCGC CGGTACCTTC     240

GATGTGAAGA CGAAGACCGG AGGCCCGTTC GGGACCATGA AGCACGCCGC GGAGCTCAGC     300

CACGGGGCCA ACAGCGGGCT CGACGTTGCC GATCAGGTCT TGCAGCCGAT CAAGGATCAG     360

TTCCCCGTCA TCACTTATGC TGATTTCTAC CAGCTGGCTG GCGTCGTTGC TGTGGAAGTT     420

ACTGGTGGAC CTGAAGTTGC TTTTCACCCG GAAGAGAGGC AAACCACAAC C              471
```

(2) INFORMATION FOR SEQ ID NO:44:

(i) SEQUENCE CHARACTERISTICS:
        (A) LENGTH: 487 base pairs
        (B) TYPE: nucleic acid
        (C) STRANDEDNESS: single
        (D) TOPOLOGY: linear (xi) SEQUENCE DESCRIPTION: SEQ ID NO:44:

```
GAATTCGGCA CGAGCTCCCA CTTCTGTCTC GCCACCATTA CTAGCTTCAA AGCCCAGATC      60

TCAGTTTCGT GCTCTCTTCG TCATCTCTGC CTCTTGCCAT GGATCCGTAC AAGTATCGCC     120

CGTCCAGCGC TTACGATTCC AGCTTTTGGA CAACCAACTA CGGTGCTCCC GTCTGGAACA     180

ATGACTCATC GCTGACTGTT GGAACTAGAG GTCCGATTCT CCTGGAGGAC TACCATCTGA     240

TTGAGAAACT TGCCAACTTC GAGAGAGAGA GGATTCCTGA GCGGGTGGTC CATGCACGGG     300

GAGCCAGCGC GAAAGGGTTC TTCGAGGTCA CCCACGACAT CTCTCACTTG ACCTGTGCTG     360

ATTTCCTCCG GGCTCCTGGA GTCCAGACGC CCGTAATCGT CCGTTTCTCC ACCGTCATCC     420

ACGAGCGCGG CAGCCCGAAC CTCAGGGACC CTCGTGGTTT TGCAGTGAAG TTCTACACCA     480

GAGAGGG                                                               487
```

(2) INFORMATION FOR SEQ ID NO:45:

(i) SEQUENCE CHARACTERISTICS:
        (A) LENGTH: 684 base pairs
        (B) TYPE: nucleic acid
        (C) STRANDEDNESS: single
        (D) TOPOLOGY: linear (xi) SEQUENCE DESCRIPTION: SEQ ID NO:45:

```
GAATTCCTGC AGCCCGGGGG ATCCACTAGT TCTAGAGCGG CCGCCACCGC GGTGGAGCTC      60

GCGCGCCTGC AGGTCGACAC TAGTGGATCC AAAGAATTCG GCACGAGGCC CGACGGCCAC     120

TTGTTGGACG CCATGGAAGC TCTCCGGAAA GCCGGGATTC TGGAACCGTT TAAACTGCAG     180

CCCAAGGAAG GACTGGCTCT CGTCAACGGC ACAGCGGTGG GATCCGCCGT GGCCGCGTCC     240

GTCTGTTTTG ACGCCAACGT GCTGGGCGTG CTGGCTGAGA TTCTGTCTGC GCTCTTCTGC     300

GAGGTGATGC AAGGGAAACC GGAGTTCGTA GATCCGTTAA CCCACCAGTT GAAGCACCAC     360

CCAGGGCAGA TCGAAGCCGC GGCCGTCATG GAGTTCCTCC TCGACGGTAG CGACTACGTG     420

AAAGAAGCAG CGCGGCTTCA CGAGAAAGAC CCGTTGAGCA AACCGAAACA AGACCGCTAC     480

GCTCTGCGAA CATCGCCACA GTGGTTGGGG CCTCCGATCG AAGTCATCCG CGCTGCTACT     540

CACTCCATCG AGCGGGAGAT CAATTCCGTC AACGACAATC CGTTAATCGA TGTCTCCAGG     600
```

```
GACATGGCTC TCCACGGCGG CAACTTCCAG GGAACACCCA TCGGAGTTTC CATGGACAAC    660

ATGCGAATCT CTTTGGCAGC CGTC                                          684
```

(2) INFORMATION FOR SEQ ID NO:46:

(i) SEQUENCE CHARACTERISTICS:
        (A) LENGTH: 418 base pairs
        (B) TYPE: nucleic acid
        (C) STRANDEDNESS: single
        (D) TOPOLOGY: linear (xi) SEQUENCE DESCRIPTION: SEQ ID NO:46:

```
GAATTCGGCA CGAGGACAAG GTCATAGGCC CTCTCTTCAA ATGCTTGGAT GGGTGGAAAG     60

GAACTCCTGG CCCATTCTGA AATAAATAAT CTTCCAAGAT CGCCTTTATA CAACGACTGC    120

TATGATTTGA GTCCTCGGAT CTTTTTGTTG ATGCAGTTGT TTACCGATCT GGAATTTGAT    180

TGGTCATAAA GCTTGATTTT GTTTTTCTTT CTTTTGTTTT ATACTGCTGG ATTTGCATCC    240

CATTGGATTT GCCAGAAATA TGTAAGGGTG GCAGATCATT TGGGTGATCT GAAACATGTA    300

AAAGTGGCGG ATCATTTGGG TAGCATGCAG ATCAGTTGGG TGATCGTGTA CTGCTTTCAC    360

TATTACTTAC ATATTTAAAG ATCGGGAATA AAAACATGAT TTTAATTGAA AAAAAAA      418
```

(2) INFORMATION FOR SEQ ID NO:47:

(i) SEQUENCE CHARACTERISTICS:
        (A) LENGTH: 479 base pairs
        (B) TYPE: nucleic acid
        (C) STRANDEDNESS: single
        (D) TOPOLOGY: linear (xi) SEQUENCE DESCRIPTION: SEQ ID NO:47:

```
GATATCCCAA CGACCGAAAA CCTGTATTTT CAGGGCGCCA TGGGGATCCG GAATTCGGCA     60

CGAGCAAGGA AGAAAATATG GTTGCAGCAG CAGAAATTAC GCAGGCCAAT GAAGTTCAAG    120

TTAAAAGCAC TGGGCTGTGC ACGGACTTCG GCTCGTCTGG CAGCGATCCA CTGAACTGGG    180

TTCGAGCAGC CAAGGCCATG GAAGGAAGTC ACTTTGAAGA AGTGAAAGCG ATGGTGGATT    240

CGTATTTGGG AGCCAAGGAG ATTTCCATTG AAGGGAAATC TCTGACAATC TCAGACGTTG    300

CTGCCGTTGC TCGAAGATCG CAAGTGAAAG TGAAATTGGA TGCTGCGGCT GCCAAATCTA    360

GGGTCGAGGA GAGTTCAAAC TGGGTTCTCA CCCAGATGAC CAAGGGGACG GATACCTATG    420

GTGTCACTAC TGGTTTCGGA GCCACTTCTC ACAGGAGAAC GAACCAGGGA GCCGAGCTT    479
```

(2) INFORMATION FOR SEQ ID NO:48:

(i) SEQUENCE CHARACTERISTICS:
        (A) LENGTH: 1785 base pairs
        (B) TYPE: nucleic acid
        (C) STRANDEDNESS: single
        (D) TOPOLOGY: linear (xi) SEQUENCE DESCRIPTION: SEQ ID NO:48:

```
TATCGATAAG CTTGATATCG AATTCCTGCA GCCCGGGGGA TCCACTAGTT CTAGAGCGGC     60

CGCCACCGCG GTGGAGCTCG CGCGCCTGCA GGTCGACACT AGTGGATCCA AAGAATTCGG    120

CACGAGGTTG CAGGTCGGGG ATGATTTGAA TCACAGAAAC CTCAGCGATT TTGCCAAGAA    180

ATATGGCAAA ATCTTTCTGC TCAAGATGGG CCAGAGGAAT CTTGTGGTAG TTTCATCTCC    240

CGATCTCGCC AAGGAGGTCC TGCACACCCA GGGCGTCGAG TTTGGGTCTC GAACCCGGAA    300

CGTGGTGTTC GATATCTTCA CGGGCAAGGG GCAGGACATG GTGTTCACCG TCTATGGAGA    360

TCACTGGAGA AAGATGCGCA GGATCATGAC TGTGCCTTTC TTTACGAATA AAGTTGTCCA    420
```

```
GCACTACAGA TTCGCGTGGG AAGACGAGAT CAGCCGCGTG GTCGCGGATG TGAAATCCCG      480

CGCCGAGTCT TCCACCTCGG GCATTGTCAT CCGTAGGCGC CTCCAGCTCA TGATGTATAA      540

TATTATGTAT AGGATGATGT TCGACAGGAG ATTCGAATCC GAGGACGACC CGCTTTTCCT      600

CAAGCTCAAG GCCCTCAACG GAGAGCGAAG TCGATTGGCC CAGAGCTTTG AGTACAATTA      660

TGGGGATTTC ATTCCCATTC TTAGGCCCTT CCTCAGAGGT TATCTCAGAA TCTGCAATGA      720

GATTAAAGAG AAACGGCTCT CTCTTTTCAA GGACTACTTC GTGGAAGAGC GCAAGAAGCT      780

CAACAGTACC AAGACTAGTA CCAACACCGG GGGAGCTCAA GTGTGCAATG GACCATATTT      840

TAGATGCTCA GGACAAGGGA GAGATCAATG AGGATAATGT TTTGTACATC GTTGAGAACA      900

TCAACGTTGC AGCAATTGAG ACAACGCTGT GGTCGATGGA ATGGGAATA GCGGAGCTGG      960

TGAACCACCA GGACATTCAG AGCAAGGTGC GCGCAGAGCT GGACGCTGTT CTTGGACCAG     1020

GCGTGCAGAT AACGGAACCA GACACGACAA GGTTGCCCTA CCTTCAGGCG GTTGTGAAGG     1080

AAACCCTTCG TCTCCGCATG GCGATCCCGT TGCTCGTCCC CCACATGAAT CTCCACGACG     1140

CCAAGCTCGG GGGCTACGAT ATTCCGGCAG AGAGCAAGAT CCTGGTGAAC GCCTGGTGGT     1200

TGGCCAACAA CCCCGCCAAC TGGAAGAACC CCGAGGAGTT CCGCCCCGAG CGGTTCTTCG     1260

AGGAGGAGAA GCACACCGAA GCCAATGGCA ACGACTTCAA ATTCCTGCCT TCGGTGTGGG     1320

GAGGAGGAGC TGCCCGGGAA TCATTCTGGC GCTGCCTCTC CTCGCACTCT CCATCGGAAG     1380

ACTTGTTCAG AACTTCCACC TTCTGCCGCC GCCCGGGCAG AGCAAAGTGG ATGTCACTGA     1440

GAAGGGCGGG CAGTTCAGCC TTCACATTCT CAACCATTCT CTCATCGTCG CCAAGCCCAT     1500

AGCTTCTGCT TAATCCCAAC TTGTCAGTGA CTGGTATATA AATGCGCGCA CCTGAACAAA     1560

AAACACTCCA TCTATCATGA CTGTGTGTGC GTGTCCACTG TCGAGTCTAC TAAGAGCTCA     1620

TAGCACTTCA AAAGTTTGCT AGGATTTCAA TAACAGACAC CGTCAATTAT GTCATGTTTC     1680

AATAAAAGTT TGCATAAATT AAATGATATT TCAATATACT ATTTTGACTC TCCACCAATT     1740

GGGGAATTTT ACTGCTAAAA AAAAAAAAAA AAAAAAAAAA AAAAA                    1785

(2) INFORMATION FOR SEQ ID NO:49:

(i) SEQUENCE CHARACTERISTICS:
        (A) LENGTH: 475 base pairs
        (B) TYPE: nucleic acid
        (C) STRANDEDNESS: single
        (D) TOPOLOGY: linear (xi) SEQUENCE DESCRIPTION: SEQ ID NO:49:

GAATTCGGCA CGAGATTTCC ATGGACGATT CCGTTTGGCT TCAATTCGTT TCCTCTGGCT       60

GTCCTCGTCC TCGTTTTCCT TGTTCTTCCT CCGACTTTTT CTCTGGAAGC TATGGCGTAA      120

TAGGAACCTG CCGCCAGGAC CCCCGGCATG GCCGATCGTA GGGAACGTCC TTCAGATTGG      180

ATTTTCCAGC GGCGCGTTCG AGACCTCAGT GAAGAAATTC CATGAGAGAT ACGGTCCAAT      240

ATTCACTGTG TGGCTCGGTT CCCGCCCTCT GCTGATGATC ACCGACCGCG AGCTTGCCCA      300

CGAGGCGCTC GTACAGAAGG GCTCCGTCTT CGCTGACCGC CCGCCCGCCC TCGGGATGCA      360

GAAAATCTTC AGTAGCAACC AGCACAACAT CACTTCGGCT GAATACGGCC CGCTGTGGCG      420

GAGCCTTCGC AGGAATCTGG TTAAAGAAGC CCTGAGACTT CGGCGATGAA GGCTT           475

(2) INFORMATION FOR SEQ ID NO:50:

(i) SEQUENCE CHARACTERISTICS:
        (A) LENGTH: 801 base pairs
        (B) TYPE: nucleic acid
```

(C) STRANDEDNESS: single
        (D) TOPOLOGY: linear (xi) SEQUENCE DESCRIPTION: SEQ ID NO:50:

GCTCCACCGA CGGTGGACGG TCCGCTACTC AGTAACTGAG TGGGATCCCC CGGGCTGACA    60

GGCAATTCGA TTTAGCTCAC TCATTAGGCA CCCCAGGCTT TACACTTTAT GCTTCCGGCT   120

CGTATGTTGT GTGGAATTGT GAGCGGATAA CAATTTCACA CAGGAAACAG CTATGACCAT   180

GATTACGCCA AGCGCGCAAT TAACCCTCAC TAAAGGGAAC AAAAGCTGGA GCTCCACCGC   240

GGTGGCGGCC GCTCTAGAAC TAGTGGATCC AAAGAATTCG GCACGAGACC CAGTGACCTT   300

CAGGCCTGAG AGATTTCTTG AGGAAGATGT TGATATTAAG GGCCATGATT ACAGGCTACT   360

GCCATTCGGT GCAGGGCGCA GGATCTGCCC TGGTGCACAA TTGGGTATTA ATTTAGTTCA   420

GTCTATGTTG GGACACCTGC TTCATCATTT CGTATGGGCA CCTCCTGAGG GAATGAAGGC   480

AGAAGACATA GATCTCACAG AGAATCCAGG GCTTGTTACT TTCATGGCCA AGCCTGTGCA   540

GGCCATTGCT ATTCCTCGAT GCCTGATCA TCTCTACAAG CGACAGCCAC TCAATTGATC    600

AATTGATCTG ATAGTAAGTT TGAATTTTGT TTTGATACAA AACGAAATAA CGTGCAGTTT   660

CTCCTTTTCC ATAGTCAACA TGCAGCTTTC TTTCTCTGAA GCGCATGCAG CTTTCTTTCT   720

CTGAAGCCCA ACTTCTAGCA AGCAATAACT GTATATTTTA GAACAAATAC CTATTCCTCA   780

AATTGAGTAT TTCTCTGTAG G                                             801

(2) INFORMATION FOR SEQ ID NO:51:

(i) SEQUENCE CHARACTERISTICS:
        (A) LENGTH: 744 base pairs
        (B) TYPE: nucleic acid
        (C) STRANDEDNESS: single
        (D) TOPOLOGY: linear (xi) SEQUENCE DESCRIPTION: SEQ ID NO:51:

GGGCCCCCCT TCGAGGTGGA CACTAGTGGA TCCAAAGAAT TCGGCACGAG GTTTTATCTG    60

AAGGACGCTG TGCTTGAAGG CTCCCAGCCA TTCACCAAAG CCCATGGAAT GAATGCGTTC   120

GAGTACCCGG CCATCGATCA GAGATTCAAC AAGATTTTCA ACAGGGCTAT GTCTGAGAAT   180

TCTACCATGT TGATGAACAA GATTTTGGAT ACTTACGAGG GTTTTAAGGA GGTTCAGGAG   240

TTGGTGGATG TGGGAGGAGG TATTGGGTCG ACTCTCAATC TCATAGTGTC TAGGTATCCC   300

CACATTTCAG GAATCAACTT CGACTTGTCC CATGTGCTGG CCGATGCTCC TCACTACCCA   360

GCTGTGAAAC ATGTGGGTGG AGACATGTTT GATAGTGTAC CAAGTGGCCA AGCTATTTTT   420

ATGAAGTGGA TTCTGCATGA TTGGAGCGAT GATCATTGCA GGAAGCTTTT GAAGAATTGT   480

CACAAGGCGT TGCCAGAGAA GGGGAAGGTG ATTGCGGTGG ACACCATTCT CCCAGTGGCT   540

GCAGAGACAT CTCCTTATGC TCGTCAGGGA TTTCATACAG ATTTACTGAT GTTGGCATAC   600

AACCCAGGGG GCAAGGAACG CACAGAGCAA GAATTTCAAG ATTTAGCTAA GGAGACGGGA   660

TTTGCAGGTG GTGTTGAACC TGTATGTTGT GTCAATGGAA TGTGGGTAAT GGAATTCCTG   720

CAGCCCGGGG GATCCACTAG TTCT                                           744

(2) INFORMATION FOR SEQ ID NO:52:

(i) SEQUENCE CHARACTERISTICS:
        (A) LENGTH: 426 base pairs
        (B) TYPE: nucleic acid
        (C) STRANDEDNESS: single
        (D) TOPOLOGY: linear (xi) SEQUENCE DESCRIPTION: SEQ ID NO:52:

| | |
|---|---:|
| GTGGCCCTGG AAGTAGTGTG CGCGACATGG ATTCCTTGAA TTTGAACGAG TTTATGTTGT | 60 |
| GGTTTCTCTC TTGGCTTGCT CTCTACATTG GATTTCGTTA TGTTTTGAGA TCGAACTTGA | 120 |
| AGCTCAAGAA GAGGCGCCTC CCGCCGGGCC CATCGGGATG GCCAGTGGTG GGAAGTCTGC | 180 |
| CATTGCTGGG AGCGATGCCT CACGTTACTC TCTACAACAT GTATAAGAAA TATGGCCCCG | 240 |
| TTGTCTATCT CAAACTGGGG ACGTCCGACA TGGTTGTGGC CTCCACGCCC GCTGCAGCTA | 300 |
| AGGCGTTTCT GAAGACTTTG GATATAAACT TCTCCAACCG GCCGGGAAAT GCAGGAGCCA | 360 |
| CGTACATCGC CTACGATTCT CAGGACATGG TGTGGGCAGC GTATGGAGGA CGGTGGAAGA | 420 |
| TGGAGC | 426 |

(2) INFORMATION FOR SEQ ID NO:53:

(i) SEQUENCE CHARACTERISTICS:
        (A) LENGTH: 562 base pairs
        (B) TYPE: nucleic acid
        (C) STRANDEDNESS: single
        (D) TOPOLOGY: linear (xi) SEQUENCE DESCRIPTION: SEQ ID NO:53:

| | |
|---|---:|
| CAGTTCGAAA TTAACCTCAC TAAAGGGAAC AAAAGCTGGA GTTCGCGCGC CTGCAGGTCG | 60 |
| ACACTAGTGG ATCCAAAGAA TTCGGCACGA GCTTTGAGGC AACCTACATT CATTGAATCC | 120 |
| CAGGATTTCT TCTTGTCCAA ACAGGTTTAA GGAAATGGCA GGCACAAGTG TTGCTGCAGC | 180 |
| AGAGGTGAAG GCTCAGACAA CCCAAGCAGA GGAGCCGGTT AAGGTTGTCC GCCATCAAGA | 240 |
| AGTGGGACAC AAAAGTCTTT TGCAGAGCGA TGCCCTCTAT CAGTATATAT TGGAAACGAG | 300 |
| CGTGTACCCT CGTGAGCCCG AGCCAATGAA GGAGCTCCGC GAAGTGACTG CCAAGCATCC | 360 |
| CTGGAACCTC ATGACTACTT CTGCCGATGA GGGTCAATTT CTGGGCCTCC TGCTGAAGCT | 420 |
| CATTAACGCC AAGAACACCA TGGAGATTGG GGTGTACACT GGTTACTCGC TTCTCAGCAC | 480 |
| AGCCCTTGCA TTGCCCGATG ATGGAAAGAT TCTAGCCATG GACATCAACA GAGAGAACTA | 540 |
| TGATATCGGA TTGCCTATAA TT | 562 |

(2) INFORMATION FOR SEQ ID NO:54:

(i) SEQUENCE CHARACTERISTICS:
        (A) LENGTH: 1074 base pairs
        (B) TYPE: nucleic acid
        (C) STRANDEDNESS: single
        (D) TOPOLOGY: linear (xi) SEQUENCE DESCRIPTION: SEQ ID NO:54:

| | |
|---|---:|
| TCGTGCCGCT CGATCCTCAC AGGCCCTTTT TATTTCCCTG GTGAACGATA CGATGGGCTC | 60 |
| GCACGCTGAG AATGGCAACG GGTGGAGGT TGTTGATCCA ACGGACTTAA CTGACATCGA | 120 |
| GAATGGGAAA CCAGGTTATG ACAAGCGTAC GCTGCCTGCG GACTGGAAGT TTGGAGTGAA | 180 |
| GCTTCAAAAC GTTATGGAAG AATCCATTTA CAAGTACATG CTGGAAACAT TCACCCGCCA | 240 |
| TCGAGAGGAC GAGGCGTCCA AGGAGCTCTG GAACGAACA TGGAACCTGA CACAGAGAGG | 300 |
| GGAGATGATG ACATTGCCAG ATCAGGTGCA GTTCCTGCGC TTGATGGTAA AGATGTCAGG | 360 |
| TGCTAAAAAG GCATTGGAGA TCGGAGTTTT CACTGGCTAT TCATTGCTCA ATATCGCTCT | 420 |
| CGCTCTTCCT TCTGATGGCA AGGTGGTAGC TGTGGATCCA GGAGATGACC CCAAATTTGG | 480 |
| CTGGCCCTGC TTCGTTAAGG CTGGAGTTGC AGACAAAGTG GAGATCAAGA AAACTACAGG | 540 |
| GTTGGACTAT TTGATTCCC TTATTCAAAA GGGGGAGAAG GATTGCTTCG ACTTTGCATT | 600 |
| CGTGGACGCA GACAAAGTGA ACTACGTGAA CTATCATCCA CGGCTGATGA AGTTAGTGCG | 660 |

```
CGTGGGGGGC GTCATAATTT ACGACGACAC CCTCTGGTTT GGTCTGGTGG GAGGAAAGGA      720

TCCCCACAAC CTGCTTAAGA ATGATTACAT GAGGACTTCT CTGGAGGGTA TCAAGGCCAT      780

CAACTCCATG GTAGCCAACG ACCCCAACTT GGAGGTCGCC ACAGTCTTTA TGGGATATGG      840

TGTCACTGTT TGTTACCGCA CTGCTTAGTT AGCTAGTCCT CCGTCATTCT GCTATGTATG      900

TATATGATAA TGGCGTCGAT TTCTGATATA GGTGGTTTTT CAATGTTTCT ATCGTCATGT      960

TTTCTGTTTA GCCAGAATGT TTCGATCGTC ATGGTTTCTG TTAAAGCCAG AATAAAATTA     1020

GCCGCTTGCA GTTCAAAAAA AAAAAAAAAA AAAAACTCGA GACTAGTTCT CTTC           1074
```

(2) INFORMATION FOR SEQ ID NO:55:

(i) SEQUENCE CHARACTERISTICS:
        (A) LENGTH: 1075 base pairs
        (B) TYPE: nucleic acid
        (C) STRANDEDNESS: single
        (D) TOPOLOGY: linear (xi) SEQUENCE DESCRIPTION: SEQ ID NO:55:

```
TCGGAGCTCT CGAATCCTCA CAGGCCCTTT TTATTTCCCT GGTGAACGAT ACGATGGGCT       60

CGCACGCTGA GAATGGCAAC GGGGTGGAGG TTGTTGATCC AACGGACTTA ACTGACATCG      120

AAGAATGGGA AACCAGGTTA TGACAAGCGT CGCTGCCTGC GGACTGGAAG TTTGGAGTGA      180

AGCTTCAAAA CGTTATGGAA GAATCCATTT ACAAGTACAT GCTGGAAACA TTCACCCGCC      240

ATCGAGAGGA CGAGGCGTCC AAGGAGCTCT GGGAACGAAC ATGGAACCTG ACACAGAGAG      300

GGGAGATGAT GACATTGCCA GATCAGGTGC AGTTCCTGCG CTTGATGGTA AGATGTCAG       360

GTGCTAAAAA GGCATTGGAG ATCGGAGTTT TCACTGGCTA TTCATTGCTC AATATCGCTC      420

TCGCTCTTCC TTCTGATGGC AAGGTGGTAG CTGTGGATCC AGGAGATGAC CCCAAATTTG      480

GCTGGCCCTG CTTCGTTAAG GCTGGAGTTG CAGACAAAGT GGAGATCAAG AAAACTACAG      540

GGTTGGACTA TTTGGATTCC CTTATTCAAA AGGGGGAGAA GGATTGCTTC GACTTTGCAT      600

TCGTGGACGC AGACAAAGTG AACTACGTGA ACTATCATCC ACGGCTGATG AAGTTAGTGC      660

GCGTGGGGGG CGTCATAATT TACGACGACA CCCTCTGGTT TGGTCTGGTG GGAGGAAAGG      720

ATCCCCACAA CCTGCTTAAG AATGATTACA TGAGGACTTC TCTGGAGGGT ATCAAGGCCA      780

TCAACTCCAT GGTAGCCAAC GACCCCAACT TGGAGGTCGC CACAGTCTTT ATGGGATATG      840

GTGTCACTGT TTGTTACCGC ACTGCTTAGT TAGCTAGTCC TCCGTCATTC TGCTATGTAT      900

GTATATGATA ATGGCGTCGA TTTCTGATAT AGGTGGTTTT TCAATGTTTC TATCGTCATG      960

TTTTCTGTTT AGCCAGAATG TTTCGATCGT CATGGTTTCT GTTAAAGCCA GAATAAAATT     1020

AGCCGCTTGC AGTTCAAAAA AAAAAAAAAA AAAAAACTCG AGACTAGTTC TCTTC          1075
```

(2) INFORMATION FOR SEQ ID NO:56:

(i) SEQUENCE CHARACTERISTICS:
        (A) LENGTH: 1961 base pairs
        (B) TYPE: nucleic acid
        (C) STRANDEDNESS: single
        (D) TOPOLOGY: linear (xi) SEQUENCE DESCRIPTION: SEQ ID NO:56:

```
GTTTTCCGCC ATTTTTCGCC TGTTTCTGCG GAGAATTTGA TCAGGTTCGG ATTGGGATTG       60

AATCAATTGA AAGGTTTTTA TTTTCAGTAT TTCGATCGCC ATGGCCAACG GAATCAAGAA      120

GGTCGAGCAT CTGTACAGAT CGAAGCTTCC CGATATCGAG ATCTCCGACC ATCTGCCTCT      180

TCATTCGTAT TGCTTTGAGA GAGTAGCGGA ATTCGCAGAC AGACCCTGTC TGATCGATGG      240
```

```
GGCGACAGAC AGAACTTATT GCTTTTCAGA GGTGGAACTG ATTTCTCGCA AGGTCGCTGC        300

CGGTCTGGCG AAGCTCGGGT TGCAGCAGGG GCAGGTTGTC ATGCTTCTCC TTCCGAATTG        360

CATCGAATTT GCGTTTGTGT TCATGGGGGC CTCTGTCCGG GGCGCCATTG TGACCACGGC        420

CAATCCTTTC TACAAGCCGG GCGAGATCGC CAAACAGGCC AAGGCCGCGG GCGCGCGCGA        480

TCATAGTTAC CCTGGCAGCT TATGTGGAGA ACTGGCCGA TCTGCAGAGC CACGATGTGC        540

TCGTCATCAC AATCGATGAT GCTCCCAAGG AAGGTTGCCA ACATATTTCC GTTCTGACCG        600

AAGCCGACGA AACCCAATGC CCGGCCGTGA CAATCCACCC GGACGATGTC GTGGCGTTGC        660

CCTATTCTTC CGGAACCACG GGGCTCCCCA AGGGCGTGAT GTTAACGCAC AAAGGCCTGG        720

TGTCCAGCGT TGCCCAGCAG GTCGATGGTG AAAATCCCAA TCTGTATTTC CATTCCGATG        780

ACGTGATACT CTGTGTCTTG CCTCTTTTCC ACATCTATTC TCTCAATTCG GTTCTCCTCT        840

GCGCGCTCAG AGCCGGGGCT GCGACCCTGA TTATGCAGAA ATTCAACCTC ACGACCTGTC        900

TGGAGCTGAT TCAGAAATAC AAGGTTACCG TTGCCCCAAT TGTGCCTCCA ATTGTCCTGG        960

ACATCACAAA GAGCCCCATC GTTTCCCAGT ACGATGTCTC GGCCGTCCGG ATAATCATGT       1020

CCGGCGCTGC GCCTCTCGGG AAGGAACTCG AAGATGCCCT CAGAGAGCGT TTTCCCAAGG       1080

CCATTTTCGG GCAGGGCTAC GGCATGACAG AAGCAGGCCC GGTGCTGGCA ATGAACCTAG       1140

CCTTCGCAAA GAATCCTTTC CCCGTCAAAT CTGGCTCCTG CGGAACAGTC GTCCGGAACG       1200

CTCAAATAAA GATCCTCGAT ACAGAAACTG GCGAGTCTCT CCCGCACAAT CAAGCCGGCG       1260

AAATCTGCAT CCGCGGACCC GAAATAATGA AAGGATATAT TAACGACCCG GAATCCACGG       1320

CCGCTACAAT CGATGAAGAA GGCTGGCTCC ACACAGGCGA CGTCGGGTAC ATTGACGATG       1380

ACGAAGAAAT CTTCATAGTC GACAGAGTAA AGGAGATTAT CAAATATAAG GGCTTCCAGG       1440

TGGCTCCTGC TGAGCTGGAA GCTTTACTTG TTGCTCATCC GTCAATCGCT GACGCAGCAG       1500

TCGTTCCTCA AAAGCACGAG GAGGCGGGCG AGGTTCCGGT GGCGTTCGTG GTGAAGTCGT       1560

CGGAAATCAG CGAGCAGGAA ATCAAGGAAT TCGTGGCAAA GCAGGTGATT TTCTACAAGA       1620

AAATACACAG AGTTTACTTT GTGGATGCGA TTCCTAAGTC GCCGTCCGGC AAGATTCTGA       1680

GAAAGGATTT GAGAAGCAGA CTGGCAGCAA ATGAAAATG AATTTCCATA TGATTCTAAG       1740

ATTCCTTTGC CGATAATTAT AGGATTCCTT TCTGTTCACT TCTATTTATA TAATAAAGTG       1800

GTGCAGAGTA AGCGCCCTAT AAGGAGAGAG AGAGCTTATC AATTGTATCA TATGGATTGT       1860

CAACGCCCTA CACTCTTGCG ATCGCTTTCA ATATGCATAT TACTATAAAC GATATATGTT       1920

TTTTTTATAA ATTTACTGCA CTTCTCGTTC AAAAAAAAAA A                          1961

(2) INFORMATION FOR SEQ ID NO:57:

(i) SEQUENCE CHARACTERISTICS:
        (A) LENGTH: 1010 base pairs
        (B) TYPE: nucleic acid
        (C) STRANDEDNESS: single
        (D) TOPOLOGY: linear (xi) SEQUENCE DESCRIPTION: SEQ ID NO:57:

GACAAACTTG GTCGTTTGTT TAGGTTTTGC TGCAGGTGAA CACTAATATG GAAGGCCAGA         60

TTGCAGCATT AAGCAAAGAA GATGAGTTCA TTTTTCACAG CCCTTTTCCT GCAGTACCTG        120

TTCCAGAGAA TATAAGTCTT TTCCAGTTTG TTCTGGAAGG TGCTGAGAAA TACCGTGATA        180

AGGTGGCCCT CGTGGAGGCC TCCACAGGGA AGGAGTACAA CTATGGTCAG GTGATTTCGC        240

TCACAAGGAA TGTTGCAGCT GGGCTCGTGG ACAAAGGCAT TCAAAAGGGC GATGTTGTAT        300
```

```
TTGTTCTGCT TCCAAATATG GCAGAATACC CCATTATTGT GCTGGGAATA ATGTTGGCCG      360

GCGCAGTGTT TTCTGGGGCA AATCCTTCTG CACACATCAA TGAAGTTGAA AAACATATCC      420

AGGATTCTGG AGCAAAGATT GTTGTGACAG TTGGGTCTGC TTATGAGAAG GTGAGGCAAG      480

TGAAACTGCC TGTTATTATT GCAGATAACG AGCATGTCAT GAACACAATT CCATTGCAGG      540

AAATTTTTGA GAGAAACTAT GAGGCCGCAG GGCCTTTTGT ACAAATTTGT CAGGATGATC      600

TGTGTGCACT CCCTTATTCC TCTGGCACCA CAGGGGCCTC TAAAGGTGTC ATGCTCACTC      660

ACAGAAATCT GATTGCAAAT CTGTGCTCTA GCTTGTTTGA TGTCCATGAA TCTCTTGTAG      720

GAAATTTCAC CACGTTGGGG CTGATGCCAT TCTTTCACAT ATATGGCATC ACGGGCATCT      780

GTTGCGCCAC TCTTCGCAAC GGAGGCAAGG TCGTGGTCAT GTCCAGATTC GATCTCCGAC      840

ACTTTATCAG TTCTTTGATT ACTTATGAGG TCAACTTCGC GCCTATTGTC CCGCCTATAA      900

TGCTCTCCCT CCGGTTTAAA AATCCTATCG TTAACGAGTT CGATCTCAGC CGCTTGAAAC      960

TCCAAAGCTG TTCATGACTG CGGCTGCTCC ACTGGCGCCG GATCTACTGC                1010

(2) INFORMATION FOR SEQ ID NO:58:

(i) SEQUENCE CHARACTERISTICS:
        (A) LENGTH: 741 base pairs
        (B) TYPE: nucleic acid
        (C) STRANDEDNESS: single
        (D) TOPOLOGY: linear (xi) SEQUENCE DESCRIPTION: SEQ ID NO:58:

GAATTCGGCA CGAGACCATT TCCAGCTAAT ATTGGCATAG CAATTGGTCA TTCTATCTTT       60

GTCAAAGGAG ATCAAACAAA TTTTGAAATT GGACCTAATG GTGTGGAGGC TAGTCAGCTA      120

TACCCAGATG TGAAATATAC CACTGTCGAT GAGTACCTCA GCAAATTTGT GTGAAGTATG      180

CGAGATTCTC TTCCACATGC TTCAGAGATA CATAACAGTT TCAATCAATG TTTGTCCTAG      240

GCATTTGCCA AATTGTGGGT TATAATCCTT CGTAGGTGTT TGGCAGAACA GAACCTCCTG      300

TTTAGTATAG TATGACGAGC TAGGCACTGC AGATCCTTCA CACTTTTCTC TTCCATAAGA      360

AACAAATACT CACCTGTGGT TTGTTTTCTT TCTTTCTGGA ACTTTGGTAT GGCAATAATG      420

TCTTTGGAAA CCGCTTAGTG TGGAATGCTA AGTACTAGTG TCCAGAGTTC TAAGGGAGTT      480

CCAAAATCAT GGCTGATGTG AACTGGTTGT TCCAGAGGGT GTTTACAACC AACAGTTGTT      540

CAGTGAATAA TTTTGTTAGA GTGTTTAGAT CCATCTTTAC AAGGCTATTG AGTAAGGTTG      600

GTGTTAGTGA ACGGAATGAT GTCAAATCTT GATGGGCTGA CTGACTCTCT TGTGATGTCA      660

AATCTTGATG GATTGTGTCT TTTTCAATGG TAAAAAAAAA AAAAAAAAAA AAAAAAAAA      720

AAAAAAAAAA AAAAAAAAA A                                                741

(2) INFORMATION FOR SEQ ID NO:59:

(i) SEQUENCE CHARACTERISTICS:
        (A) LENGTH: 643 base pairs
        (B) TYPE: nucleic acid
        (C) STRANDEDNESS: single
        (D) TOPOLOGY: linear (xi) SEQUENCE DESCRIPTION: SEQ ID NO:59:

CTCATCTCGG AGTTGCAGGC TGCAGCTTTT GGCCCAAAGC ATGATATCAG ATCAAACGAC       60

GCAGATGAAG CAAACGGATC AAACAGTTTG CGTTACTGGA GCAGCGGGTT TCATTGCCTC      120

ATGGCTTGTC AAGATGCTCC TCATCAGAGG TTACACTGTC AGAGCAGCAG TTCGGACCAA      180

CCCAGCTGAT GATAGGTGGA AGTATGAGCA TCTGCGAGAG TTGGAAGGAG CAAAAGAGAG      240
```

```
GCTTGAGCTT GTGAAAGCTG ATATTCTCCA TTACCAGAGC TTACTCACAG TCATCAGAGG      300

TTGCCACGGT GTCTTTCACA TGGCTTCAGT TCTCAATGAT GACCCTGAGC AAGTGATAGA      360

ACCAGCAGTC GAAGGGACGA GGAATGTGAT GGAGGCCTGC GCAGAAACTG GGGTGAAGCG      420

CGTTGTTTTT ACTTCTTCCA TCGGCGCAGT TTACATGAAT CCTCATAGAG ACCCGCTCGC      480

GATTGTCCAT GATGACTGCT GGAGCGATTT GACTACTGCG TACAAACCAA GAATTGGTAT      540

TGCTATGCAA AAACCTTGGC AGAGAAATCT GCATGGGATA TTGCTAAGGG AAGGAATTTA      600

GAGCTTGCAG TGATAAATCC AGGCCTGGCC TTAGGTCCCT TGA                       643

(2) INFORMATION FOR SEQ ID NO:60:

(i) SEQUENCE CHARACTERISTICS:
        (A) LENGTH: 441 base pairs
        (B) TYPE: nucleic acid
        (C) STRANDEDNESS: single
        (D) TOPOLOGY: linear (xi) SEQUENCE DESCRIPTION: SEQ ID NO:60:

GAATTCGGCA CGAGAATTTT TCTGTGGTAA GCATATCTAT GGCTCAAACC AGAGAGAAGG       60

ACGATGTCAG CATAACAAAC TCCAAAGGAT TGGTATGCGT GACAGGAGCG GCTGGTTACT      120

TGGCATCTTG GCTTATCAAG CGTCTCCTCC AGTGTGGTTA CCAAGTGAGA GGAACTGTGC      180

GGGATCCTGG CAATGAGAAA AAGATGGCTC ATTTATGGAA GTTAGATGGG GCGAAAGAGA      240

GACTGCAACT AATGAAAGCT GATTTAATGG ACGAGGGCAG CTTCGATGAG GTCATCAGAG      300

GCTGCCATGG TGTTTTTCAC ACAGCGTCTC CAGTCGTGGG TGTCAAATCA GATCCCAAGA      360

TATGGTATGC TCTGGCCAAG ACTTTAGCAG AAAAAGCAGC ATGGGATTTT GCCCAAGAAA      420

ACCATCTGGA CATGGTTGCA G                                               441

(2) INFORMATION FOR SEQ ID NO:61:

(i) SEQUENCE CHARACTERISTICS:
        (A) LENGTH: 913 base pairs
        (B) TYPE: nucleic acid
        (C) STRANDEDNESS: single
        (D) TOPOLOGY: linear (xi) SEQUENCE DESCRIPTION: SEQ ID NO:61:

GAATTCGGCA CGAGGAAAAC ATCATCCAGG CATTTTGGAA ATTTAGCTCG CCGGTTGATT       60

CAGGATCCTG CAATGGCTTT TGGCGAAGAG CAGACTGCCT TGCCACAAGA AACGCCTTTG      120

AATCCTCCGG TCCATCGAGG AACAGTGTGC GTTACAGGAG CTGCTGGGTT CATAGGGTCA      180

TGGCTCATCA TGCGATTGCT TGAGCGAGGA TATAGTGTTA GAGCAACTGT GCGAGACACT      240

GGTAATCCTG TAAAGACAAA GCATCTGTTG GATCTGCCGG GGGCAAATGA GAGATTGACT      300

CTCTGGAAAG CAGATTTGGA TGATGAAGGA AGCTTTGATG CTGCCATTGA TGGGTGTGAG      360

GGTGTTTTCC ATGTTGCCAC TCCCATGGAT TTCGAGTCCG AGGATCCCGA GAATGAGATA      420

ATTAAGCCAA CAATCAACGG GGTCTTGAAT GTTATGAGAT CGTGTGCAAA AGCCAAGTCC      480

GTGAAGCGAG TTGTTTTCAC GTCATCTGCT GGGACTGTGA ATTTTACAGA TGATTTCCAA      540

ACACCAGGCA AGTTTTTGA CGAATCATGC TGGACCAACG TGGATCTTTG CAGAAAAGTT      600

AAAATGACAG GATGGATGTA CTTTGTATCG AAGACATTAG CAGAGAAAGC TGCTTGGGAT      660

TTTGCAGAGG AGAACAAGAT CGATCTCATT ACTGTTATCC CCACATTGGT CGTTGGACCA      720

TTCATTATGC AGACCATGCC ACCGAGCATG ATCACAGCCT TGGCACTGTT AACGCGGAAT      780

GAACCCCACT ACATGACTAC TGAGACAGGT ACAGCTGGTTC ACTTGGATGA TCTCTGTATG      840
```

```
TCACATATCT TTGTATATGA ACATCCTGAA GCAAAGGGCA GATACATCTC TTCCACATGT      900

GATGCTACCC ATT                                                        913

(2) INFORMATION FOR SEQ ID NO:62:

(i) SEQUENCE CHARACTERISTICS:
        (A) LENGTH: 680 base pairs
        (B) TYPE: nucleic acid
        (C) STRANDEDNESS: single
        (D) TOPOLOGY: linear (xi) SEQUENCE DESCRIPTION: SEQ ID NO:62:

GAATTCGGCA CGAGATCAAT TTTTGCATAT TATTAAAAAG TAAGTGTATT CGTTCTCTAT       60

ATTGATCAGT CACAGAGTCA TGGCCAGTTG TGGTTCCGAG AAAGTAAGAG GGTTGAATGG      120

AGATGAAGCA TGCGAAGAGA ACAAGAGAGT GGTTTGTGTA ACTGGGCAA ATGGGTACAT       180

CGGCTCTTGG CTGGTCATGA GATTACTGGA ACATGGCTAT TATGTTCATG GAACTGTTAG     240

GGACCCAGAA GACACAGGGA AGGTTGGGCA TTTGCTGCGG CTCCCAGGGG CAAGTGAGAA     300

GCTAAAGCTG TTCAAGGCAG AGCTTAACGA CGAAATGGCC TTTGATGATG CTGTGAGCGG     360

TTGTCAAGGG GTTTTCCACG TTGCCAAGCC TGTTAATCTG GACTCAAACG CTCTTCAGGG     420

GGAGGTTGTT GGTCCTGCGG TGAGGGGAAC AGTAAATCTG CTTCGAGCCT GCGAACGATC     480

GGGCACTGTG AAACGAGTGA TACATACCTC GTCCGTTTCA GCAGTGAGAT TCACTGGGAA     540

ACCTGACCCC CCTGATACTG TGCTGGATGA ATCTCATTGG ACTTCGGTCG AGTATTGCAG     600

AAAGACAAAG ATGGTCGGAT GGATGTACTA CATCGCCAAC ACTTATGCAG AAGAGGGAGC     660

CCATAAGTTC GGATCAGAGA                                                680

(2) INFORMATION FOR SEQ ID NO:63:

(i) SEQUENCE CHARACTERISTICS:
        (A) LENGTH: 492 base pairs
        (B) TYPE: nucleic acid
        (C) STRANDEDNESS: single
        (D) TOPOLOGY: linear (xi) SEQUENCE DESCRIPTION: SEQ ID NO:63:

GAATTCGGCA CGAGGCTGGT TCAAGTGTCA GCCCAATGGC CTCCCCTACA GAGAATCCCC       60

AGATTTCAGA AGAGCTGCTA AATCATGAGA TCCATCAAGG AAGTACAGTA TGTGTGACAG     120

GAGCTGCTGG CTTCATAGGA TCATGGCTCG TCATGCGTTT GCTTGAGCGA GGATATACTG     180

TTAGAGGAAC TGTGCGAGAC ACTGGTAATC CGGTGAAGAC GAAGCATCTA TTGGATCTGC     240

CTGGGGCGAA TGAGAGGTTA ACTCTCTGGA AAGCAGATTT GGATGATGAA GGAAGCTTTG     300

ACGCCGCCAT TGATGGTTGT GAGGGAGTTT TCCATGTTGC CACTCCCATG GATTTTGAAT     360

CCGAGGACCC CGAGAACGAG ATAATTAAAC CCGCTGTCAA TGGGATGTTG AATGTTTTGA     420

GATCGTGTGG GAAAACCAAG TCTATGAAGC GAGTTGTTTT CACGTCGTCT GCTGGGACTC     480

TGCTTTTTAC GG                                                        492

(2) INFORMATION FOR SEQ ID NO:64:

(i) SEQUENCE CHARACTERISTICS:
        (A) LENGTH: 524 base pairs
        (B) TYPE: nucleic acid
        (C) STRANDEDNESS: single
        (D) TOPOLOGY: linear (xi) SEQUENCE DESCRIPTION: SEQ ID NO:64:

GAATTCGGCA CGAGCTTGTT CAAAGTCACA TATCTTATTT TCTTTGTGAT ATCTGCAATT       60
```

```
TCCAAGCTTT TCGTCTACCT CCCTGAAAAG ATGAGCGAGG TATGCGTGAC AGGAGGCACA        120

GGCTTCATAG CTGCTTATCT CATTCGTAGT CTTCTCCAGA AAGGTTACAG AGTTCGCACT        180

ACAGTTCGCA ACCCAGATAA TGTGGAGAAG TTTAGTTATC TGTGGGATCT GCCTGGTGCA        240

AACGAAAGAC TCAACATCGT GAGAGCAGAT TTGCTAGAGG AAGGCAGTTT TGATGCAGCA        300

GTAGATGGTG TAGATGGAGT ATTCCATACT GCATCACCTG TCTTAGTCCC ATATAACGAG        360

CGCTTGAAGG AAACCCTAAT AGATCCTTGT GTGAAGGGCA CTATCAATGT CCTCAGGTCC        420

TGTTCAAGAT CACCTTCAGT AAAGCGGGTG GTGCTTACAT CCTCCTGCTC ATCAATACCG        480

ATACGACTAT AATAGCTTAG AGCGTTCCCT GCTGGACTGA GTCA                        524
```

(2) INFORMATION FOR SEQ ID NO:65:

(i) SEQUENCE CHARACTERISTICS:
        (A) LENGTH: 417 base pairs
        (B) TYPE: nucleic acid
        (C) STRANDEDNESS: single
        (D) TOPOLOGY: linear (xi) SEQUENCE DESCRIPTION: SEQ ID NO:65:

```
TCCTAATTGT TCGATCCTCC CTTTTAAAGC CCTTCCCTGG CCTTCATTCC AGGTCACAGA         60

GTTGTTCATG CAGTGCTAGC AGGAGGAGCA GCGTTGCAAT TGGGGAAAAT TCCAAAATCA        120

ATAACGAGAG GACAGAAGTA AGTTTGTGGA AATAGCAACC ATGCCGGTGT TTCCTTCTGG        180

TCTGGACCCC TCTGAGGACA ATGGCAAGCT CGTTTGTGTC ATGGATGCGT CCAGTTATGT        240

AGGTTTGTGG ATTGTTCAGG GCCTTCTTCA ACGAGGCTAT TCAGTGCATG CCACGGTGCA        300

GAGAGACGCT GGCGAGGTTG AGTCTCTCAG AAAAATTGCAT GGGGATCGAT TGCAGATCTT       360

CTATGCAGAT GTCTTGGATT ATCACAGCAT TACTGATGCG CTCAAGGGCT GTTCTGG          417
```

(2) INFORMATION FOR SEQ ID NO:66:

(i) SEQUENCE CHARACTERISTICS:
        (A) LENGTH: 511 base pairs
        (B) TYPE: nucleic acid
        (C) STRANDEDNESS: single
        (D) TOPOLOGY: linear (xi) SEQUENCE DESCRIPTION: SEQ ID NO:66:

```
ATGACACGAA TTTGTGCCTC TCTCTGACCA GAGCTTGAAG CTCTGTCTTC TCTGATATCG         60

CTTCATTCCA TCATCCAGGA GCTTCTGTTA TATCCATTTC CTCAAAATGG ATGCCTACCT        120

TGAAGAAAAT GGATACGGCG CTTCCAATTC TCGGAAATTA ATGTGCCTTA CCGGGGGCTG        180

GAGTTTCCTG GGGATTCATA TCGCAAGAAT GCTGCTCGGC CGGGGTTACT CAGTCCGTTT        240

CGCAATTCCG GTAACGCCAG AAGAGGCAGG CTCACTTATG GAATCCGAAG AAGCATTATC        300

GGGGAAGCTG GAGATATGCC AAGCCGATCT CTTGGATTAT CGCAGCGTTT TCGGCAACAT        360

CAATGGTTGC TCCGGAGTCT TCCACGTCCC TGCGCCCTGT GATCATCTGG ATGGATTACA        420

GGAGTATCCG GTATGATTAG TTTAATAGAT TGACGGGGTA TCCTGTATGA ATTAGTTTAT        480

GAATTTAAGG TTTTCTTAGA ATTTGGATAC T                                      511
```

(2) INFORMATION FOR SEQ ID NO:67:

(i) SEQUENCE CHARACTERISTICS:
        (A) LENGTH: 609 base pairs
        (B) TYPE: nucleic acid
        (C) STRANDEDNESS: single
        (D) TOPOLOGY: linear (xi) SEQUENCE DESCRIPTION: SEQ ID NO:67:

```
CATTGATAGT TGATGGAAGA CCATCAGTAA AGCATGAAAA AGAAATTGTT CCAAGGTGAA      60

GAAGTCAGTT GCTCCAGCAG AACCTTTTTA GCAATTGTTT TTGTATCCTT TTTGCCTTTG     120

AATATGTAAT CCATAAACTT ATGCAGGAAG TGCCTCGTGC CGAATTCGGC ACGAGAATCA     180

CTGACCTTCA CATATTTATT CCAATTCTAA TATCTCTACT CGCTGTCTAC CTGATTTTTC     240

AGTGGCGAAC CAACTTGACA GGGTTGGACA TGGCCAACAG CAGCAAGATT CTGATTATTG     300

GAGGAACAGG CTACATTGGT CGTCATATAA CCAAAGCCAG CCTTGCTCTT GGTCATCCCA     360

CATTCCTTCT TGTCAGAGAG ACCTCCGCTT CTAATCCTGA GAAGGCTAAG CTTCTGGAAT     420

CCTTCAAGGC CTCAGGTGCT ATTATACTCC ATGGATCTTT GGAGGACCAT GCAAGTCTTG     480

TGGAGGCAAT CAAGAAAGTT GATGTAGTTA TCTCGGCTGT CAAGGGACCA CAGCTGACGG     540

TTCAAACAGG ATATTTATCC AGGGTATTTA AAGGGAGGGT TGGAACCCAT CAAGAAGGGT     600

TTTGGCCAA                                                             609
```

(2) INFORMATION FOR SEQ ID NO:68:

(i) SEQUENCE CHARACTERISTICS:
        (A) LENGTH: 474 base pairs
        (B) TYPE: nucleic acid
        (C) STRANDEDNESS: single
        (D) TOPOLOGY: linear (xi) SEQUENCE DESCRIPTION: SEQ ID NO:68:

```
GCAAGATAGG TTTTATTCTT CTGGAGTTGG GTGAGGCTTG GAAATTTAAG TAAAAAGGGT      60

GCATAGCAAT TAAGCAGTTG CAGCCATGGC GGTCTGTGGA ACTGAAGTAG CTCATACTGT     120

GCTCTATGTA GCTGCAGACA TGGTGGAAAA CAACACGTCT ATTGTGACCA CCTCTATGGC     180

TGCAGCAAAT TGTGAGATGG AGAAGCCTCT TCTAAATTCC TCTGCCACCT CAAGAATACT     240

GGTGATGGGA GCCACAGGTT ACATTGGCCG TTTTGTTGCC CAAGAAGCTG TTGCTGCTGG     300

TCATCCTACC TATGCTCTTA TACGCCCGTT TGCTGCTTGT GACCTGGCCA AAGCACAGCG     360

CGTCCAACAA TTGAAGGATG CCGGGGTCCA TATCCTTTAT GGGTCTTTGA GTGATCACAA     420

CCTCTTAGTA AATACATTGA AGGACATGGG CCGTTGTTAT CTCTACCATT GGAG          474
```

(2) INFORMATION FOR SEQ ID NO:69:

(i) SEQUENCE CHARACTERISTICS:
        (A) LENGTH: 474 base pairs
        (B) TYPE: nucleic acid
        (C) STRANDEDNESS: single
        (D) TOPOLOGY: linear (xi) SEQUENCE DESCRIPTION: SEQ ID NO:69:

```
GCAAGATAGG TTTTATTCTT CTGGAGTTGG GTGAGGCTTG GAAATTTAAG TAAAAAGGGT      60

GCATAGCAAT TAAGCAGTTG CAGCCATGGC GGTCTGTGGA ACTGAAGTAG CTCATACTGT     120

GCTCTATGTA GCTGCAGACA TGGTGGAAAA CAACACGTCT ATTGTGACCA CCTCTATGGC     180

TGCAGCAAAT TGTGAGATGG AGAAGCCTCT TCTAAATTCC TCTGCCACCT CAAGAATACT     240

GGTGATGGGA GCCACAGGTT ACATTGGCCG TTTTGTTGCC CAAGAAGCTG TTGCTGCTGG     300

TCATCCTACC TATGCTCTTA TACGCCCGTT TGCTGCTTGT GACCTGGCCA AAGCACAGCG     360

CGTCCAACAA TTGAAGGATG CCGGGGTCCA TATCCTTTAT GGGTCTTTGA GTGATCACAA     420

CCTCTTAGTA AATACATTGA AGGACATGGG CCGTTGTTAT CTCTACCATT GGAG          474
```

(2) INFORMATION FOR SEQ ID NO:70:

(i) SEQUENCE CHARACTERISTICS:
        (A) LENGTH: 608 base pairs
        (B) TYPE: nucleic acid
        (C) STRANDEDNESS: single
        (D) TOPOLOGY: linear (xi) SEQUENCE DESCRIPTION: SEQ ID NO:70:

```
CATTGATAGT TGATGGAAGA CCATCAGTAA AGCATGAAAA AGAAATTGTT CCAAGGTGAA        60

GAAGTCAGTT GCTCCAGCAG AACCTTTTTA GCAATTGTTT TTGTATCCTT TTTGCCTTTG       120

AATATGTAAT CCATAAACTT ATGCAGGAAG TGCCTCGTGC CGAATTCGGC ACGAGAATCA       180

CTGACCTTCA ATATTTATT CCAATTCTAA TATCTCTACT CGCTGTCTAC CTGATTTTTC        240

AGTGGCGAAC CAACTTGACA GGGTTGGACA TGGCCAACAG CAGCAAGATT CTGATTATTG       300

GAGGAACAGG CTACATTGGT CGTCATATAA CCAAAGCCAG CCTTGCTCTT GGTCATCCCA       360

CATTCCTTCT TGTCAGAGAG ACCTCCGCTT CTAATCCTGA GAAGGCTAAG CTTCTGGAAT       420

CCTTCAAGGC CTCAGGTGCT ATTATACTCC ATGGATCTTT GGAGGACCAT GCAAGTCTTG       480

TGGAGGCAAT CAAGAAAGTT GATGTAGTTA CTCGGCTGT CAAGGGACCA CAGCTGACGG        540

ATCAAACAGG ATATTTATCC AGGGTATTTA AAGGGAGGTT GGAACCCATC AAGAAGGGTT      600

TTGGCCAA                                                                608
```

(2) INFORMATION FOR SEQ ID NO:71:

(i) SEQUENCE CHARACTERISTICS:
        (A) LENGTH: 1474 base pairs
        (B) TYPE: nucleic acid
        (C) STRANDEDNESS: single
        (D) TOPOLOGY: linear (xi) SEQUENCE DESCRIPTION: SEQ ID NO:71:

```
GAATTCGGCA CGAGAAAACG TCCATAGCTT CCTTGCCAAC TGCAAGCAAT ACAGTACAAG        60

AGCCAGACGA TCGAATCCTG TGAAGTGGTT CTGAAGTGAT GGGAAGCTTG GAATCTGAAA      120

AAACTGTTAC AGGATATGCA GCTCGGGACT CCAGTGGCCA CTTGTCCCCT TACACTTACA      180

ATCTCAGAAA GAAAGGACCT GAGGATGTAA TTGTAAAGGT CATTTACTGC GGAATCTGCC      240

ACTCTGATTT AGTTCAAATG CGTAATGAAA TGGACATGTC TCATTACCCA ATGGTCCCTG      300

GGCATGAAGT GGTGGGGATT GTAACAGAGA TTGGCAGCGA GGTGAAGAAA TTCAAAGTGG      360

GAGAGCATGT AGGGGTTGGT TGCATTGTTG GGTCCTGTCG CAGTTGCGGT AATTGCAATC      420

AGAGCATGGA ACAATACTGC AGCAAGAGGA TTTGGACCTA CAATGATGTG AACCATGACG      480

GCACACCTAC TCAGGGCGGA TTTGCAAGCA GTATGGTGGT TGATCAGATG TTTGTGGTTC      540

GAATCCCGGA GAATCTTCCT CTGGAACAAG CGGCCCCTCT GTTATGTGCA GGGGTTACAG      600

TTTTCAGCCC AATGAAGCAT TTCGCCATGA CAGAGCCCGG GAAGAAATGT GGGATTTTGG      660

GTTTAGGAGG CGTGGGGCAC ATGGGTGTCA AGATTGCCAA AGCCTTTGGA CTCCACGTGA      720

CGGTTATCAG TTCGTCTGAT AAAAAGAAAG AAGAAGCCAT GGAAGTCCTC GGCGCCGATG      780

CTTATCTTGT TAGCAAGGAT ACTGAAAAGA TGATGGAAGC AGCAGAGAGC CTAGATTACA      840

TAATGGACAC CATTCCAGTT GCTCATCCTC TGGAACCATA TCTTGCCCTT CTGAAGACAA      900

ATGGAAAGCT AGTGATGCTG GGCGTTGTTC CAGAGCCGTT GCACTTCGTG ACTCCTCTCT      960

TAATACTTGG GAGAAGGAGC ATAGCTGGAA GTTTCATTGG CAGCATGGAG GAAACACAGG     1020

AAACTCTAGA TTTCTGTGCA GAGAAGAAGG TATCATCGAT GATTGAGGTT GTGGGCCTGG     1080

ACTACATCAA CACGGCCATG GAAAGGTTGG AGAAGAACGA TGTCCGTTAC AGATTTGTGG     1140
```

```
TGGATGTTGC TAGAAGCAAG TTGGATAATT AGTCTGCAAT CAATCAATCA GATCAATGCC     1200

TGCATGCAAG ATGAATAGAT CTGGACTAGT AGCTTAACAT GAAAGGGAAA TTAAATTTTT     1260

ATTTAGGAAC TCGATACTGG TTTTTGTTAC TTTAGTTTAG CTTTTGTGAG GTTGAAACAA     1320

TTCAGATGTT TTTTTAACTT GTATATGTAA AGATCAATTT CTCGTGACAG TAAATAATAA     1380

TCCAATGTCT TCTGCCAAAT TAATATATGT ATTCGTATTT TTATATGAAA AAAAAAAAAA     1440

AAAAAAAAAA AAAAAAAAA AAAAAAAAA AAAA                                   1474

(2) INFORMATION FOR SEQ ID NO:72:

(i) SEQUENCE CHARACTERISTICS:
        (A) LENGTH: 1038 base pairs
        (B) TYPE: nucleic acid
        (C) STRANDEDNESS: single
        (D) TOPOLOGY: linear (xi) SEQUENCE DESCRIPTION: SEQ ID NO:72:

GAATTCGGCA CGAGAGAGGG TTATATATCT TGATTCTGAC CTGATTGTCG TCGACGACAT       60

TGCCAAGCTC TGGGCCACGG ATTTGGAATC TCGTGTCCTC GGGGCACCAG AGTACTGCAA      120

GGCGAATTTC ACAAAGTATT TCACCGATAA TTTCTGGTGG GATCCCGCAT TATCCAAGAC      180

CTTTGAGGGA AAAAACCCT GCTACTTCAA CACAGGCGTA ATGGTGATCG ATCTTGAAAA       240

ATGGCGGGCA GGGGAATTCA CAAGAAAGAT CGAAATCTGG ATGGACATAC AGAAGGAACG      300

CCGTATCTAT GAGCTCGGAT CATTACCGCC ATTTTTACTG GTATTTGCTG GTTTGGTTAA      360

GCAAGTCGAT CATCGTTGGA ATCAGCACGG TTTAGGCGGA GATAATTTGC AAGGCCTTTG      420

CCGAGATCTT CACCCTGGAC CTGTCAGTTT GTTGCATTGG AGTGGTAAGG GCAAACCTTG      480

GCTACGCCTG GAATGCCAAG CGGACTTGCC CTCTGGATAC TTTATGGGCT CCTTATGATC      540

TTTATCGATC AACGTATTAC CTAAATGGGT GAGAGAGCCT CTCTCCTCGG GGTGCTTTTT      600

ATCGAATTAA ACCTGATTTG ATAAAATGCC AAATAGAACT TTACGCCTAT GCATCTTTCA      660

GTTTTGAATT TCAATTCTGG TAACGAATAG AAGAAAACAA TAGCACAGCC ACAGGCAGGA      720

CAAATCCATC ATGAGGGACC AATCGTTTGA ATTTAGTATT AATAAGGTTG TTCCATATAA      780

CGCCTGTGAA GAATGATATT GTGGACTGAT CTATTTATAT TTGTACTGCC ATGCCATCCT      840

CAGCCAGCAG AGAGGCAAGC AATGCCGCTG CAAGTCATGT AGGGAAGGCG TTGTGAACTC      900

AATTTTCGGC GACTGTACAG GATGTAAATT TTTGGAACAT TAATATCATT ATGATAAGTT      960

CCTGAACCAA CAACTGTATA ATACCTTATA AATGTATCTG CAACTCCATT TTTGCATAAA     1020

AAAAAAAAAA AAAAAAAA                                                  1038

(2) INFORMATION FOR SEQ ID NO:73:

(i) SEQUENCE CHARACTERISTICS:
        (A) LENGTH: 372 base pairs
        (B) TYPE: nucleic acid
        (C) STRANDEDNESS: single
        (D) TOPOLOGY: linear (xi) SEQUENCE DESCRIPTION: SEQ ID NO:73:

CTAGGGGTCT TGGGGGGTTC CTGATGCCCA ATTGTTGCTG TGCTTGGCAT GAACCCAAAA       60

CATGCAAGAG ATCTGTAGTC AGTAGTCTTG TTGGATCTAT AGCTTTTAGA AAAGAGTCAC      120

GTCCTTTTAG GGTAACATCA TTCCAACCAT ATCCAGTTCC ACCACCGGCT ACACCTTCAA      180

CGGGAGGAGG AGCAAGATAT TCAGCATTGC TTTGGGCACC AGATGGATAG GCATTATTTT      240

CCATCGGAAT TCAGCCGAGC TCGCCCCCTC AGTCCAATCG TCGTGAAAAT CCCTCAAAAT      300
```

```
TGGGCAATTC TGGCTCGAAA TCGCCAAATT ATGGGCTACA ACAGGATTAA AATTGCACAG    360

AAATCTGCCA GT                                                       372
```

(2) INFORMATION FOR SEQ ID NO:74:

(i) SEQUENCE CHARACTERISTICS:
        (A) LENGTH: 545 base pairs
        (B) TYPE: nucleic acid
        (C) STRANDEDNESS: single
        (D) TOPOLOGY: linear (xi) SEQUENCE DESCRIPTION: SEQ ID NO:74:

```
AAAGAATTCG GCACGAGGGC AATCCGAGCC TAGCCAACCA ACTTGGCAGC AAGGAGCACA     60

GGGAGTTGGC GAGAGAAGCT GTTAGGAAAT CTTTGGTATT GTTGAAAAAT GGGAAGTCAG    120

CCAACAAGCC TTTGCTCCCT TGGAGAAGA ATGCTTCCAA GGTTCTTGTT GCAGGAACCC    180

ATCCTGATAA TCTGGGTTAT CAGTGTGGTG GATGGACGAT GGAATGGCAA GGATTAAGTG    240

GAAACATAAC CGTAGGAACT ACAATTCTGG AAGCTATCAA ACTAGCTGTC AGCCCCTCTA    300

CTGAAGTGGT TTATGAGCAA AATCCAGATG CTAACTATGT CAAAGGACAA GGGTTTTCAT    360

ATGCCATTGT GGTTGTGGGT GAGGCACCAT ACGCAGAAAC GTTTGGAGAC AATCTTAATT    420

TGACCATTCC CCTAGGCGGA GGGGACACGA TTAAGACGGT CTGTGGCTCC TTGAAATGCC    480

TTGTAATCTT GATATCTGGA AGGCCACTTG TTATTGAACC TTATCTTCCA TTGGTGGATC    540

GTTTT                                                               545
```

(2) INFORMATION FOR SEQ ID NO:75:

(i) SEQUENCE CHARACTERISTICS:
        (A) LENGTH: 463 base pairs
        (B) TYPE: nucleic acid
        (C) STRANDEDNESS: single
        (D) TOPOLOGY: linear (xi) SEQUENCE DESCRIPTION: SEQ ID NO:75:

```
GCAGGTCGAC ACTAGTGGAT CCAAAGAATT CGGCACGAGA AAAACAAAT GTTAGCTAGC     60

CTAGTGATGA GCTTTACGTA TACCTGGCCT TTTATACATG GATCTGAGTT TTTATGCAGG    120

TGTAGAGCCT TTTGTTACTC TGTATCACTG GGACTTGCCA CAAGCTCTGG AGGACGAATA    180

CGGTGGATTT CGTAGCAAAA AAGTTGTGGA TGACTTTGGC ATATTCTCAG AAGAATGCTT    240

TCGTGCTTTT GGAGACCGTG TGAAGTACTG GGTAACTGTT AACGAACCGT TGATCTTCTC    300

ATATTTTTCT TACGATGTGG GGCTTCACGC ACCGGGCCGC TGTTCGCCTG GATTTGGAAA    360

CTGCACTGCG GGAAATTCAG CGACAGAGCC TTATATTGTA GCCCATAACA TGCTTCTTGC    420

ACATAGTACC GCTGTTAAAA ATATATAGCA TAAATACCCA GGG                     463
```

(2) INFORMATION FOR SEQ ID NO:76:

(i) SEQUENCE CHARACTERISTICS:
        (A) LENGTH: 435 base pairs
        (B) TYPE: nucleic acid
        (C) STRANDEDNESS: single
        (D) TOPOLOGY: linear (xi) SEQUENCE DESCRIPTION: SEQ ID NO:76:

```
ACACTAGTGG ATCCAAAGAA TTCGGCACGA GGCTACCATC TTCCCTCATA ATATTGGGCT     60

TGGAGCTACC AGGGATCCTG ATCTGGCTAG AAGAATAGGG GCTGCTACGG CTTTGGAAGT    120

TCGAGCTACT GGCATTCAAT ACACATTTGC TCCATGTGTT GCTGTTTGCA GAGATCCTCG    180

ATGGGGCCGC TGCTATGAGA GCTACAGTGA GGATCCAAAA ATTGTCAAGG CCATGACTGA    240
```

```
GATTATCGTT GGCCTGCAAG GGAATCCTCC TGCTAATTCT ACAAAAGGGG GGCCTTTTAT      300

AGCTGGACAG TCAAATGTTG CAGCTTGTGC TAAGCATTTT GTGGGTTATG GTGGAACAAC      360

CAAAGGTATC GATGAGAATA ATACTGTTAT CAACTATCAA GGGTTATTTC AACATTCCAA      420

ATTACCCCCA ATTTT                                                      435
```

(2) INFORMATION FOR SEQ ID NO:77:

(i) SEQUENCE CHARACTERISTICS:
        (A) LENGTH: 451 base pairs
        (B) TYPE: nucleic acid
        (C) STRANDEDNESS: single
        (D) TOPOLOGY: linear (xi) SEQUENCE DESCRIPTION: SEQ ID NO:77:

```
GAATTCGGCA CGAGCCTAGA ATTCTATGGT GAAAATTGTT GGGACAAGGC TGCCCAAGTT       60

TACAAAGGAA CAGTCCCAAA TGGTTAAAGG TTCAATAGAC TATCTAGGCG TTAACCAATA      120

CACTGCTTAT TACATGTATG ATCCTAAACA ACCTAAACAA AATGTAACAG ATTACCAGAC      180

TGGACTGGAA TACAGGCTTT GCATATGCTC GCAATGGAGT GCCTATTGGA CCAAGGGCGA      240

ACTCCAATTG GCTTTACATT GTGCCTTGGG GTCTATACAA GGCCGTCACA TACGTAAAAG      300

AACACTATGG AAATCCAACT ATGATTCTCT CTGAAAATGG AATGGACGAC CTGGAAACGT      360

GACACTTCCA GCAGGACTGC ATGATACCAT CAGGGGTAAC TACTATAAAA GCTATTTGCA      420

AAATTTGATT AATGCACGTG AATGACCGGG G                                    451
```

(2) INFORMATION FOR SEQ ID NO:78:

(i) SEQUENCE CHARACTERISTICS:
        (A) LENGTH: 374 base pairs
        (B) TYPE: nucleic acid
        (C) STRANDEDNESS: single
        (D) TOPOLOGY: linear (xi) SEQUENCE DESCRIPTION: SEQ ID NO:78:

```
CTGCTCTGCA AGCAGTACTA TGCACAGCAA GGCCTGCTTA ACTGAAAACA GAGCGCTGAG       60

CTTGAGGAAA CGCTCAAGCA TTGCTGAGGC CACCGTTTAT CTAAATAGCG CAACATAGGG      120

CTTCAGAAAA ATGGCAATGG CACAAGCATT CAGAGGCCGT GTCTTGCAAG CTGCCCGTTT      180

GCTCCGCCGC AACATTCTGC CGGAGGATAA AAGCTTTGGA TCCGCTGCTT CTCCTAGACG      240

AGCTCTTAGC CTGCTCTCAT CAAAAGCCTT CATCTCTTTC TCTGTTGAAC GGCATCGGCT      300

AGCTGCTACA AATTCAACAA TTGTGTTGCA ATCTCGAAAC TTTTCTGCAA AAGGTAAAAA      360

GACAGGACAA TCTG                                                       374
```

(2) INFORMATION FOR SEQ ID NO:79:

(i) SEQUENCE CHARACTERISTICS:
        (A) LENGTH: 457 base pairs
        (B) TYPE: nucleic acid
        (C) STRANDEDNESS: single
        (D) TOPOLOGY: linear (xi) SEQUENCE DESCRIPTION: SEQ ID NO:79:

```
GAAGAATGGA AGAGATTAAT GGTGATAACG CAGTAAGGAG GAGCTGCTTT CCTCCAGGTT       60

TCATGTTTGG GATAGCAACT TCTGCTTATC AGTGTGAAGG AGCTGCCAAC GAAGGTGGAA      120

AAGGCCCAAG CATCTGGGAC TCATTTTCAC GAACACCAGG CAAAATTCTT GATGGAAGCA      180

ACGGTGATGT AGCAGTGGAT CAGTATCATC GTTATAAGGC AGATGTAAAA CTGATGAAAG      240
```

```
ATATGGGCGT GGCTACCTAC AGATTCTCGA TTTCATGGCC TCGTATATTT CCAAAGGGAA        300

AAGGAGAGAT CAATGAGGAA GGAGTAGCCT ATTACAATAA CCTCATCAAT GAACTCCTCC        360

AGAATGGAAT CCAAGCGTCT GTCAACTTTG TTTCACTGGG ATACTCCCCA GTCTCTGGAG        420

GATGAATATG GCGGATTTCT GAGGCCAACC ATTGTGA                                 457
```

(2) INFORMATION FOR SEQ ID NO:80:

(i) SEQUENCE CHARACTERISTICS:
        (A) LENGTH: 346 base pairs
        (B) TYPE: nucleic acid
        (C) STRANDEDNESS: single
        (D) TOPOLOGY: linear (xi) SEQUENCE DESCRIPTION: SEQ ID NO:80:

```
GGTGTGATGG CAGGAATTCC AGTCCTAAGG CCATTTTGCA TCTGTTTGCT TTCAGTCTAC         60

ATGCTGCACA TTGTAGCTGC AGTAGCTTCA CCAAGGCTAG GTAGAAGCAG CTTCCCAAGG        120

GGTTTCAAAT TTGGTGCAGG GTCATCTGCT TATCAGGCGG AAGGAGCTGC TCATGAGGGT        180

GGCAAAGGCC CAAGCATTTG GGATACATTC TCCCACACTC CAGGTAAAAT CGCTGATGGG        240

AATATTGGGA TGTTGCAGTA GATCAATACC ACCGTTATAA GGAAGATGTG CAGCTTCTCA        300

AATACATGGG AATGGACGTC TATCGTTTCT CTATCTCCTG GTCACG                      346
```

(2) INFORMATION FOR SEQ ID NO:81:

(i) SEQUENCE CHARACTERISTICS:
        (A) LENGTH: 957 base pairs
        (B) TYPE: nucleic acid
        (C) STRANDEDNESS: single
        (D) TOPOLOGY: linear (xi) SEQUENCE DESCRIPTION: SEQ ID NO:81:

```
GAATTCGGCA CGAGAAAGCC CTAGAATTTT TTCAGCATGC TATCACAGCC CCAGCGACAA         60

CTTTAACTGC AATAACTGTG GAAGCGTACA AAAAGTTTGT CCTAGTTTCT CTCATTCAGA        120

CTGGTCAGGT TCCAGCATTT CCAAAATACA CACCTGCTGT TGTCCAAAGA AATTTGAAAT        180

CTTGCACTCA GCCCTACATT GATTTAGCAA ACAACTACAG TAGTGGGAAA ATTTCTGTAT        240

TGGAAGCTTG TGTCAACACG AACACAGAGA AGTTCAAGAA TGATAGTAAT TTGGGGTTAG        300

TCAAGCAAGT TTTGTCATCT CTTTATAAAC GGAATATTCA GAGATTGACA CAGACATATC        360

TGACCCTCTC TCTTCAAGAC ATAGCAAGTA CGGTACAGTT GGAGACTGCT AAGCAGGCTG        420

AACTCCATGT TCTGCAGATG ATTCAAGATG GTGAGATTTT TGCAACCATA AATCAGAAAG        480

ATGGGATGGT GAGCTTCAAT GAGGATCCTG AACAGTACAA AACATGTCAG ATGACTGAAT        540

ATATAGATAC TGCAATTCGG AGAATCATGG CACTATCAAA GAAGCTCACC ACAGTAGATG        600

AGCAGATTTC GTGTGATCAT TCCTACCTGA GTAAGGTGGG GAGAGAGCGT TCAAGATTTG        660

ACATAGATGA TTTTGATACT GTTCCCCAGA AGTTCACAAA TATGTAACAA ATGATGTAAA        720

TCATCTTCAA GACTCGCTTA TATTCATTAC TTTCTATGTG AATTGATAGT CTGTTAACAA        780

TAGTACTGTG GCTGAGTCCA GAAAGGATCT CTCGGTATTA TCACTTGACA TGCCATCAAA        840

AAAATCTCAA ATTTCTCGAT GTCTAGTCTT GATTTTGATT ATGAATGCGA CTTTTAGTTG        900

TGACATTTGA GCACCTCGAG TGAACTACAA AGTTGCATGT TAAAAAAAAA AAAAAAA          957
```

(2) INFORMATION FOR SEQ ID NO:82:

(i) SEQUENCE CHARACTERISTICS:
        (A) LENGTH: 489 base pairs
        (B) TYPE: nucleic acid (C) STRANDEDNESS: single
(D) TOPOLOGY: linear (xi) SEQUENCE DESCRIPTION: SEQ ID NO:82:

```
GCAGGTCGAC ACTAGTGGAT CCAAAGAATT CGGCACGAGA TAAGACTAAT TTTCCAGACA        60
ATCCTCCATT CCCATTCAAT TACACTGGTA CTCCACCCAA TAATACACAG GCTGTGAATG       120
GGACTAGAGT AAAAGTCCTT CCCTTTAACA CAACTGTTCA ATTGATTCTT CAAGACACCA       180
GCATCTTCAG CACAGACAGC CACCCTGTCC ATCTCCATGG TTTCAATTTC TTTGTGGTGG       240
GCCAAGGTGT TGGAAACTAC AATGAATCAA CAGATGCACC AAATTTTAAC CTCATTGACC       300
CTGTCGAGAG AAACACTGTG GGAGTTCCCA AGGAGGTTG GGCTGCTATA AGATTTCGTG        360
CAGACAATCC AGGGGTTTGG TTCATGCACT GTCATTTGGA GGTTCACACA TCGTGGGGAC       420
TGAAAATGGC GTGGGTAGTA AAGAACGGAA AAGGGCCCAT CGATTTTCCA CCCGGGTGGG       480
TACCAGTAA                                                              489
```

(2) INFORMATION FOR SEQ ID NO:83:

(i) SEQUENCE CHARACTERISTICS:
       (A) LENGTH: 471 base pairs
       (B) TYPE: nucleic acid
       (C) STRANDEDNESS: single
       (D) TOPOLOGY: linear (xi) SEQUENCE DESCRIPTION: SEQ ID NO:83:

```
GAATTCGGCA CGAGAAAACC TTTTCAGACG AATGTTCTGA TGCTCGGCCC CGGCCAGACA        60
ACAGACATAC TTCTCACTGC CAATCAGGCT ACAGGTAGAT ACTACATGGC TGCTCGAGCA       120
TATTCCAACG GGCAAGGAGT TCCCTTCGAT AACACCACTA CCACTGCCAT TTTAGAATAC       180
GAGGGAAGCT CTAAGACTTC AACTCCAGTC ATGCCTAATC TTCCATTCTA TAACGACACC       240
AACAGTGCTA CTAGCTTCGC TAATGGTCTT AGAAGCTTGG GCTCACACGA CCACCCAGTC       300
TTCGTTCCTC AGAGTGTGGA GGAGAATCTG TTCTACACCA TCGGTTTGGG GTTGATCAAA       360
TGTCCGGGGC AGTCTTGTGG AGGTCCAACG GATCAAGATT TGCAGCAAGT ATGAATACAT       420
ATCATTTGTC CCGCAACCAC TTCTTCCAAT CCTTCAAGCT CAGCATTTTG G                471
```

(2) INFORMATION FOR SEQ ID NO:84:

(i) SEQUENCE CHARACTERISTICS:
       (A) LENGTH: 338 base pairs
       (B) TYPE: nucleic acid
       (C) STRANDEDNESS: single
       (D) TOPOLOGY: linear (xi) SEQUENCE DESCRIPTION: SEQ ID NO:84:

```
GTTCGGCACT GAGAGATCCA TTTCTTTCAA TGTTGAGACA GTGAGTAGTA TTAGTTTGAT        60
ATCTCTTTCA GGAATATATC GTGCTTGCAG GATCTTTAGT TTCTGCAACA ATGTCGTTGC       120
AATCAGTGCG TCTATCTTCT GCTCTCCTTG TTTTGCTACT AGCATTTGTT GCTTACTTAG       180
TTGCTGTAAC AAACGCAGAT GTCCACAATT ATACCTTCAT TATTAGAAAG AGACAGTTAC       240
CAGGCTATGC AATAAGCGTA TAATCGCCAC CGTCAATGGC AGCTACCAGG CCCAACTATT       300
CATGTACGTG ATGGAGACGT TGTTAATTAT CAAAGCTT                               338
```

(2) INFORMATION FOR SEQ ID NO:85:

(i) SEQUENCE CHARACTERISTICS:
       (A) LENGTH: 1229 base pairs
       (B) TYPE: nucleic acid
       (C) STRANDEDNESS: single (D) TOPOLOGY: linear (xi) SEQUENCE DESCRIPTION: SEQ ID NO:85:

| | | | | | |
|---|---|---|---|---|---|
| AGAGAAATAA | TTATATTTGT | AAATTTAAGT | CTACGTTTAT | TAAAAAACTA | CAACCCTAAA | 60 |
| TGCAGGAGAA | AAAACAAGCA | TGCTGTCTAC | TGAAGCTTAC | AAATCAAATC | CCTGCGATAT | 120 |
| GTCTTTTCTC | GTGCCGAATT | CGGCACGAGA | AGATCTTGGT | TCGAGTCTCT | CAGCTCTCTC | 180 |
| CAAAGGAATT | TTGTGGGTCA | TTTGCAGGTG | AAGACACCAT | GGTGAAGGCT | TATCCCACCG | 240 |
| TAAGCGAGGA | GTACAAGGCT | GCCATTGACA | AATGCAAGAG | GAAGCTCCGA | GCTCTCATTG | 300 |
| CAGAGAAGAA | CTGTGCGCCG | ATCATGGTTC | GAATCGCATG | GCACAGCGCT | GGGACTTACG | 360 |
| ATGTCAAGAC | CAAGACCGGA | GGGCCCTTCG | GGACGATGAG | ATATGGGGCC | GAGCTTGCCC | 420 |
| ACGGTGCTAA | CAGTGGTCTG | GACATCGCAG | TTAGGCTCCT | GGAGCCAATC | AAGGAACAGT | 480 |
| TCCCCATAAT | CACCTATGCT | GACCTTTATC | AGTTGGCTGG | TGTGGTGGCT | GTTGAAGTGA | 540 |
| CCGGGGGACC | TGACATTCCG | TTCCATCCTG | GAAGAGAAGA | CAAGCCTGAG | CCTCCAGAAG | 600 |
| AAGGCCGCCT | TCCTGATGCT | ACAAAAGGAC | CTGATCATCT | GAGGGATGTT | TTTGGTCACA | 660 |
| TGGGGTTGAA | TGATAAGGAA | ATTGTGGCCT | TGTCTGGTGC | CCACACCTTG | GGGAGATGCC | 720 |
| ACAAGGAGAG | ATCTGGTTTT | GAAGGACCAT | GGACCTCTAA | CCCCCTTATC | TTTGACAACT | 780 |
| CTTACTTCAC | AGAGCTTGTG | ACTGGAGAGA | AGGAAGGCCT | GCTTCAGTTG | CCATCTGATA | 840 |
| AGGCACTGCT | TGCTGATCCT | AGTTTTGCAG | TTTATGTTCA | GAAGTATGCA | CAGGACGAAG | 900 |
| ACGCTTTCTT | TGCTGACTAT | GCGGAAGCTC | ACCTGAAGCT | TTCTGAACTT | GGGTTTGCTG | 960 |
| ATGCGTAGAT | TCATACCTTC | TGCAGAGACA | ATTCCTTGCT | AGATAGCTTC | GTTTTGTATT | 1020 |
| TCATCTAATC | TTTTCGATTA | TATAGTCACA | TAGAAGTTGG | TGTTATGCGC | CATAGTGATA | 1080 |
| CTTGAACCTA | CATGTTTTTG | AAAAGTATCG | ATGTTCTTTA | AAATGAACAT | TGAATACAAC | 1140 |
| ATTTTGGAAT | CTGGTTGTGT | TCTATCAAGC | GCATATTTTA | ATCGAATGCT | TCGTTCCTGT | 1200 |
| TAAAAAAAAA | AATAAAATAA | AAAAAAAA | | | | 1229 |

(2) INFORMATION FOR SEQ ID NO:86:

(i) SEQUENCE CHARACTERISTICS:
        (A) LENGTH: 1410 base pairs
        (B) TYPE: nucleic acid
        (C) STRANDEDNESS: single
        (D) TOPOLOGY: linear (xi) SEQUENCE DESCRIPTION: SEQ ID NO:86:

| | | | | | |
|---|---|---|---|---|---|
| GAAGATGGGG | CTGTGGGTGG | TGCTGGCTTT | GGCGCTCAGT | GCGCACTATT | GCAGTCTCAG | 60 |
| GCTTACAATG | TGGTAAGTTC | AAGCAATGCT | ACTGGGAGTT | ACAGTGAGAA | TGGATTGGTG | 120 |
| ATGAATTACT | ATGGGGACTC | TTGCCCTCAG | GCTGAAGAGA | TCATTGCTGA | CAAGTACGC | 180 |
| CTGTTGTACA | AAAGACACAA | GAACACTGCA | TTCTCATGGC | TTAGAAATAT | TTTCCATGAC | 240 |
| TGTGCTGTGG | AGTCATGTGA | TGCATCGCTT | CTGTTGGACT | CAACAAGGAA | CAGCATATCA | 300 |
| GAAAAGGACA | CTGACAGGAG | CTTCGGCCTC | CGCAACTTTA | GGTATTTGGA | TACCATCAAG | 360 |
| GAAGCCGTGG | AGAGGGAGTG | CCCCGGGGTC | GTTTCCTGTG | CAGATATACT | CGTTCTCTCT | 420 |
| GCCAGAGATG | GCGTTGTATC | GTTGGGAGGA | CCATACATTC | CCCTGAAGAC | GGGAAGAAGA | 480 |
| GATGGACGGA | AGAGCAGAGC | AGATGTGGTG | GAGAATTACC | TGCCCGATCA | CAATGAGAGC | 540 |
| ATCTCCACTG | TTCTGTCTCG | CTTCAAAGCC | ATGGGAATCG | ACACCCGTGG | GGTTGTTGCA | 600 |
| CTGCTGGGGG | CTCACAGCGT | GGGGAGGACT | CACTGCGTGA | AGCTGGTGCA | CAGGCTGTAC | 660 |
| CCGGAAGTAG | ATCCGACACT | GGACCCTGGG | CACGTGGAGC | ACATGAAGCA | CAAGTGCCCG | 720 |

```
GACGCGATCC CCAACCCGAA GGCAGTGCAG TATGTGCGGA ACGACCGGGG AACGCCTATG     780

AAGCTGGACA ACAACTACTA CGTGAACCTG ATGAACAACA AGGGGCTCCT AATAGTGGAC     840

CAGCAACTGT ATGCAGATTC GAGGACCAGG CCGTATGTGA AGAAGATGGC AAAAAGCCAG     900

GAATACTTCT TCAAATACTT CTCCCGGGCG CTCACCATCC TCTCTGAGAA CAATCCTCTC     960

ACCGGCGCTC GAGGAGAAAT CCGTCGGCAG TGCTCGCTCA AAAACAAATT GCACACAAAA    1020

AGCAAGCGTT GAGCGATAGC TCAATGCCGC AGTGGTGGGA GTGATAGCGT GATGCCACAG    1080

TGGTGGGCAT TTCATATATA AATTGCAGTT TGCGTTTTTA TTAGATAATC ATAATGGTGT    1140

GGTGTGACTA TGCCCTGCGA ATCACATCGA TGAACCACAA CCGAACCGTG AACAGTAGG     1200

CTTATTCCCT TATGTAAGCA GAACCTTTTA TTATAAGCAA AAAAGACAAT CCTGTCTGTT    1260

ATTCTAGTAT AATTTTGTCA TCAGTTAAAG TTGCTCATCT GATAATAACT GGAAACGGTA    1320

AAATATGACA ACTACGTATC TTCTTTGGTC ATCTGATAAT AACCGGAAAC GATAAAATAT    1380

GACAACTACA TATATTCTTT AAAAAAAAAA                                    1410
```

(2) INFORMATION FOR SEQ ID NO:87:

(i) SEQUENCE CHARACTERISTICS:
        (A) LENGTH: 687 base pairs
        (B) TYPE: nucleic acid
        (C) STRANDEDNESS: single
        (D) TOPOLOGY: linear (xi) SEQUENCE DESCRIPTION: SEQ ID NO:87:

```
GTAGTTTCGT TTTACAACAA TCTCAGGTTT TGAATCTCAG AATAGTTGCG AAAGGAAGCG      60

ATGACGAAGT ACGTGATCGT TAGCTCCATT GTGTGTTTCT TTGTATTTGT TTCTGCGTGC     120

ATAATTTCTG TCAATGGATT AGTTGTCCAT GAAGATGATC TGTCAAAGCC TGTGCATGGG     180

CTTTCGTGGA CATTTTATAA GGACAGTTGC CCCGACTTGG AGGCCATAGT GAAATCGGTA     240

CTTGAGCCGG CGTTGGACGA AGATATCACT CAGGCCGCAG GCTTGCTGAG ACTTCATTTC     300

CATGACTGTT TTGTGCAGGG TTGCGATGGG TCCGTGTTGC TGACAGGAAC TAAAAGAAAC     360

CCCAGTGAGC AACAGGCTCA GCCAAACTTA ACACTAAGAG CCCGGGCCTT GCAGCTGATC     420

GACGAAATTA AAACCGCTGT AGAAGCTAGC TGCAGTGGGG TTGTAACTTG TGCAGACATT     480

CTGGCTTTGG CTGCTCGTGA CTCCGTCCGC TCAGGAGGCC CAAAATTTCC AGTACCACTT     540

GGCCGCAGAG ATAGCCTAAA GTTTGCCAGT CAATCCGTAG TTCTCGCCAA TATACCAACT     600

CCAACTTTAA ATTTGACACA GCTGATGAAC ATTTTTGGCT CCAAAGGATT CAGTTTGGCC     660

GAAATGGTTG CTCTTCAGGT GGCACAC                                        687
```

(2) INFORMATION FOR SEQ ID NO:88:

(i) SEQUENCE CHARACTERISTICS:
        (A) LENGTH: 688 base pairs
        (B) TYPE: nucleic acid
        (C) STRANDEDNESS: single
        (D) TOPOLOGY: linear (xi) SEQUENCE DESCRIPTION: SEQ ID NO:88:

```
GTAGTTTCGT TTTACAACAA TCTACAGGTT TTGAATCTCA GAATAGTTGC GAAAGGAAGC      60

GATGACGAAG TACGTGATCG TTAGCTCCAT TGTATGTTTC TTTGTATTTG TTTCTGCGTG     120

CATAATTTCT GTCAATGGAT TAGTTGTCCA TGAAGATGAT CTGTCAAAGC TGTGCATGG      180

GCTTTCGTGG ACATTTTATA AGGACAGTTG CCCCGACTTG GAGGCCATAG TGAAATCGGT     240

ACTTGAGCCG GCGTTGGACG AAGATATCAC TCAGGCCGCA GGTTGCTGAG ACTTCATTTC     300
```

```
CATGACTGTT TTGTGCAGGG TTGCGATGGG TCCGTGTTGC TGACAGGAAC TAAAAGAAAC       360

CCCCGAGTGA GCAACAGGCT CAGCCAAACT TAACACTAAG AGCCCGGGCC TTGCAGCTGA       420

TCGACGAAAT TAAAACCGCT GTAGAAGCTA GCTGCAGTGG GGTTGTAACT TGTGCAGACA       480

TTCTGGCTTT GGCTGCTCGT GACTCCGTCG CTCAGGAGGC CCAAAATTTC CAGTACCACT       540

TGGCCGCAGA GATAGCCTAA AGTTTGCCAG TCAATCCGTA GTTCTCGCCA ATATACCAAC       600

TCCAACTTTA AATTTGACAC AGCTGATGAA CATTTTTGGC TCCAAAGGAT TCAGTTTGGC       660

CGAAATGGTT GCTCTTCAGG TGGCACAC                                         688
```

MATERIALS AND METHODS FOR THE MODIFICATION OF PLANT LIGNIN CONTENT

CROSS-REFERENCE TO RELATED APPLICATIONS

This application is a continuation-in-part of U.S. patent application Ser. No. 08/713,000, filed Sep. 11, 1996 now U.S. Pat. No. 5,850,020, issued Dec. 15, 1998.

TECHNICAL FIELD OF THE INVENTION

This invention relates to the field of modification of lignin content and composition in plants. More particularly, this invention relates to enzymes involved in the lignin biosynthetic pathway and nucleotide sequences encoding such enzymes.

BACKGROUND OF THE INVENTION

Lignin is an insoluble polymer which is primarily responsible for the rigidity of plant stems. Specifically, lignin serves as a matrix around the polysaccharide components of some plant cell walls. The higher the lignin content, the more rigid the plant. For example, tree species synthesize large quantities of lignin, with lignin constituting between 20% to 30% of the dry weight of wood. In addition to providing rigidity, lignin aids in water transport within plants by rendering cell walls hydrophobic and water impermeable. Lignin also plays a role in disease resistance of plants by impeding the penetration and propagation of pathogenic agents.

The high concentration of lignin in trees presents a significant problem in the paper industry wherein considerable resources must be employed to separate lignin from the cellulose fiber needed for the production of paper. Methods typically employed for the removal of lignin are highly energy- and chemical-intensive, resulting in increased costs and increased levels of undesirable waste products. In the U.S. alone, about 20 million tons of lignin are removed from wood per year.

Lignin is largely responsible for the digestibility, or lack thereof, of forage crops, with small increases in plant lignin content resulting in relatively high decreases in digestibility. For example, crops with reduced lignin content provide more efficient forage for cattle, with the yield of milk and meat being higher relative to the amount of forage crop consumed. During normal plant growth, the increase in dry matter content is accompanied by a corresponding decrease in digestibility. When deciding on the optimum time to harvest forage crops, farmers must therefore chose between a high yield of less digestible material and a lower yield of more digestible material.

For some applications, an increase in lignin content is desirable since increasing the lignin content of a plant would lead to increased mechanical strength of wood, changes in its color and increased resistance to rot. Mycorrhizal species composition and abundance may also be favorably manipulated by modifying lignin content and structural composition.

As discussed in detail below, lignin is formed by polymerization of at least three different monolignols which are synthesized in a multistep pathway, each step in the pathway being catalyzed by a different enzyme. It has been shown that manipulation of the number of copies of genes encoding certain enzymes, such as cinnamyl alcohol dehydrogenase (CAD) and caffeic acid 3-O-methyltransferase (COMT) results in modification of the amount of lignin produced; see, for example, U.S. Pat. No. 5,451,514 and PCT publication no. WO 94/23044. Furthermore, it has been shown that antisense expression of sequences encoding CAD in poplar leads to the production of lignin having a modified composition (Grand, C. et al. *Planta* (Berl.) 163:232–237 (1985)).

While DNA sequences encoding some of the enzymes involved in the lignin biosynthetic pathway have been isolated for certain species of plants, genes encoding many of the enzymes in a wide range of plant species have not yet been identified. Thus there remains a need in the art for materials useful in the modification of lignin content and composition in plants and for methods for their use.

SUMMARY OF THE INVENTION

Briefly, the present invention provides isolated DNA sequences obtainable from eucalyptus and pine which encode enzymes involved in the lignin biosynthetic pathway, DNA constructs including such sequences, and methods for the use of such constructs. Transgenic plants having altered lignin content and composition are also provided.

In a first aspect, the present invention provides isolated DNA sequences coding for the following enzymes isolated from eucalyptus and pine: cinnamate 4-hydroxylase (C4H), coumarate 3-hydroxylase (C3H), phenolase (PNL), O-methyl transferase (OMT), cinnamyl alcohol dehydrogenase (CAD), cinnamoyl-CoA reductase (CCR), phenylalanine ammonia-lyase (PAL), 4-coumarate:CoA ligase (4CL), coniferol glucosyl transferase (CGT), coniferin beta-glucosidase (CBG), laccase (LAC) and peroxidase (POX), together with ferulate-5-hydroxylase (F5H) from eucalyptus. In one embodiment, the isolated DNA sequences comprise a nucleotide sequence selected from the group consisting of: (a) sequences recited in SEQ ID NO: 16–70 and 72–88; (b) complements of the sequences recited in SEQ ID NO: 16–70 and 72–88; (c) reverse complements of the sequences recited in SEQ ID NO: 16–70 and 72–88; (d) reverse sequences of the sequences recited in SEQ ID NO: 16–70 and 72–88; and (e) sequences having at least about a 99% probability of being the same as a sequence of (a)–(d) as measured by the computer algorithm FASTA.

In another aspect, the invention provides DNA constructs comprising a DNA sequence of the present invention, either alone, in combination with one or more of the inventive sequences, or in combination with one or more known DNA sequences; together with transgenic cells comprising such constructs.

In a related aspect, the present invention provides DNA constructs comprising, in the 5'-3' direction, a gene promoter sequence; an open reading frame coding for at least a functional portion of an enzyme encoded by an inventive DNA sequence or variants thereof;

and a gene termination sequence. The open reading frame may be orientated in either a sense or antisense direction. DNA constructs comprising a non-coding region of a gene coding for an enzyme encoded by the above DNA sequences or a nucleotide sequence complementary to a non-coding region, together with a gene promoter sequence and a gene termination sequence, are also provided. Preferably, the gene promoter and termination sequences are functional in a host plant. Most preferably, the gene promoter and termination sequences are those of the original enzyme genes but others generally used in the art, such as the Cauliflower Mosaic Virus (CMV) promoter, with or without enhancers, such as the Kozak sequence or Omega enhancer, and *Agro-* bacterium tumefaciens nopalin synthase terminator may be usefully employed in the present invention. Tissue-specific promoters may be employed in order to target expression to one or more desired tissues. In a preferred embodiment, the gene promoter sequence provides for transcription in xylem. The DNA construct may further include a marker for the identification of transformed cells.

In a further aspect, transgenic plant cells comprising the DNA constructs of the present invention are provided, together with plants comprising such transgenic cells, and fruits and seeds of such plants.

In yet another aspect, methods for modulating the lignin content and composition of a plant are provided, such methods including stably incorporating into the genome of the plant a DNA construct of the present invention. In a preferred embodiment, the target plant is a woody plant, preferably selected from the group consisting of eucalyptus and pine species, most preferably from the group consisting of *Eucalyptus grandis* and *Pinus radiata*. In a related aspect, a method for producing a plant having altered lignin content is provided, the method comprising transforming a plant cell with a DNA construct of the present invention to provide a transgenic cell, and cultivating the transgenic cell under conditions conducive to regeneration and mature plant growth.

In yet a further aspect, the present invention provides methods for modifying the activity of an enzyme in a plant, comprising stably incorporating into the genome of the plant a DNA construct of the present invention. In a preferred embodiment, the target plant is a woody plant, preferably selected from the group consisting of eucalyptus and pine species, most preferably from the group consisting of *Eucalyptus grandis* and *Pinus radiata*.

The above-mentioned and additional features of the present invention and the manner of obtaining them will become apparent, and the invention will be best understood by reference to the following more detailed description, read in conjunction with the accompanying drawing.

DETAILED DESCRIPTION

Figure 1:
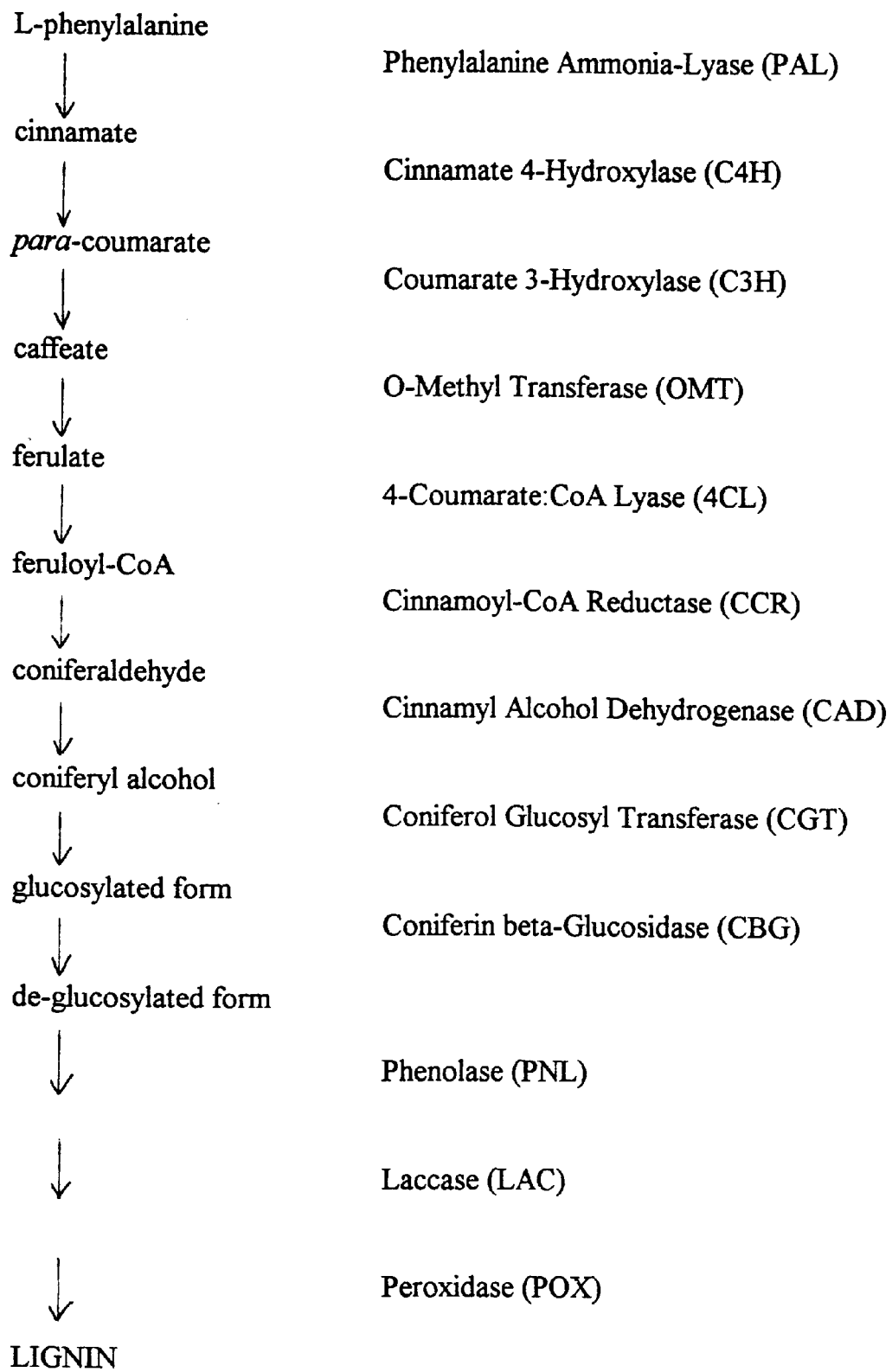
FIG. 1 is a schematic overview of the lignin biosynthetic pathway.

Lignin is formed by polymerization of at least three different monolignols, primarily para-coumaryl alcohol, coniferyl alcohol and sinapyl alcohol. While these three types of lignin subunits are well known, it is possible that slightly different variants of these subunits may be involved in the lignin biosynthetic pathway in various plants. The relative concentration of these residues in lignin varies between different plant species and within species. In addition, the composition of lignin may also vary between different tissues within a specific plant. The three monolignols are derived from phenylalanine in a multistep process and are believed to be polymerized into lignin by a free radical mechanism.

FIG. 1 shows the different steps in the biosynthetic pathway for coniferyl alcohol together with the enzymes responsible for catalyzing each step. para-Coumaryl alcohol and sinapyl alcohol are synthesized by similar pathways. Phenylalanine is first deaminated by phenylalanine ammonia-lyase (PAL) to give cinnamate which is then hydroxylated by cinnamate 4-hydroxylase (C4H) to form p-coumarate. p-Coumarate is hydroxylated by coumarate 3-hydroxylase to give caffeate. The newly added hydroxyl group is then methylated by O-methyl transferase (OMT) to give ferulate which is conjugated to coenzyme A by 4-coumarate:CoA ligase (4CL) to form feruloyl-CoA. Reduction of feruloyl-CoA to coniferaldehyde is catalyzed by cinnamoyl-CoA reductase (CCR). Coniferaldehyde is further reduced by the action of cinnamyl alcohol dehydrogenase (CAD) to give coniferyl alcohol which is then converted into its glucosylated form for export from the cytoplasm to the cell wall by coniferol glucosyl transferase (CGT). Following export, the de-glucosylated form of coniferyl alcohol is obtained by the action of coniferin beta-glucosidase (CBG). Finally, polymerization of the three monolignols to provide lignin is catalyzed by phenolase (PNL), laccase (LAC) and peroxidase (POX).

The formation of sinapyl alcohol involves an additional enzyme, ferulate-5-hydroxylase (F5H). For a more detailed review of the lignin biosynthetic pathway, see: Whetton, R. and Sederoff, R., *The Plant Cell*, 7:1001–1013 (1995).

Quantitative and qualitative modifications in plant lignin content are known to be induced by external factors such as light stimulation, low calcium levels and mechanical stress. Synthesis of new types of lignins, sometimes in tissues not normally lignified, can also be induced by infection with pathogens. In addition to lignin, several other classes of plant products are derived from phenylalanine, including flavonoids, coumarins, stilbenes and benzoic acid derivatives, with the initial steps in the synthesis of all these compounds being the same. Thus modification of the action of PAL, C4H and 4CL may affect the synthesis of other plant products in addition to lignin.

Using the methods and materials of the present invention, the lignin content of a plant can be increased by incorporating additional copies of genes encoding enzymes involved in the lignin biosynthetic pathway into the genome of the target plant. Similarly, a decrease in lignin content can be obtained by transforming the target plant with antisense copies of such genes. In addition, the number of copies of genes encoding for different enzymes in the lignin biosynthetic pathway can be manipulated to modify the relative amount of each monolignol synthesized, thereby leading to the formation of lignin having altered composition. The alteration of lignin composition would be advantageous, for example, in tree processing for paper, and may also be effective in altering the palatability of wood materials to rotting fungi.

In one embodiment, the present invention provides isolated complete or partial DNA sequences encoding, or partially encoding, enzymes involved in the lignin biosynthetic pathway, the DNA sequences being obtainable from eucalyptus and pine. Specifically, the present invention provides isolated DNA sequences encoding the enzymes CAD (SEQ ID NO: 1, 30), PAL (SEQ ID NO: 16), C4H (SEQ ID NO: 17), C3H (SEQ ID NO: 18), F5H (SEQ ID NO: 19–21), OMT (SEQ ID NO: 22–25), CCR (SEQ ID NO: 26–29), CGT (SEQ ID NO: 31–33), CBG (SEQ ID NO: 34), PNL (SEQ ID NO: 35, 36), LAC (SEQ ID NO: 37–41) and POX (SEQ ID NO: 42–44) from *Eucalyptus grandis*; and the enzymes C4H (SEQ ID NO: 2, 3, 48, 49), C3H (SEQ ID NO: 4, 50–52), PNL (SEQ ID NO: 5, 81), OMT (SEQ ID NO: 6, 53–55), CAD (SEQ ID NO: 7, 71), CCR (SEQ ID NO: 8, 58–70), PAL (SEQ ID NO: 9–11,45–47), 4CL (SEQ ID NO: 12, 56, 57), CGT (SEQ ID NO: 72), CBG (SEQ ID NO: 73–80), LAC (SEQ ID NO: 82–84) and POX (SEQ ID NO: 13, 85–88) from *Pinus radiata*. Complements of such isolated DNA sequences, reverse complements of such isolated DNA sequences and reverse sequences of such isolated DNA sequences, together with variants of such sequences, are also provided. DNA sequences encompassed by the present invention include cDNA, genomic DNA, recombinant DNA and wholly or partially chemically synthesized DNA molecules.

The definition of the terms "complement", "reverse complement" and "reverse sequence", as used herein, is best illustrated by the following example. For the sequence 5' AGGACC 3', the complement, reverse complement and reverse sequence are as follows:

| complement | 3' TCCTGG 5' |
|---|---|
| reverse complement | 3' GGTCCT 5' |
| reverse sequence | 5' CCAGGA 3'. |

As used herein, the term "variant" covers any sequence which exhibits at least about 50%, more preferably at least about 70% and, more preferably yet, at least about 90% identity to a sequence of the present invention. Most preferably, a "variant" is any sequence which has at least about a 99% probability of being the same as the inventive sequence. The probability for DNA sequences is measured by the computer algorithm FASTA (version 2.0u4, February 1996; Pearson W. R. et al., *Proc. Natl. Acad. Sci.*, 85:2444–2448, 1988), the probability for translated DNA sequences is measured by the computer algorithm TBLASTX and that for protein sequences is measured by the computer algorithm BLASTP (Altschul, S. F. et al. *J. Mol. Biol.*, 215:403–410, 1990). The term "variants" thus encompasses sequences wherein the probability of finding a match by chance (smallest sum probability) in a database, is less than about 1% as measured by any of the above tests.

Variants of the isolated sequences from other eucalyptus and pine species, as well as from other commercially important species utilized by the lumber industry, are contemplated. These include the following gymnosperms, by way of example:

loblolly pine *Pinus taeda*, slash pine *Pinus elliotti*, sand pine *Pinus clausa*, longleaf pine *Pinus palustrus*, shortleaf pine *Pinus echinata*, ponderosa pine *Pinus ponderosa*, Jeffrey pine *Pinus jeffrey*, red pine *Pinus resinosa*, pitch pine *Pinus rigida*, jack pine *Pinus banksiana*, pond pine *Pinus serotina*, Eastern white pine *Pinus strobus*, Western white pine *Pinus monticola*, sugar pine *Pinus lambertiana*, Virginia pine *Pinus virginiana*, lodgepole pine *Pinus contorta*, Caribbean pine *Pinus caribaea*, *P. pinaster*, Calabrian pine *P. brutia*, Afghan pine *P. eldarica*, Coulter pine *P. coulteri*, European pine *P. nigra* and *P. sylvestris*; Douglas-fir *Pseudotsuga menziesii*; the hemlocks which include Western hemlock *Tsuga heterophylla*, Eastern hemlock *Tsuga canadensis*, Mountain hemlock *Tsuga mertensiana*; the spruces which include the Norway spruce *Picea abies*, red spruce *Picea rubens*, white spruce *Picea glauca*, black spruce *Picea mariana*, Sitka spruce *Picea sitchensis*, Englemann spruce *Picea engelmanni*, and blue spruce *Picea pungens*; redwood *Sequoia sempervirens*; the true firs include the Alpine fir *Abies lasiocarpa*, silver fir *Abies amabilis*, grand fir *Abies grandis*, nobel fir *Abies procera*, white fir *Abies concolor*, California red fir *Abies magnifica*, and balsam fir *Abies balsamea*, the cedars which include the Western red cedar *Thuja plicata*, incense cedar *libocedrus decurrens*, Northern white cedar *Thuja occidentalis*, Port Orford cedar *Chamaecyparis lawsoniona*, Atlantic white cedar *Chamaecyparis thyoides*, Alaska yellow-cedar *Chamaecyparis nootkatensis*, and Eastern red cedar *Huniperus virginiana*; the larches which include Eastern larch *Larix laricina*, Western larch *Larix occidentalis*, European larch *Larix decidua*, Japanese larch *Larix leptolepis*, and Siberian larch *Larix siberica*; bold cypress *Taxodium distichum* and Giant sequoia *Sequoia gigantea*; and the following angiosperms, by way of example:

*Eucalyptus alba, E. bancroftii, E. botyroides, E. bridgesiana, E. calophylla, E. camaldulensis, E. citriodora, E. cladocalyx, E. coccifera, E. curtisii, E. dalrympleana, E. deglupta, E. delagatensis, E. diversicolor, E. dunnii, E. ficifolia, E. globulus, E. gomphocephala, E. gunnii, E. henryi, E. laevopinea, E. macarthurii, E. macrorhyncha, E. maculata, E. marginata, E. megacarpa, E. melliodora, E. nicholii, E. nitens, E. nova-angelica, E. obliqua, E. obtusiflora, E. oreades, E pauciflora, E. polybractea, E. regnans, E. resinifera, E. robusta, E. rudis, E. saligna, E. sideroxylon, E. stuartiana, E. tereticornis, E. torelliana, E. urnigera, E. urophylla, E. viminalis, E. viridis, E. wandoo* and *E. youmanni*.

The inventive DNA sequences may be isolated by high throughput sequencing of cDNA libraries prepared from *Eucalyptus grandis* and *Pinus radiata* as described below in Examples 1 and 2. Alternatively, oligonucleotide probes based on the sequences provided in SEQ ID NO: 1–13 and 16–88 can be synthesized and used to identify positive clones in either cDNA or genomic DNA libraries from Eucalyptus grandis and Pinus radiata by means of hybridization or PCR techniques. Probes can be shorter than the sequences provided herein but should be at least about 10, preferably at least about 15 and most preferably at least about 20 nucleotides in length. Hybridization and PCR techniques suitable for use with such oligonucleotide probes are well known in the art. Positive clones may be analyzed by restriction enzyme digestion, DNA sequencing or the like.

In addition, the DNA sequences of the present invention may be generated by synthetic means using techniques well known in the art. Equipment for automated synthesis of oligonucleotides is commercially available from suppliers such as Perkin Elmer/Applied Biosystems Division (Foster City, Calif.) and may be operated according to the manufacturer's instructions.

In one embodiment, the DNA constructs of the present invention include an open reading frame coding for at least a functional portion of an enzyme encoded by a nucleotide sequence of the present invention or a variant thereof. As used herein, the "functional portion" of an enzyme is that portion which contains the active site essential for affecting the metabolic step, i.e. the portion of the molecule that is capable of binding one or more reactants or is capable of improving or regulating the rate of reaction. The active site may be made up of separate portions present on one or more polypeptide chains and will generally exhibit high substrate specificity. The term "enzyme encoded by a nucleotide sequence" as used herein, includes enzymes encoded by a nucleotide sequence which includes the partial isolated DNA sequences of the present invention.

For applications where amplification of lignin synthesis is desired, the open reading frame is inserted in the DNA construct in a sense orientation, such that transformation of a target plant with the DNA construct will lead to an increase in the number of copies of the gene and therefore an increase in the amount of enzyme. When down-regulation of lignin synthesis is desired, the open reading frame is inserted in the DNA construct in an antisense orientation, such that the RNA produced by transcription of the DNA sequence is complementary to the endogenous mRNA sequence. This, in turn, will result in a decrease in the number of copies of the gene and therefore a decrease in the amount of enzyme. Alternatively, regulation can be achieved by inserting appropriate sequences or subsequences (e.g. DNA or RNA) in ribozyme constructs.

In a second embodiment, the inventive DNA constructs comprise a nucleotide sequence including a non-coding region of a gene coding for an enzyme encoded by a DNA sequence of the present invention, or a nucleotide sequence complementary to such a non-coding region. As used herein the term "non-coding region" includes both transcribed sequences which are not translated, and non-transcribed sequences within about 2000 base pairs 5' or 3' of the translated sequences or open reading frames. Examples of non-coding regions which may be usefully employed in the inventive constructs include introns and 5'-non-coding leader sequences. Transformation of a target plant with such a DNA construct may lead to a reduction in the amount of lignin synthesized by the plant by the process of cosuppression, in a manner similar to that discussed, for example, by Napoli et al. (*Plant Cell* 2:279–290, 1990) and de Carvalho Niebel et al. (*Plant Cell* 7:347–358, 1995).

The DNA constructs of the present invention further comprise a gene promoter sequence and a gene termination sequence, operably linked to the DNA sequence to be transcribed, which control expression of the gene. The gene promoter sequence is generally positioned at the 5' end of the DNA sequence to be transcribed, and is employed to initiate transcription of the DNA sequence. Gene promoter sequences are generally found in the 5' non-coding region of a gene but they may exist in introns (Luehrsen, K. R., *Mol. Gen. Genet.* 225:81–93, 1991) or in the coding region, as for example in PAL of tomato (Bloksberg, 1991 Studies on the Biology of Phenylalanine Ammonia Lyase and Plant Pathogen Interaction. Ph.D. Thesis, Univ. of California, Davis, University Microfilms International order number 9217564). When the construct includes an open reading frame in a sense orientation, the gene promoter sequence also initiates translation of the open reading frame. For DNA constructs comprising either an open reading frame in an antisense orientation or a non-coding region, the gene promoter sequence consists only of a transcription initiation site having a RNA polymerase binding site.

A variety of gene promoter sequences which may be usefully employed in the DNA constructs of the present invention are well known in the art. The promoter gene sequence, and also the gene termination sequence, may be endogenous to the target plant host or may be exogenous, provided the promoter is functional in the target host. For example, the promoter and termination sequences may be from other plant species, plant viruses, bacterial plasmids and the like. Preferably, gene promoter and termination sequences are from the inventive sequences themselves.

Factors influencing the choice of promoter include the desired tissue specificity of the construct, and the timing of transcription and translation. For example, constitutive promoters, such as the 35S Cauliflower Mosaic Virus (CaMV 35S) promoter, will affect the activity of the enzyme in all parts of the plant. Use of a tissue specific promoter will result in production of the desired sense or antisense RNA only in the tissue of interest. With DNA constructs employing inducible gene promoter sequences, the rate of RNA polymerase binding and initiation can be modulated by external stimuli, such as light, heat, anaerobic stress, alteration in nutrient conditions and the like. Temporally regulated promoters can be employed to effect modulation of the rate of RNA polymerase binding and initiation at a specific time during development of a transformed cell. Preferably, the original promoters from the enzyme gene in question, or promoters from a specific tissue-targeted gene in the organism to be transformed, such as eucalyptus or pine are used. Other examples of gene promoters which may be usefully employed in the present invention include, mannopine synthase (mas), octopine synthase (ocs) and those reviewed by Chua et al. (*Science*, 244:174–181, 1989).

The gene termination sequence, which is located 3' to the DNA sequence to be transcribed, may come from the same gene as the gene promoter sequence or may be from a different gene. Many gene termination sequences known in the art may be usefully employed in the present invention, such as the 3' end of the *Agrobacterium tumefaciens* nopaline synthase gene. However, preferred gene terminator sequences are those from the original enzyme gene or from the target species to be transformed.

The DNA constructs of the present invention may also contain a selection marker that is effective in plant cells, to allow for the detection of transformed cells containing the inventive construct. Such markers, which are well known in the art, typically confer resistance to one or more toxins. One example of such a marker is the NPTII gene whose expression results in resistance to kanamycin or hygromycin, antibiotics which are usually toxic to plant cells at a moderate concentration (Rogers et al. in *Methods for Plant Molecular Biology*, A. Weissbach and H. Weissbach, eds., Academic Press Inc., San Diego, Calif. (1988)). Alternatively, the presence of the desired construct in transformed cells can be determined by means of other techniques well known in the art, such as Southern and Western blots.

Techniques for operatively linking the components of the inventive DNA constructs are well known in the art and include the use of synthetic linkers containing one or more restriction endonuclease sites as described, for example, by Maniatis et al., (*Molecular Cloning: A Laboratory Manual*, Cold Spring Harbor Laboratories, Cold Spring Harbor, N.Y., 1989). The DNA construct of the present invention may be linked to a vector having at least one replication system, for example, *E. coli*, whereby after each manipulation, the resulting construct can be cloned and sequenced and the correctness of the manipulation determined.

The DNA constructs of the present invention may be used to transform a variety of plants, both monocotyledonous (e.g. grasses, corn, grains, oat, wheat and barley), dicotyledonous (e.g. Arabidopsis, tobacco, legumes, alfalfa, oaks, eucalyptus, maple), and Gymnosperms (e.g. Scots pine (Aronen, Finnish Forest Res. Papers, vol. 595, 1996), white spruce (Ellis et al., *Biotechnology* 11:94–92, 1993), larch (Huang et al., *In Vitro Cell* 27:201–207, 1991). In a preferred embodiment, the inventive DNA constructs are employed to transform woody plants, herein defined as a tree or shrub whose stem lives for a number of years and increases in diameter each year by the addition of woody tissue. Preferably the target plant is selected from the group consisting of eucalyptus and pine species, most preferably from the group consisting of *Eucalyptus grandis* and *Pinus radiata*. As discussed above, transformation of a plant with a DNA construct including an open reading frame coding for an enzyme encoded by an inventive DNA sequence wherein the open reading frame is orientated in a sense direction will generally lead to an increase in lignin content of the plant or, in some cases, to a decrease by cosuppression. Transformation of a plant with a DNA construct comprising an open reading frame in an antisense orientation or a non-coding (untranslated) region of a gene will generally lead to a decrease in the lignin content of the transformed plant.

Techniques for stably incorporating DNA constructs into the genome of target plants are well known in the art and include *Agrobacterium tumefaciens* mediated introduction, electroporation, protoplast fusion, injection into reproductive organs, injection into immature embryos, high velocity projectile introduction and the like. The choice of technique will depend upon the target plant to be transformed. For example, dicotyledonous plants and certain monocots and gymnosperms may be transformed by Agrobacterium Ti plasmid technology, as described, for example by Bevan (*Nucl. Acid Res.* 12:8711–8721, 1984). Targets for the introduction of the DNA constructs of the present invention include tissues, such as leaf tissue, disseminated cells, protoplasts, seeds, embryos, meristematic regions; cotyledons, hypocotyls, and the like. One preferred method for transforming eucalyptus and pine is a biolistic method using pollen (see, for example, Aronen 1996, Finnish Forest Res. Papers vol. 595, 53pp) or easily regenerable embryonic tissues. Other transformation techniques which may be usefully employed in the inventive methods include those taught by Ellis et al. (*Plant Cell Reports,* 8:16–20, 1989), Wilson et al. (*Plant Cell Reports* 7:704–707, 1989) and Tautorus et al. (*Theor. Appl. Genet.* 78:531–536, 1989).

Once the cells are transformed, cells having the inventive DNA construct incorporated in their genome may be selected by means of a marker, such as the kanamycin resistance marker discussed above. Transgenic cells may then be cultured in an appropriate medium to regenerate whole plants, using techniques well known in the art. In the case of protoplasts, the cell wall is allowed to reform under appropriate osmotic conditions. In the case of seeds or embryos, an appropriate germination or callus initiation medium is employed. For explants, an appropriate regeneration medium is used. Regeneration of plants is well established for many species. For a review of regeneration of forest trees see Dunstan et al., Somatic embryogenesis in woody plants. In: Thorpe, T. A. ed., 1995: in vitro embryogenesis of plants. Vol. 20 in Current Plant Science and Biotechnology in Agriculture, Chapter 12, pp. 471–540. Specific protocols for the regeneration of spruce are discussed by Roberts et al., (Somatic Embryogenesis of Spruce. In: *Synseed. Applications of synthetic seed to crop improvement*. Redenbaugh, K., ed. CRC Press, Chapter 23, pp. 427–449, 1993). The resulting transformed plants may be reproduced sexually or asexually, using methods well known in the art, to give successive generations of transgenic plants.

As discussed above, the production of RNA in target plant cells can be controlled by choice of the promoter sequence, or by selecting the number of functional copies or the site of integration of the DNA sequences incorporated into the genome of the target plant host. A target plant may be transformed with more than one DNA construct of the present invention, thereby modulating the lignin biosynthetic pathway for the activity of more than one enzyme, affecting enzyme activity in more than one tissue or affecting enzyme activity at more than one expression time. Similarly, a DNA construct may be assembled containing more than one open reading frame coding for an enzyme encoded by a DNA sequence of the present invention or more than one non-coding region of a gene coding for such an enzyme. The DNA sequences of the present invention may also be employed in combination with other known sequences encoding enzymes involved in the lignin biosynthetic pathway. In this manner, it may be possible to add a lignin biosynthetic pathway to a non-woody plant to produce a new woody plant.

The isolated DNA sequences of the present invention may also be employed as probes to isolate DNA sequences encoding enzymes involved in the lignin synthetic pathway from other plant species, using techniques well known to those of skill in the art.

The following examples are offered by way of illustration and not by way of limitation.

EXAMPLE 1

Isolation and Characterization of cDNA Clones from *Eucalyptus grandis*

Two *Eucalyptus grandis* cDNA expression libraries (one from a mixture of various tissues from a single tree and one from leaves of a single tree) were constructed and screened as follows.

mRNA was extracted from the plant tissue using the protocol of Chang et al. (*Plant Molecular Biology Reporter* 11:113–116 (1993)) with minor modifications. Specifically, samples were dissolved in CPC-RNAXB (100 mM Tris-Cl, pH 8,0; 25 mM EDTA; 2.0 M NaCl; 2% CTAB; 2% PVP and 0.05% Spermidine*3 HCl) and extracted with chloroform:isoamyl alcohol, 24:1. mRNA was precipitated with ethanol and the total RNA preparate was purified using a Poly(A) Quik mRNA Isolation Kit (Stratagene, La Jolla, Calif.). A cDNA expression library was constructed from the purified mRNA by reverse transcriptase synthesis followed by insertion of the resulting cDNA clones in Lambda ZAP using a ZAP Express cDNA Synthesis Kit (Stratagene), according to the manufacturer's protocol. The resulting cDNAs were packaged using a Gigapack II Packaging Extract (Stratagene) employing 1 $\mu$l of sample DNA from the 5 $\mu$l ligation mix. Mass excision of the library was done using XL 1-Blue MRF' cells and XLOLR cells (Stratagene) with ExAssist helper phage (Stratagene). The excised phagemids were diluted with NZY broth (Gibco BRL, Gaithersburg, Md.) and plated out onto LB-kanamycin agar plates containing X-gal and isopropylthio-beta-galactoside (IPTG).

Of the colonies plated and picked for DNA miniprep, 99% contained an insert suitable for sequencing. Positive colonies were cultured in NZY broth with kanamycin and cDNA was purified by means of alkaline lysis and polyethylene glycol (PEG) precipitation. Agarose gel at 1% was used to screen sequencing templates for chromosomal contamination. Dye primer sequences were prepared using a Turbo Catalyst 800 machine (Perkin Elmer/Applied Biosystems, Foster City, Calif.) according to the manufacturer's protocol.

DNA sequence for positive clones was obtained using an Applied Biosystems Prism 377 sequencer. cDNA clones were sequenced first from the 5' end and, in some cases, also from the 3' end. For some clones, internal sequence was obtained using subcloned fragments. Subcloning was performed using standard procedures of restriction mapping and subcloning to pBluescript II SK+vector.

The determined cDNA sequence was compared to known sequences in the EMBL database (release 46, March 1996) using the FASTA algorithm of February 1996 (version 2.0u4) (available on the Internet at the ftp site ftp://ftp.virginia.edu/pub/fasta/). Multiple alignments of redundant sequences were used to build up reliable consensus sequences. Based on similarity to known sequences from other plant species, the isolated DNA sequence (SEQ ID NO: 1) was identified as encoding a CAD enzyme.

In further studies, using the procedure described above, cDNA sequences encoding the following *Eucalyptus grandis* enzymes were isolated: PAL (SEQ ID NO: 16); C4H (SEQ ID NO: 17); C3H (SEQ ID NO: 18); F5H (SEQ ID NO: 19–21); OMT (SEQ ID NO: 22–25); CCR (SEQ ID NO: 26–29); CAD (SEQ ID NO: 30); CGT (SEQ ID NO: 31–33); CBG (SEQ ID NO: 34); PNL (SEQ ID NO: 35,36); LAC (SEQ ID NO: 37–41); and POX (SEQ ID NO: 42–44).

EXAMPLE 2

Isolation and Characterization of cDNA Clones from *Pinus radiata* a) Isolation of cDNA Clones by High Through-Put Screening

A *Pinus radiata* cDNA expression library was constructed from xylem and screened as described above in Example 1. DNA sequence for positive clones was obtained using forward and reverse primers on an Applied Biosystems Prism 377 sequencer and the determined sequences were compared to known sequences in the database as described above.

Based on similarity to known sequences from other plant species, the isolated DNA sequences were identified as encoding the enzymes C4H (SEQ ID NO: 2 and 3), C3H (SEQ ID NO: 4), PNL (SEQ ID NO: 5), OMT (SEQ ID NO: 6), CAD (SEQ ID NO: 7), CCR (SEQ ID NO: 8), PAL (SEQ ID NO: 9–11) and 4CL (SEQ ID NO: 12).

In further studies, using the procedure described above, additional cDNA clones encoding the following *Pinus radiata* enzymes were isolated: PAL (SEQ ID NO: 45–47); C4H (SEQ ID NO: 48, 49); C3H (SEQ ID NO: 50–52); OMT (SEQ ID NO: 53–55); 4CL (SEQ ID NO: 56, 57); CCR (SEQ ID NO: 58–70); CAD (SEQ ID NO: 71); CGT (SEQ ID NO: 72); CBG (SEQ ID NO: 73–80); PNL (SEQ ID NO: 81); LAC (SEQ ID NO: 82–84); and POX (SEQ ID NO: 85–88).

b) Isolation of cDNA Clones by PCR

Two PCR probes, hereinafter referred to as LNB010 and LNB011 (SEQ ID NO: 14 and 15, respectively) were designed based on conserved domains in the following peroxidase sequences previously identified in other species: vanpox, hvupox6, taepox, hvupox1, osapox, ntopox2, ntopox1, lespox, pokpox, luspox, athpox, hrpox, spopox, and tvepox (Genbank accession nos. D11337, M83671, X56011, X58396, X66125, J02979, D11396, X71593, D11102, L07554, M58381, X57564, Z22920, and Z31011, respectively).

RNA was isolated from pine xylem and first strand cDNA was synthesized as described above. This cDNA was subjected to PCR using 4 μM LNB010, 4 μM LNB011, 1×Kogen's buffer, 0.1 mg/ml BSA, 200 mM dNTP, 2 mM $Mg^{2+}$, and 0.1 U/μl of Taq polymerase (Gibco BRL). Conditions were 2 cycles of 2 min at 94° C. 1 min at 55° C. and 1 min at 72° C.; 25 cycles of 1 min at 94° C., 1 min at 55° C., and 1 min at 72° C. and 18 cycles of 1 min at 94° C., 1 min at 55° C., and 3 min at 72° C. in a Stratagene Robocycler. The gene was re-amplified in the same manner. A band of about 200 bp was purified from a TAE agarose gel using a Schleicher & Schuell Elu-Quik DNA purification kit and clones into a T-tailed pBluescript vector (Marchuk D. et al., *Nucleic Acids Res.* 19:1154, 1991). Based on similarity to known sequences, the isolated gene (SEQ ID NO: 13) was identified as encoding pine peroxidase (POX).

EXAMPLE 3

Use of an O-methyltransferase (OMT) Gene to Modify Lignin Biosynthesis a) Transformation of Tobacco Plants with a *Pinus radiata* OMT Gene Sense and anti-sense constructs containing a DNA sequence including the coding region of OMT (SEQ ID NO: 53) from *Pinus radiata* were inserted into *Agrobacterium tumefaciens* LBA4301 (provided as a gift by Dr. C. Kado, University of California, Davis, Calif.) by direct transformation using published methods (see, An G, Ebert PR, Mitra A, Ha SB: Binary Vectors. In: Gelvin SB, Schilperoort RA (eds) *Plant Molecular Biology Manual*, Kluwer Academic Publishers, Dordrecht (1988)). The presence and integrity of the transgenic constructs were verified by restriction digestion and DNA sequencing.

Tobacco (*Nicotiana tabacum* cv. Samsun) leaf sections were transformed using the method of Horsch et al. (*SCience*, 227:1229–1231, 1985). Five independent transformed plant lines were established for the sense construct and eight independent transformed plant lines were established for the anti-sense construct for OMT. Transformed plants containing the appropriate lignin gene construct were verified using Southern blot experiments. A "+" in the column labeled "Southern" in Table 1 below indicates that the transformed plant lines were confirmed as independent transformed lines.

b) Expression of Pinus OMT in Transformed Plants

Total RNA was isolated from each independent transformed plant line created with the OMT sense and anti-sense constructs. The RNA samples were analysed in Northern blot experiments to determine the level of expression of the transgene in each transformed line. The data shown in the column labeled "Northern" in Table 1 shows that the transformed plant lines containing the sense and anti-sense constructs for OMT all exhibited high levels of expression, relative to the background on the Northern blots. OMT expression in sense plant line number 2 was not measured because the RNA sample showed signs of degradation. There was no detectable hybridisation to RNA samples from empty vector-transformed control plants.

c) Modulation of OMT Enzyme Activity in Transformed Plants

The total activity of OMT enzyme, encoded by the Pinus OMT gene and by the endogenous tobacco OMT gene, in transformed tobacco plants was analysed for each transformed plant line created with the OMT sense and anti-sense constructs. Crude protein extracts were prepared from each transformed plant and assayed using the method of Zhang et al. (*Plant Physiol.*, 113:65–74, 1997). The data contained in the column labeled "Enzyme" in Table 1 shows that the transformed plant lines containing the OMT sense construct generally had elevated OMT enzyme activity, with a maximum of 199%, whereas the transformed plant lines containing the OMT anti-sense construct generally had reduced OMT enzyme activity, with a minimum of 35%, relative to empty vector-transformed control plants. OMT enzyme activity was not estimated in sense plant line number 3.

d) Effects of Pinus OMT on Lignin Concentration in Transformed Plants

The concentration of lignin in the transformed tobacco plants was determined using the well-established procedure of thioglycolic acid extraction (see, Freudenberg et al. in *Constitution and Biosynthesis of Lignin*, Springer-Verlag, Berlin, 1968). Briefly, whole tobacco plants, of an average age of 38 days, were frozen in liquid nitrogen and ground to a fine powder in a mortar and pestle. 100 mg of frozen powder from one empty vector-transformed control plant line, the five independent transformed plant lines containing the sense construct for OMT and the eight independent transformed plant lines containing the anti-sense construct for OMT were extracted individually with methanol, followed by 10% thioglycolic acid and finally dissolved in 1 M NaOH. The final extracts were assayed for absorbance at 280 nm. The data shown in the column labelled "TGA" in Table 1 shows that the transformed plant lines containing the sense and the anti-sense OMT gene constructs all exhibited significantly decreased levels of lignin, relative to the empty vector-transformed control plant lines.

TABLE 1

| plant line | transgene | orientation | Southern | Northern | Enzyme | TGA |
|---|---|---|---|---|---|---|
| 1 | control | na | + | blank | 100 | 104 |
| 1 | OMT | sense | + | 2.9E + 6 | 86 | 55 |
| 2 | OMT | sense | + | na | 162 | 58 |
| 3 | OMT | sense | + | 4.1E + 6 | na | 63 |
| 4 | OMT | sense | + | 2.3E + 6 | 142 | 66 |
| 5 | OMT | sense | + | 3.6E + 5 | 199 | 75 |
| 1 | OMT | anti-sense | + | 1.6E + 4 | 189 | 66 |
| 2 | OMT | anti-sense | + | 5.7E + 3 | 35 | 70 |
| 3 | OMT | anti-sense | + | 8.0E + 3 | 105 | 73 |
| 4 | OMT | anti-sense | + | 1.4E + 4 | 109 | 74 |
| 5 | OMT | anti-sense | + | 2.5E + 4 | 87 | 78 |
| 6 | OMT | anti-sense | + | 2.5E + 4 | 58 | 84 |
| 7 | OMT | anti-sense | + | 2.5E + 4 | 97 | 92 |
| 8 | OMT | anti-sense | + | 1.1E + 4 | 151 | 94 |

These data clearly indicate that lignin concentration, as measured by the TGA assay, can be directly manipulated by either sense or anti-sense expression of a lignin biosynthetic gene such as OMT.

EXAMPLE 4

Use of a 4-Coumarate:CoA ligase (4CL) Gene to Modify Lignin Biosynthesis a) Transformation of Tobacco Plants with a Pinus radiata 4CL Gene Sense and anti-sense constructs containing a DNA sequence including the coding region of 4CL (SEQ ID NO: 56) from Pinus radiata were inserted into Agrobacterium tumefaciens LBA4301 by direct transformation as described above. The presence and integrity of the transgenic constructs were verified by restriction digestion and DNA sequencing.

Tobacco (Nicotiana tabacum cv. Samsun) leaf sections were transformed as described above. Five independent transformed plant lines were established for the sense construct and eight independent transformed plant lines were established for the anti-sense construct for 4CL. Transformed plants containing the appropriate lignin gene construct were verified using Southern blot experiments. A "+" in the column labeled "Southern" in Table 2 indicates that the transformed plant lines listed were confirmed as independent transformed lines.

b) Expression of Pinus 4CL in Transformed Plants

Total RNA was isolated from each independent transformed plant line created with the 4CL sense and anti-sense constructs. The RNA samples were analysed in Northern blot experiments to determine the level of expression of the transgene in each transformed line. The data shown in the column labelled "Northern" in Table 2 below shows that the transformed plant lines containing the sense and anti-sense constructs for 4CL all exhibit high levels of expression, relative to the background on the Northern blots. 4CL expression in anti-sense plant line number 1 was not measured because the RNA was not available at the time of the experiment. There was no detectable hybridisation to RNA samples from empty vector-transformed control plants.

c) Modulation of 4CL Enzyme Activity in Transformed Plants

The total activity of 4CL enzyme, encoded by the Pinus 4CL gene and by the endogenous tobacco 4CL gene, in transformed tobacco plants was analysed for each transformed plant line created with the 4CL sense and anti-sense constructs. Crude protein extracts were prepared from each transformed plant and assayed using the method of Zhang et al. (*Plant Physiol.*, 113:65–74, 1997). The data contained in the column labeled "Enzyme" in Table 2 shows that the transformed plant lines containing the 4CL sense construct had elevated 4CL enzyme activity, with a maximum of 258%, and the transformed plant lines containing the 4CL anti-sense construct had reduced 4CL enzyme activity, with a minimum of 59%, relative to empty vector-transformed control plants.

d) Effects of Pinus 4CL on Lignin Concentration in Transformed Plants

The concentration of lignin in samples of transformed plant material was determined as described in Example 3. The data shown in the column labelled "TGA" in Table 2 shows that the transformed plant lines containing the sense and the anti-sense 4CL gene constructs all exhibited significantly decreased levels of lignin, relative to the empty vector-transformed control plant lines. These data clearly indicate that lignin concentration, as measured by the TGA assay, can be directly manipulated by either sense or anti-sense expression of a lignin biosynthetic gene such as 4CL.

TABLE 2

| plant line | transgene | orientation | Southern | Northern | Enzyme | TGA |
|---|---|---|---|---|---|---|
| 1 | control | na | + | blank | 100 | 92 |
| 2 | control | na | + | blank | 100 | 104 |
| 1 | 4CL | sense | + | 2.3E + 4 | 169 | 64 |
| 2 | 4CL | sense | + | 4.5E + 4 | 258 | 73 |
| 3 | 4CL | sense | + | 3.1E + 4 | 174 | 77 |
| 4 | 4CL | sense | + | 1.7E + 4 | 164 | 80 |
| 5 | 4CL | sense | + | 1.6E + 4 | 184 | 92 |
| 1 | 4CL | anti-sense | + | na | 59 | 75 |
| 2 | 4CL | anti-sense | + | 1.0E + 4 | 70 | 75 |
| 3 | 4CL | anti-sense | + | 9.6E + 3 | 81 | 80 |
| 4 | 4CL | anti-sense | + | 1.2E + 4 | 90 | 83 |
| 5 | 4CL | anti-sense | + | 4.7E + 3 | 101 | 88 |
| 6 | 4CL | anti-sense | + | 3.9E + 3 | 116 | 89 |
| 7 | 4CL | anti-sense | + | 1.8E + 3 | 125 | 94 |
| 8 | 4CL | anti-sense | + | 1.7E + 4 | 106 | 97 |

EXAMPLE 5

Transformation of Tobacco using the Inventive Lignin Biosynthetic Genes

Sense and anti-sense constructs containing DNA sequences including the coding regions of C3H (SEQ ID NO: 18), F5H (SEQ ID NO: 19), CCR (SEQ ID NO: 25) and CGT (SEQ ID NO: 31) from *Eucalyptus grandis*, and PAL (SEQ ID NO: 45 and 47), C4H (SEQ ID NO: 48 and 49), PNL (SEQ ID NO: 81) and LAC (SEQ ID NO: 83) from *Pinus radiata* were inserted into *Agrobacterium tumefaciens* LBA4301 by direct transformation as described above. The presence and integrity of the transgenic constructs were verified by restriction digestion and DNA sequencing.

Tobacco (*Nicotiana tabacum* cv. Samsun) leaf sections were transformed as described in Example 3. Up to twelve independent transformed plant lines were established for each sense construct and each anti-sense construct listed in the preceding paragraph. Transformed plants containing the appropriate lignin gene construct were verified using Southern blot experiments. All of the transformed plant lines analysed were confirmed as independent transformed lines.

EXAMPLE 6

Manipulation of Lignin Content in Transformed Plants a) Determination of Transgene Expression by Northern Blot Experiments Total RNA was isolated from each independent transformed plant line described in Example 5. The RNA samples were analysed in Northern blot experiments to determine the level of expression of the transgene in each transformed line. The column labelled "Northern" in Table 3 shows the level of transgene expression for all plant lines assayed, relative to the background on the Northern blots. There was no detectable hybridisation to RNA samples from empty vector-transformed control plants.

b) Determination of Lignin Concentration in Transformed Plants

The concentration of lignin in empty vector-transformed control plant lines and in up to twelve independent transformed lines for each sense construct and each anti-sense construct described in Example 5 was determined as described in Example 3. The column labelled "TGA" in Table 3 shows the thioglycolic acid extractable lignins for all plant lines assayed, expressed as the average percentage of TGA extractable lignins in transformed plants versus control plants. The range of variation is shown in parentheses.

TABLE 3

| transgene | orientation | no. of lines | Northern | TGA |
|---|---|---|---|---|
| control | na | 3 | blank | 100 (92–104) |
| C3H | sense | 5 | 3.7E + 4 | 74 (67–85) |
| F5H | sense | 10 | 5.8E + 4 | 70 (63–79) |
| F5H | anti-sense | 9 | 5.8E + 4 | 73 (35–93) |
| CCR | sense | 1 | na | 74 |
| CCR | anti-sense | 2 | na | 74 (62–86) |
| PAL | sense | 5 | 1.9E + 5 | 77 (71–86) |
| PAL | anti-sense | 4 | 1.5E + 4 | 62 (37–77) |
| C4H | anti-sense | 10 | 5.8E + 4 | 86 (52–113) |
| PNL | anti-sense | 6 | 1.2E + 4 | 88 (70–114) |
| LAC | sense | 5 | 1.7E + 5 | na |
| LAC | anti-sense | 12 | 1.7E + 5 | 88 (73–114) |

Transformed plant lines containing the sense and the anti-sense lignin biosynthetic gene constructs all exhibited significantly decreased levels of lignin, relative to the empty vector-transformed control plant lines. The most dramatic effects on lignin concentration were seen in the F5H anti-sense plants with as little as 35% of the amount of lignin in control plants, and in the PAL anti-sense plants with as little as 37% of the amount of lignin in control plants. These data clearly indicate that lignin concentration, as measured by the TGA assay, can be directly manipulated by conventional anti-sense methodology and also by sense over-expression using the inventive lignin biosynthetic genes.

EXAMPLE 7

Modulation of Lignin Enzyme Activity in Transformed Plants

The activities and substrate specificities of selected lignin biosynthetic enzymes were assayed in crude extracts from transformed tobacco plants containing sense and anti-sense constructs for PAL (SEQ ID NO: 45), PNL (SEQ ID NO: 81) and LAC (SEQ ID NO: 83) from *Pinus radiata*, and CGT (SEQ ID NO: 31) from *Eucalyptus grandis*.

Enzyme assays were performed using published methods for PAL (Southerton, S. G. and Deverall, B. J., *Plant Path.* 39:223–230, 1990), CGT (Vellekoop, P. et al., *FEBS,* 330:36–40, 1993), PNL (Espin, C. J. et al., *Phytochemistry,* 44:17–22, 1997) and LAC (Bao, W. et al., *Science,* 260:672–674, 1993). The data shown in the column labelled "Enzyme" in Table 4 shows the average enzyme activity from replicate measures for all plant lines assayed, expressed as a percent of enzyme activity in empty vector-transformed control plants. The range of variation is shown in parentheses.

TABLE 4

| Transgene | orientation | no. of lines | enzyme |
|---|---|---|---|
| control | na | 3 | 100 |
| PAL | sense | 5 | 87 (60–124) |
| PAL | anti-sense | 3 | 53 (38–80) |
| CGT | anti-sense | 1 | 89 |
| PNL | anti-sense | 6 | 144 (41–279) |
| LAC | sense | 5 | 78 (16–240) |
| LAC | anti-sense | 11 | 64 (14–106) |

All of the transformed plant lines, except the PNL anti-sense transformed plant lines, showed average lignin enzyme activities which were significantly lower than the activities observed in empty vector-transformed control plants. The most dramatic effects on lignin enzyme activities were seen in the PAL anti-sense transformed plant lines in which all of the lines showed reduced PAL activity and in the LAC anti-sense transformed plant lines which showed as little as 14% of the LAC activity in empty vector-transformed control plant lines.

EXAMPLE 8

Functional Identification of Lignin Biosynthetic Genes

Sense constructs containing DNA sequences including the coding regions for PAL (SEQ ID NO: 47), OMT (SEQ ID NO: 53), 4CL (SEQ ID NO: 56 and 57) and POX (SEQ ID NO: 86) from *Pinus radiata*, and OMT (SEQ ID NO: 23 and 24), CCR (SEQ ID NO: 26–28), CGT (SEQ ID NO: 31 and 33) and POX (SEQ ID NO: 42 and 44) from *Eucalyptus grandis* were inserted into the commercially available protein expression vector, pProEX-1 (Gibco BRL). The resultant constructs were transformed into *E. coli* XL1-Blue (Stratagene), which were then induced to produce recombinant protein by the addition of IPTG. Purified proteins were produced for the Pinus OMT and 4CL constructs and the Eucalyptus OMT and POX constructs using Ni column chromatography (Janknecht, R. et al., *Proc. Natl. Acad. Sci.*, 88:8972–8976, 1991). Enzyme assays for each of the purified proteins conclusively demonstrated the expected substrate specificity and enzymatic activity for the genes tested.

The data for two representative enzyme assay experiments, demonstrating the verification of the enzymatic activity of a *Pinus radiata* 4CL gene (SEQ ID NO: 56) and a *Pinus radiata* OMT gene (SEQ ID NO: 53), are shown in Table 5. For the 4CL enzyme, one unit equals the quantity of protein required to convert the substrate into product at the rate of 0.1 absorbance units per minute. For the OMT enzyme, one unit equals the quantity of protein required to convert 1 pmole of substrate to product per minute.

TABLE 5

| transgene | purification step | total ml extract | total mg protein | total units activity | % yield activity | fold purification |
|---|---|---|---|---|---|---|
| 4CL | crude | 10 ml | 51 mg | 4200 | 100 | 1 |
|  | Ni column | 4 ml | 0.84 mg | 3680 | 88 | 53 |
| OMT | crude | 10 ml | 74 mg | 4600 | 100 | 1 |
|  | Ni column | 4 ml | 1.2 mg | 4487 | 98 | 60 |

The data shown in Table 5 indicate that both the purified 4CL enzyme and the purified OMT enzyme show high activity in enzyme assays, confirming the identification of the 4CL and OMT genes described in this application. Crude protein preparations from *E. coli* transformed with empty vector show no activity in either the 4CL or the OMT enzyme assay.

Although the present invention has been described in some detail by way of illustration and example for purposes of clarity of understanding, changes and modifications can be carried out without departing from the scope of the invention which is intended to be limited only by the scope of the appended claims.

We claim:

1. An isolated DNA sequence comprising a nucleotide sequence selected from the group consisting of:
   (a) sequences recited in SEQ ID NO: 55, 57 and 59;
   (b) complements of the sequences recited in SEQ ID NO: 55, 57 and 59;
   (c) reverse complements of the sequences recited in SEQ ID NO: 55, 57 and 59; and
   (d) reverse sequences of the sequences recited in SEQ ID NO: 55, 57 and 59.

2. A DNA construct comprising a DNA sequence according to claim 1.

3. A transgenic cell comprising a DNA construct according to claim 2.

4. A DNA construct comprising, in the 5'-3' direction:
   (a) a gene promoter sequence,
   (b) an open reading frame coding for an enzyme encoded by a nucleotide sequence selected from the group consisting of sequences recited in SEQ ID NO: 55, 57 and 59; and
   (c) a gene termination sequence.

5. The DNA construct of claim 4 wherein the open reading frame is in a sense orientation.

6. The DNA construct of claim 4, wherein the gene promoter sequence and gene termination sequences are functional in a plant host.

7. The DNA construct of claim 4, wherein the gene promoter sequence provides for transcription in xylem.

8. The DNA construct of claim 4 further comprising a marker for identification of transformed cells.

9. A transgenic plant cell comprising a DNA construct, the DNA construct comprising, in the 5'-3' direction:
   (a) a gene promoter sequence;
   (b) an open reading frame coding for an enzyme encoded by a nucleotide sequence selected from the group consisting of sequences recited in SEQ ID NO: 55, 57 and 59; and
   (c) a gene termination sequence.

10. The transgenic plant cell of claim 9 wherein the open reading frame is in a sense orientation.

11. The transgenic plant cell of claim 9 wherein the DNA construct further comprises a marker for identification of transformed cells.

12. A plant comprising a transgenic plant cell according to claim 9, or fruit or seeds thereof.

13. The plant of claim 12 wherein the plant is a woody plant.

14. The plant of claim 13 wherein the plant is selected from the group consisting of eucalyptus and pine species.

15. A method for modulating the lignin content of a plant comprising stably incorporating into the genome of the plant a DNA construct comprising, in the 5'-3' direction:
    (a) a gene promoter sequence;
    (b) an open reading frame coding for an enzyme encoded by a nucleotide sequence selected from the group consisting of sequences recited in SEQ ID NO: 55, 57 and 59; and
    (c) a gene termination sequence.

16. The method of claim 15 wherein the plant is selected from the group consisting of eucalyptus and pine species.

17. The method of claim 15 wherein the open reading frame is in a sense orientation.

18. A method for producing a plant having altered lignin structure comprising:
    (a) transforming a plant cell with a DNA construct comprising, in the 5'-3' direction, a gene promoter sequence, an open reading frame coding for an enzyme encoded by a nucleotide sequence selected from the group consisting of sequences recited in SEQ ID NO: 55, 57, and 59; and
    (b) cultivating the transgenic cell under conditions conductive to regeneration and mature plant growth.

19. The method of claim 18 wherein the open reading frame is in a sense orientation.

20. The method of claim 18 wherein the plant is a woody plant.

21. The method of claim 20 wherein the plant is selected from the group consisting of eucalyptus and pine species.

22. A method of modifying the activity of an enzyme in a plant comprising stably incorporating into the genome of the plant a DNA construct including
    (a) a gene promoter sequence;
    (b) an open reading frame coding for an enzyme encoded by a nucleotide sequence selected from the group consisting of sequences recited in SEQ ID NO: 55, 57 and 59; and
    (c) a gene termination sequence.

23. The method of claim 22 wherein the open reading frame is in a sense orientation.

* * * * *